United States Patent
Cooper et al.

(10) Patent No.: US 7,175,644 B2
(45) Date of Patent: Feb. 13, 2007

(54) DEVICES AND METHODS FOR MAINTAINING COLLATERAL CHANNELS IN TISSUE

(75) Inventors: Joel D. Cooper, St. Louis, MO (US); James M. Davenport, Fallbrook, CA (US); Bryan Loomas, Los Gatos, CA (US); Don Tanaka, Saratoga, CA (US); Gary Kaplan, San Francisco, CA (US)

(73) Assignee: Broncus Technologies, Inc., Mountain View, CA (US)

( * ) Notice: Subject to any disclaimer, the term of this patent is extended or adjusted under 35 U.S.C. 154(b) by 0 days.

(21) Appl. No.: 09/947,144

(22) Filed: Sep. 4, 2001

(65) Prior Publication Data

US 2002/0111620 A1    Aug. 15, 2002

Related U.S. Application Data

(60) Provisional application No. 60/269,130, filed on Feb. 14, 2001.

(51) Int. Cl.
*A61M 29/00* (2006.01)
*A61F 2/06* (2006.01)

(52) U.S. Cl. ............... 606/191; 606/192; 623/1.16
(58) Field of Classification Search ........ 606/191–198; 604/45, 103.06, 104–106; 623/1.1, 1.12, 623/1.15, 1.16, 1.28
See application file for complete search history.

(56) References Cited

U.S. PATENT DOCUMENTS

| | | | |
|---|---|---|---|
| 2,127,903 A | 8/1938 | Bowen | |
| 3,779,234 A | 12/1973 | Eggleton et al. | |
| 3,942,530 A | 3/1976 | Northeved | |
| 4,503,569 A | 3/1985 | Dotter | |
| 4,534,761 A | 8/1985 | Raible | |
| 4,538,618 A | 9/1985 | Rosenberg et al. | |
| 4,582,067 A | 4/1986 | Silverstein et al. | |
| 4,583,969 A | 4/1986 | Mortensen | |

(Continued)

FOREIGN PATENT DOCUMENTS

JP    2000-107178    4/2000

(Continued)

OTHER PUBLICATIONS

Cordis® Johnson & Johnson Gateway$^{SM}$ LLC: Bx VELOCITY Stent. Viewed at: http://www.jnjgateway.com/home.jhtml?loc=USENG&page=viewContent&contentId=fc0de00100001015&parentId=fc0de00100001015&specialty=Circulatory_Disease_Management&category=Cardiac_Diagnosis_Interventions&subcategory=Stents_Balloon_Expandable Viewed on Sep. 5, 2002. 4 pages (please note p. 4 of 4 is blank).

(Continued)

*Primary Examiner*—Michael Peffley
(74) *Attorney, Agent, or Firm*—Levine Bagade Han LLP

(57) ABSTRACT

The devices and methods of placement of such devices disclosed herein are directed to altering gaseous flow within a lung to improve the expiration cycle of, for instance, an individual having Chronic Obstructive Pulmonary Disease. More particularly, these devices produce and maintain collateral openings or channels through the airway wall so that oxygen depleted/carbon dioxide rich air is able to pass directly out of the lung tissue to facilitate both the exchange of oxygen ultimately into the blood and/or to decompress hyper-inflated lungs. The medical kits disclosed herein are also directed to produce and maintain collateral openings through airway walls.

25 Claims, 38 Drawing Sheets

U.S. PATENT DOCUMENTS

| | | |
|---|---|---|
| 4,674,498 A | 6/1987 | Stasz |
| 4,676,782 A | 6/1987 | Yamamoto et al. |
| 4,682,596 A | 7/1987 | Bales et al. |
| 4,687,482 A | 8/1987 | Hanson |
| 4,750,902 A | 6/1988 | Wuchinich et al. |
| 4,753,236 A | 6/1988 | Healey |
| 4,757,821 A | 7/1988 | Snyder |
| 4,757,822 A | 7/1988 | Di Giuliomaria et al. |
| 4,769,031 A | 9/1988 | McGough |
| 4,770,185 A | 9/1988 | Silverstein et al. |
| 4,771,788 A | 9/1988 | Millar |
| 4,773,413 A | 9/1988 | Hussein et al. |
| 4,785,402 A | 11/1988 | Matsuo et al. |
| 4,795,465 A | 1/1989 | Marten |
| 4,802,476 A | 2/1989 | Noerenberg et al. |
| 4,807,634 A | 2/1989 | Enjoji et al. |
| 4,834,102 A | 5/1989 | Schwarzchild et al. |
| 4,869,268 A | 9/1989 | Yoon |
| 4,870,953 A | 10/1989 | DonMicheal et al. |
| 4,887,606 A | 12/1989 | Yock et al. |
| 4,892,099 A * | 1/1990 | Ohkawa et al. ............. 606/194 |
| 4,899,757 A | 2/1990 | Pope, Jr. et al. |
| 4,917,097 A | 4/1990 | Proudian et al. |
| 4,955,377 A * | 9/1990 | Lennox et al. ............. 607/105 |
| 4,957,508 A | 9/1990 | Kaneko et al. |
| 4,967,753 A | 11/1990 | Haase et al. |
| 4,973,301 A | 11/1990 | Nissenkorn |
| 4,976,690 A * | 12/1990 | Solar et al. ............. 604/103.06 |
| 4,977,898 A | 12/1990 | Schwarzschild et al. |
| 5,002,058 A | 3/1991 | Martinelli |
| 5,030,201 A | 7/1991 | Palestrant |
| 5,054,483 A | 10/1991 | Marten et al. |
| 5,061,275 A | 10/1991 | Wallstén et al. |
| 5,064,435 A | 11/1991 | Porter |
| 5,081,993 A | 1/1992 | Kitney et al. |
| 5,105,816 A | 4/1992 | Shimura et al. |
| 5,105,817 A | 4/1992 | Uchibori et al. |
| 5,127,917 A | 7/1992 | Niederhauser et al. |
| 5,148,809 A | 9/1992 | Biegeleisen-Knight et al. |
| 5,170,793 A | 12/1992 | Takano et al. |
| 5,201,316 A | 4/1993 | Pomeranz et al. |
| 5,238,027 A | 8/1993 | Lee |
| 5,257,990 A | 11/1993 | Nash |
| 5,261,409 A | 11/1993 | Dardel |
| 5,273,529 A | 12/1993 | Idowu |
| 5,275,166 A | 1/1994 | Vaitekunas et al. |
| 5,282,824 A | 2/1994 | Gianturco |
| 5,299,578 A | 4/1994 | Rotteveel et al. |
| 5,309,915 A | 5/1994 | Ember |
| 5,313,950 A | 5/1994 | Ishikawa et al. |
| 5,320,106 A | 6/1994 | Tanaka |
| 5,330,500 A | 7/1994 | Song |
| 5,334,146 A * | 8/1994 | Ozasa ................... 604/103.06 |
| 5,334,210 A | 8/1994 | Gianturco |
| 5,339,289 A | 8/1994 | Erickson |
| 5,344,420 A | 9/1994 | Hilal et al. |
| 5,351,693 A | 10/1994 | Taimisto et al. |
| 5,363,853 A | 11/1994 | Lieber et al. |
| 5,368,035 A | 11/1994 | Hamm et al. |
| 5,375,602 A | 12/1994 | Lancee et al. |
| 5,381,795 A | 1/1995 | Nordgren et al. |
| 5,383,460 A | 1/1995 | Jang et al. |
| 5,383,887 A | 1/1995 | Nadal |
| 5,385,148 A | 1/1995 | Lesh et al. |
| 5,402,792 A | 4/1995 | Kimura |
| 5,413,601 A | 5/1995 | Keshelava |
| 5,425,739 A | 6/1995 | Jessen |
| 5,427,107 A | 6/1995 | Milo et al. |
| 5,435,314 A | 7/1995 | Dias |
| 5,443,498 A * | 8/1995 | Fontaine ................... 623/1.17 |
| 5,454,373 A | 10/1995 | Koger et al. |
| 5,456,258 A | 10/1995 | Kondo et al. |
| 5,458,120 A | 10/1995 | Lorraine |
| 5,464,016 A | 11/1995 | Nicholas et al. |
| 5,465,726 A | 11/1995 | Dickinson et al. |
| 5,466,242 A | 11/1995 | Mori |
| 5,474,075 A | 12/1995 | Goldberg et al. |
| 5,485,841 A | 1/1996 | Watkin et al. |
| 5,505,088 A | 4/1996 | Chandraratna et al. |
| 5,514,154 A | 5/1996 | Lau et al. |
| 5,520,684 A | 5/1996 | Imran |
| 5,522,822 A | 6/1996 | Phelps et al. |
| 5,527,324 A | 6/1996 | Krantz et al. |
| 5,540,713 A | 7/1996 | Schnepp-Pesch et al. |
| 5,545,195 A | 8/1996 | Lennox et al. |
| 5,545,210 A | 8/1996 | Hess et al. |
| 5,555,886 A | 9/1996 | Weng et al. |
| 5,571,180 A | 11/1996 | Blom |
| 5,575,818 A | 11/1996 | Pinchuk |
| 5,593,417 A | 1/1997 | Rhodes |
| 5,596,989 A | 1/1997 | Morita |
| 5,607,444 A | 3/1997 | Lam |
| 5,615,679 A | 4/1997 | Ri et al. |
| 5,618,301 A | 4/1997 | Hauenstein et al. |
| D380,266 S | 6/1997 | Boatman et al. |
| 5,645,559 A | 7/1997 | Hachtman et al. |
| 5,647,871 A | 7/1997 | Levine et al. |
| 5,653,746 A | 8/1997 | Schmitt |
| 5,658,280 A | 8/1997 | Issa |
| 5,672,172 A | 9/1997 | Zupkas |
| 5,674,277 A | 10/1997 | Freitag |
| 5,674,298 A | 10/1997 | Levy et al. |
| 5,678,555 A | 10/1997 | O'Connell |
| 5,693,085 A | 12/1997 | Buirge et al. |
| 5,704,361 A | 1/1998 | Seward et al. |
| 5,713,949 A | 2/1998 | Jayaraman |
| 5,716,393 A | 2/1998 | Lindenberg et al. |
| 5,725,547 A | 3/1998 | Chuter |
| 5,733,301 A * | 3/1998 | Forman ..................... 606/192 |
| 5,741,234 A | 4/1998 | Aboul-Hosn |
| 5,741,333 A | 4/1998 | Frid |
| 5,752,518 A | 5/1998 | McGee et al. |
| 5,755,769 A | 5/1998 | Richard et al. |
| 5,755,778 A | 5/1998 | Kleshinski |
| 5,759,769 A | 6/1998 | Sia et al. |
| 5,792,119 A | 8/1998 | Marx |
| 5,795,325 A | 8/1998 | Valley et al. |
| 5,797,920 A | 8/1998 | Kim |
| 5,810,008 A | 9/1998 | Dekel et al. |
| 5,810,836 A | 9/1998 | Hussein et al. |
| 5,824,046 A | 10/1998 | Smith et al. |
| 5,830,191 A | 11/1998 | Hildwein et al. |
| 5,830,222 A | 11/1998 | Makower |
| 5,840,431 A | 11/1998 | Kall |
| 5,843,175 A | 12/1998 | Frantzen |
| 5,846,205 A | 12/1998 | Curley et al. |
| 5,849,037 A | 12/1998 | Frid |
| 5,855,597 A | 1/1999 | Jayaraman |
| 5,860,951 A | 1/1999 | Eggers et al. |
| 5,868,763 A | 2/1999 | Spence et al. |
| 5,876,345 A | 3/1999 | Eaton et al. |
| 5,876,434 A | 3/1999 | Flomenblit et al. |
| 5,876,445 A * | 3/1999 | Andersen et al. .......... 623/23.7 |
| 5,876,448 A | 3/1999 | Thompson et al. |
| 5,921,995 A | 7/1999 | Kleshinski |
| 5,922,019 A | 7/1999 | Hankh et al. |
| 5,935,135 A | 8/1999 | Bramfitt et al. |
| 5,938,697 A | 8/1999 | Killion et al. |
| 5,951,567 A | 9/1999 | Javier, Jr. et al. |
| 5,957,849 A | 9/1999 | Munro |
| 5,967,990 A | 10/1999 | Thierman et al. |
| 5,968,053 A | 10/1999 | Revelas |
| 5,968,070 A | 10/1999 | Bley et al. |
| 5,972,017 A | 10/1999 | Berg et al. |

| | | |
|---|---|---|
| 5,984,871 A | 11/1999 | TenHoff et al. |
| 5,993,484 A | 11/1999 | Shmulewitz |
| 6,001,124 A | 12/1999 | Bachinski |
| 6,003,517 A | 12/1999 | Sheffield et al. |
| 6,004,273 A | 12/1999 | Sakamoto et al. |
| 6,004,319 A | 12/1999 | Gobel et al. |
| 6,007,544 A | 12/1999 | Kim |
| 6,007,574 A | 12/1999 | Pulnev et al. |
| 6,010,529 A | 1/2000 | Herweck et al. |
| 6,011,995 A | 1/2000 | Guglielmi et al. |
| 6,013,033 A | 1/2000 | Berger et al. |
| 6,013,093 A | 1/2000 | Nott et al. |
| 6,013,854 A | 1/2000 | Moriuchi |
| 6,015,405 A | 1/2000 | Schwartz et al. |
| 6,019,787 A | 2/2000 | Richard et al. |
| 6,022,371 A | 2/2000 | Killion |
| 6,024,703 A | 2/2000 | Zanelli et al. |
| 6,030,392 A | 2/2000 | Dakov |
| 6,036,702 A | 3/2000 | Bachinski et al. |
| 6,045,511 A | 4/2000 | Ott et al. |
| 6,048,362 A | 4/2000 | Berg |
| 6,053,941 A | 4/2000 | Lindenberg et al. |
| 6,059,731 A | 5/2000 | Seward et al. |
| 6,059,811 A | 5/2000 | Pinchasik et al. |
| 6,063,111 A | 5/2000 | Hieshima et al. |
| 6,068,638 A | 5/2000 | Makower |
| 6,074,349 A | 6/2000 | Crowley |
| 6,074,416 A | 6/2000 | Berg et al. |
| 6,096,053 A | 8/2000 | Bates |
| 6,112,123 A | 8/2000 | Kelleher et al. |
| 6,113,612 A | 9/2000 | Swanson et al. |
| 6,120,432 A | 9/2000 | Sullivan et al. |
| 6,129,726 A | 10/2000 | Edwards et al. |
| 6,135,997 A | 10/2000 | Laufer et al. |
| 6,143,019 A | 11/2000 | Motamedi et al. |
| 6,152,937 A | 11/2000 | Peterson et al. |
| 6,152,945 A | 11/2000 | Bachinski et al. |
| 6,159,225 A | 12/2000 | Makower |
| 6,162,245 A | 12/2000 | Jayaraman |
| 6,183,444 B1 | 2/2001 | Glines et al. |
| 6,186,942 B1 | 2/2001 | Sullivan et al. |
| 6,190,353 B1 | 2/2001 | Makower et al. |
| 6,231,587 B1 * | 5/2001 | Makower .................... 606/198 |
| 6,241,742 B1 | 6/2001 | Spence et al. |
| 6,241,746 B1 | 6/2001 | Bosma et al. |
| 6,245,102 B1 | 6/2001 | Jayaraman |
| 6,258,100 B1 | 7/2001 | Alferness et al. |
| 6,258,115 B1 | 7/2001 | Dubrul |
| 6,264,690 B1 * | 7/2001 | Von Oepen .................... 623/1.3 |
| 6,270,524 B1 | 8/2001 | Kim |
| 6,280,457 B1 | 8/2001 | Wallace et al. |
| 6,283,951 B1 | 9/2001 | Flaherty et al. |
| 6,283,983 B1 | 9/2001 | Makower et al. |
| 6,287,290 B1 | 9/2001 | Perkins et al. |
| 6,290,728 B1 | 9/2001 | Phelps et al. |
| 6,293,951 B1 | 9/2001 | Alferness et al. |
| 6,299,635 B1 | 10/2001 | Frantzen |
| 6,309,375 B1 | 10/2001 | Gliner et al. |
| 6,309,416 B1 | 10/2001 | Swanson et al. |
| 6,325,825 B1 * | 12/2001 | Kula et al. .................... 623/1.3 |
| 6,328,689 B1 | 12/2001 | Gonzalez et al. |
| 6,336,933 B1 | 1/2002 | Parodi |
| 6,344,053 B1 | 2/2002 | Boneau |
| 6,371,964 B1 | 4/2002 | Vargas et al. |
| 6,428,550 B1 | 8/2002 | Vargas et al. |
| 2001/0021872 A1 | 9/2001 | Bailey et al. |
| 2001/0047180 A1 | 11/2001 | Grudem et al. |
| 2002/0002401 A1 | 1/2002 | McGuckin, Jr. et al. |
| 2002/0055772 A1 | 5/2002 | McGuckin, Jr. et al. |

FOREIGN PATENT DOCUMENTS

| | | |
|---|---|---|
| JP | 2001-104315 | 4/2001 |
| WO | WO 95/02361 | 1/1995 |
| WO | WO 96/39914 | 12/1996 |
| WO | WO 97/17014 | 5/1997 |
| WO | WO 97/17105 | 5/1997 |
| WO | WO 98/16161 | 4/1998 |
| WO | WO 98/28035 | 7/1998 |
| WO | WO 98/48706 | 11/1998 |
| WO | WO 99/38454 | 8/1999 |
| WO | WO 99/60953 | 12/1999 |
| WO | WO 00/45742 A1 | 8/2000 |
| WO | WO 00/67825 | 11/2000 |
| WO | WO 00/72908 | 12/2000 |
| WO | WO 01/13839 | 3/2001 |
| WO | WO 01/28433 | 4/2001 |
| WO | WO 01/32088 | 5/2001 |
| WO | WO 01/70117 | 9/2001 |
| WO | WO 02/00278 | 1/2002 |

OTHER PUBLICATIONS

Pulmonary and Critical Care Medicine. Interventional Bronchoscopy with Stent Implant: Stents. Viewed at: http://views.vcu.edu/pulm-ccm/stents.html Viewed on Aug. 26, 2002. 2 pages.
"Emphysema", *National Heart, Lung, and Blood Institute*. (pp. 1-5). (General information sheet on emphysema).
Panettieri, R.A. (1995). "Chronic Obstructive Pulmonary Disease" Chapter 6 *In Lippincott's Patholphysiology Series: Pulmonary Pathophysiology*. M.A. Grippi ed., J.B. Lippincott Company, Philadelphia, pp. 93-107.

* cited by examiner

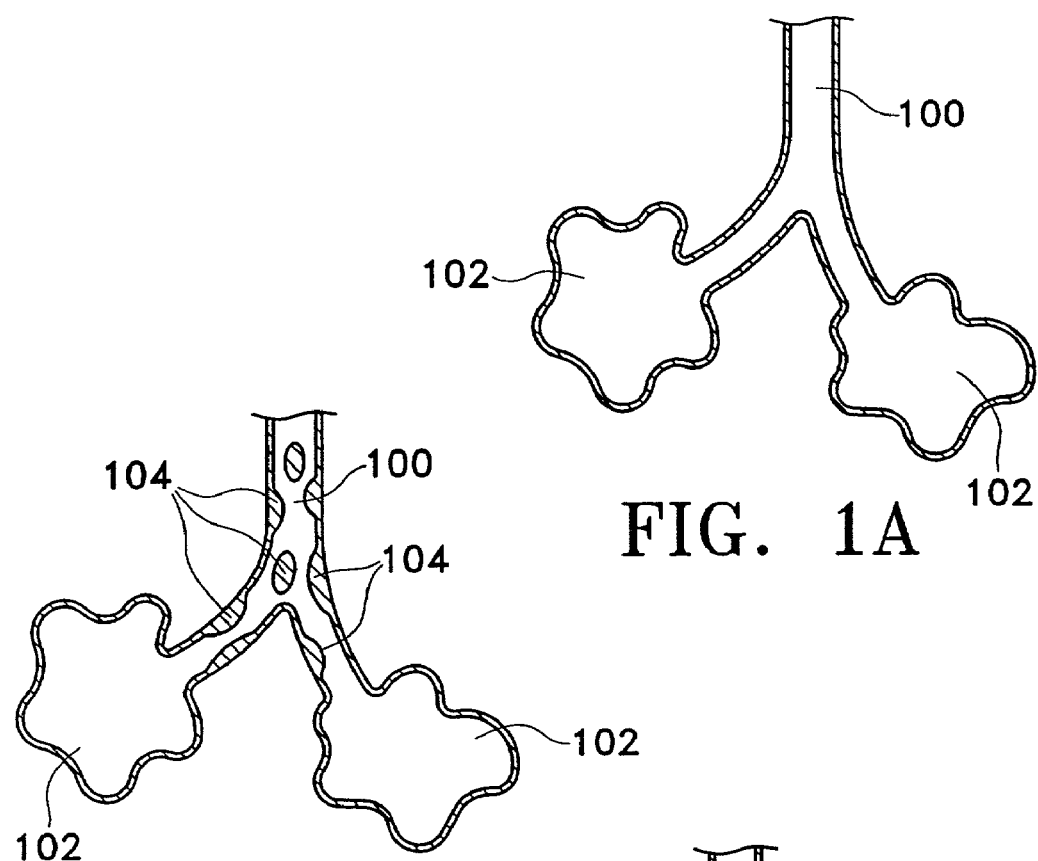
FIG. 1A
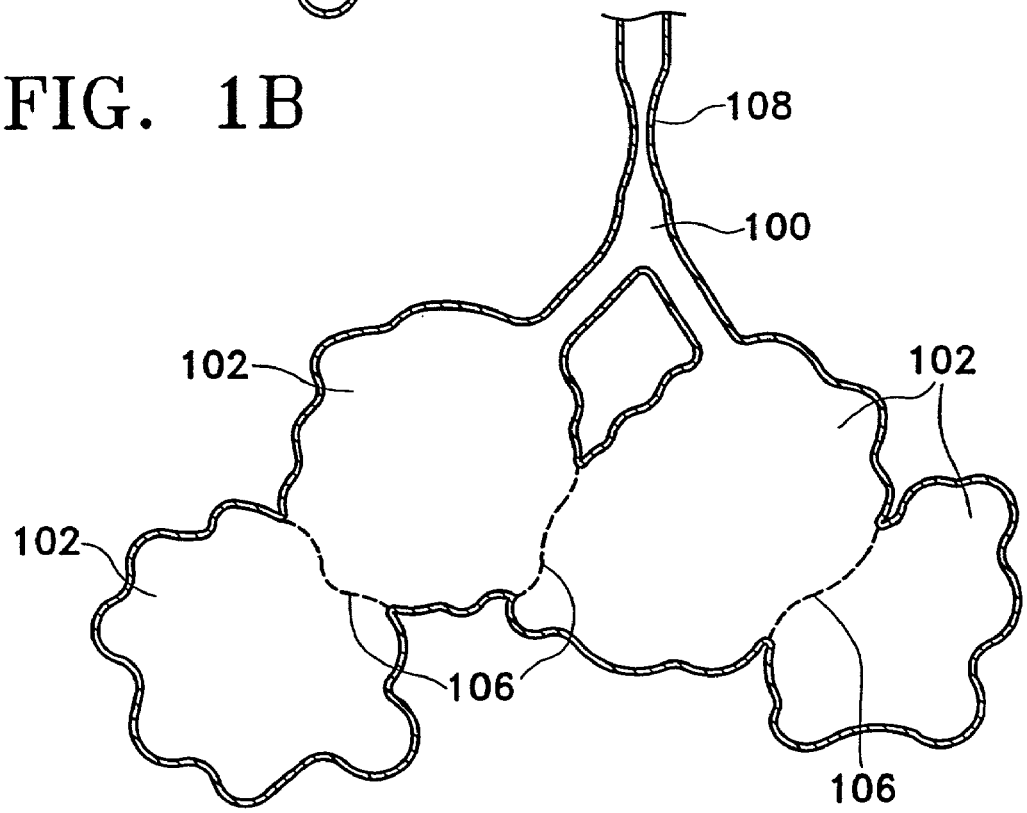
FIG. 1B
FIG. 1C

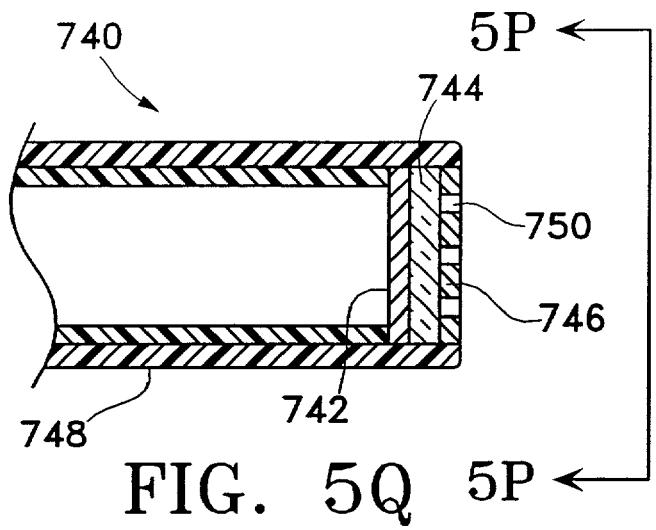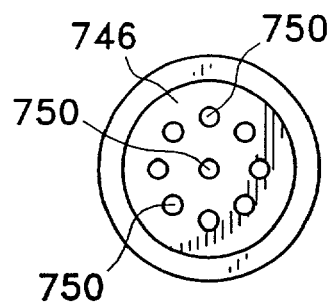
FIG. 5Q  FIG. 5P
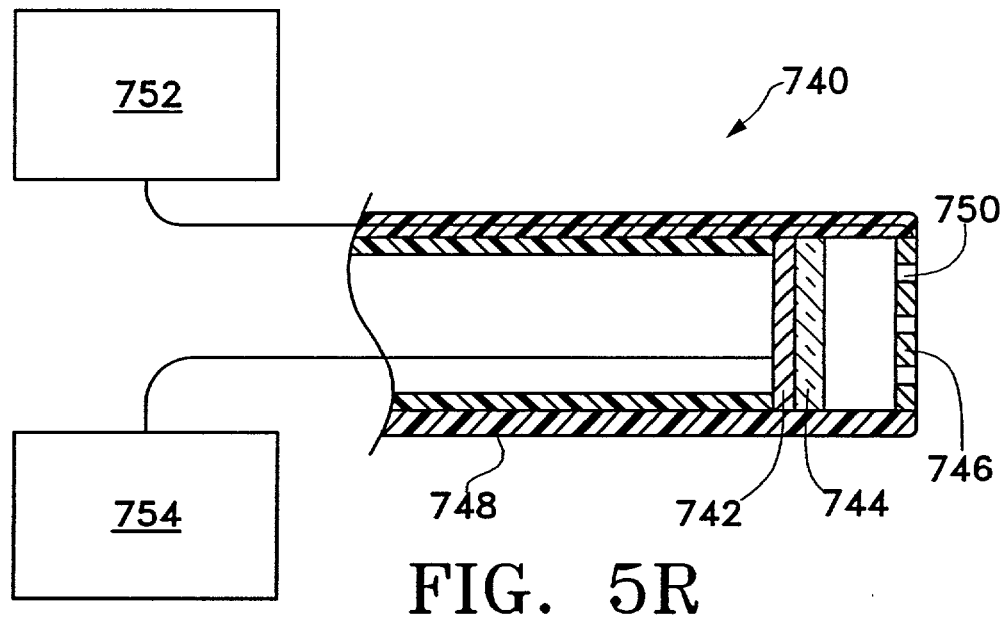
FIG. 5R
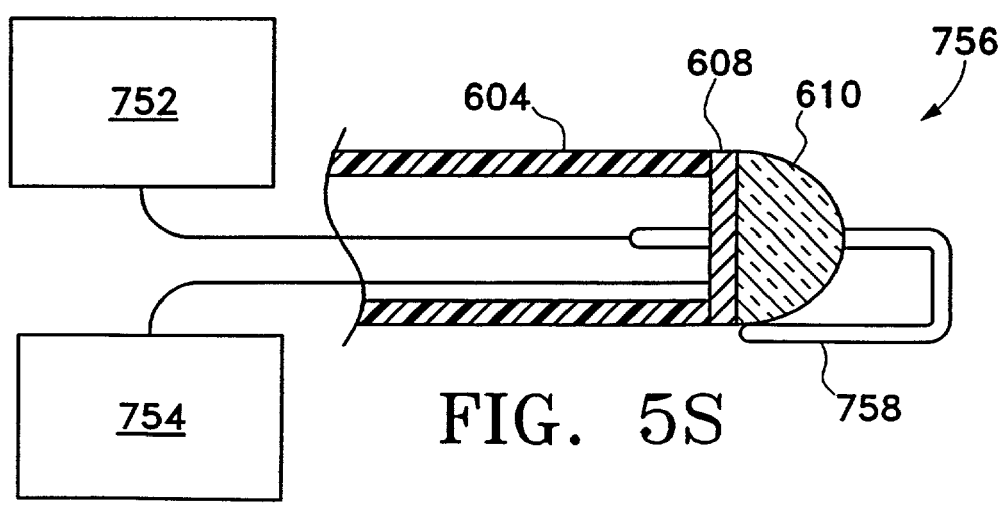
FIG. 5S

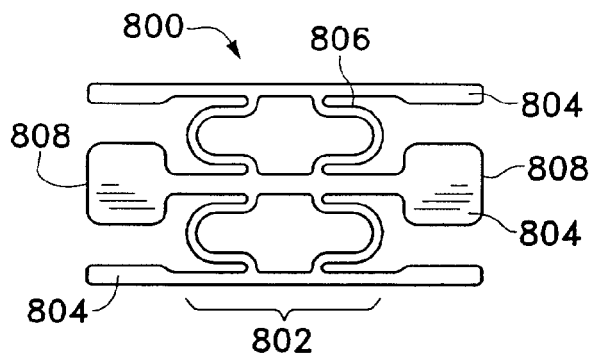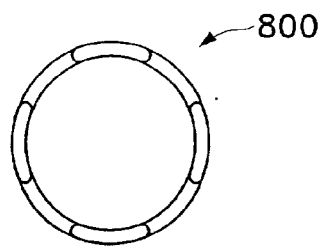
FIG. 9A  FIG. 9B
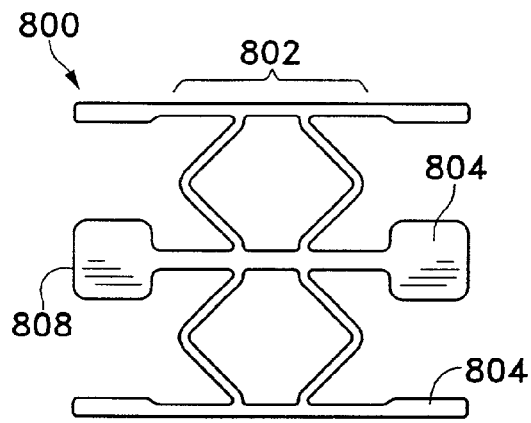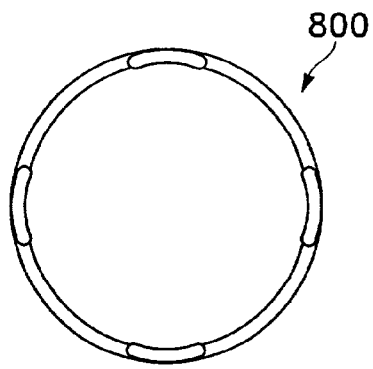
FIG. 9C  FIG. 9D
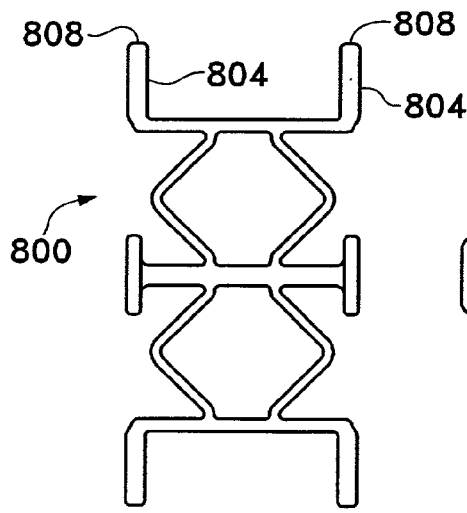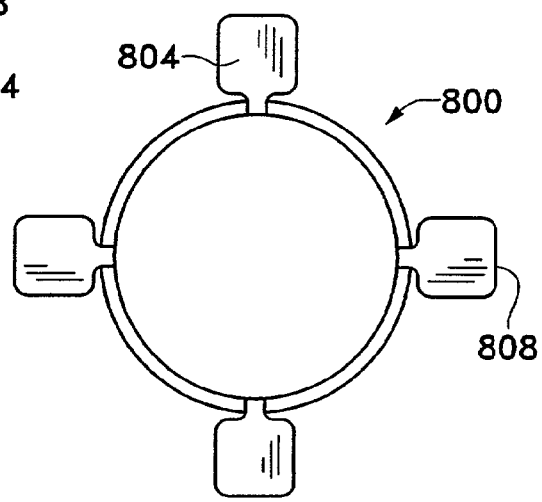
FIG. 9E  FIG. 9F

DEVICES AND METHODS FOR MAINTAINING COLLATERAL CHANNELS IN TISSUE

CROSS-REFERENCE TO RELATED APPLICATIONS

This application claims the benefit of U.S. Provisional Patent Application Ser. No. 60/269,130, filed on Feb. 14, 2001, which is incorporated herein by reference in its entirety.

FIELD OF THE INVENTION

The invention is directed to devices and methods of placing such devices to altering gaseous flow within a lung to improve the expiration cycle of an individual, particularly individuals having Chronic Obstructive Pulmonary Disease (COPD). More particularly, methods and devices are disclosed to produce and to maintain collateral openings or channels through the airway wall so that oxygen depleted/carbon dioxide rich air is able to pass directly out of the lung tissue to facilitate both the exchange of oxygen ultimately into the blood and/or to decompress hyper-inflated lungs. The invention is also directed to medical kits disclosed which produce and maintain collateral openings through airway walls.

BACKGROUND OF THE INVENTION

The term "Chronic Obstructive Pulmonary Disease" (COPD) is generally used to describe the disorders of emphysema and chronic bronchitis. Previously, COPD was also known as Chronic Obstructive Lung Disease (COLD), Chronic Airflow Obstruction (CAO), or Chronic Airflow Limitation (CAL). Some also consider certain types of asthma to fall under the definition of COPD. Emphysema is characterized by an enlargement of air spaces inside the lung. Hence, emphysema is an anatomic definition and it can only be presumed in a living patient. Chronic bronchitis is characterized by excessive mucus production in the bronchial tree. Chronic bronchitis is a clinical definition and denotes those individuals who meet criteria defining the disease. It is not uncommon for an individual to suffer from both disorders.

In 1995, the American Lung Association (ALA) estimated that between 15–16 million Americans suffered from COPD. The ALA estimated that COPD was the fourth-ranking cause of death in the U.S. The ALA estimates that the rates of emphysema is 7.6 per thousand population, and the rate for chronic bronchitis is 55.7 per thousand population.

Those inflicted with COPD face disabilities due to the limited pulmonary functions. Usually, individuals afflicted by COPD also face loss in muscle strength and an inability to perform common daily activities. Often, those patients desiring treatment for COPD seek a physician at a point where the disease is advanced. Since the damage to the lungs is irreversible, there is little hope of recovery. Most times, the physician cannot reverse the effects of the disease but can only offer treatment and advice to halt the progression of the disease.

To understand the detrimental effects of COPD, the workings of the lungs requires a cursory discussion. The primary function of the lungs is to permit the exchange of two gasses by removing carbon dioxide from venous blood and replacing it with oxygen. Thus, to facilitate this exchange, the lungs provide a blood gas interface. The oxygen and carbon dioxide move between the gas (air) and blood by diffusion. This diffusion is possible since the blood is delivered to one side of the blood-gas interface via small blood vessels (capillaries). The capillaries are wrapped around numerous air sacs called alveoli which function as the blood-gas interface. A typical human lung contains about 300 million alveoli.

The air is brought to the other side of this blood-gas interface by a natural respiratory airway, hereafter referred to as a natural airway or airway, consisting of branching tubes which become narrower, shorter, and more numerous as they penetrate deeper into the lung. Specifically, the airway begins with the trachea which branches into the left and right bronchi which divide into lobar, then segmental bronchi. Ultimately, the branching continues down to the terminal bronchioles which lead to the alveoli. Plates of cartilage may be found as part of the walls throughout most of the airway from the trachea to the bronchi. The cartilage plates become less prevalent as the airways branch. Eventually, in the last generations of the bronchi, the cartilage plates are found only at the branching points. The bronchi and bronchioles may be distinguished as the bronchi lie proximal to the last plate of cartilage found along the airway, while the bronchiole lies distal to the last plate of cartilage. The bronchioles are the smallest airways that do not contain alveoli. The function of the bronchi and bronchioles is to provide conducting air ways that lead inspired air to the gas-blood interface. However, these conducting airways do not take part in gas exchange because they do not contain alveoli. Rather, the gas exchange takes place in the alveoli which are found in the distal most end of the airways.

The mechanics of breathing include the lungs, the rib cage, the diaphragm and abdominal wall. During inspiration, inspiratory muscles contract increasing the volume of the chest cavity. As a result of the expansion of the chest cavity, the pleural pressure, the pressure within the chest cavity, becomes sub-atmospheric with respect to the pressure at the airway openings. Consequently, air flows into the lungs causing the lungs to expand. During unforced expiration, the expiratory muscles relax and the lungs begin to recoil and reduce in size. The lungs recoil because they contain elastic fibers that allow for expansion, as the lungs inflate, and relaxation, as the lungs deflate, with each breath. This characteristic is called elastic recoil. The recoil of the lungs causes alveolar pressure to exceed the pressure at airway openings causing air to flow out of the lungs and deflate the lungs. If the lungs' ability to recoil is damaged, the lungs cannot contract and reduce in size from their inflated state. As a result, the lungs cannot evacuate all of the inspired air.

Emphysema is characterized by irreversible damage to the alveolar walls. The air spaces distal to the terminal bronchiole become enlarged with destruction of their walls which deteriorate due to a bio-chemical breakdown. As discussed above, the lung is elastic, primarily due to elastic fibers and tissues called elastin found in the airways and air sacs. If these fibers and tissues become weak the elastic recoil ability of the lungs decreases. The loss of elastic recoil contributes to more air entering the air sacs than can exit preventing the lungs from reducing in size from their inflated state. Also, the bio-chemical breakdown of the walls of the alveolar walls causes a loss of radial support for airways which results in a narrowing of the airways on expiration.

Chronic bronchitis is characterized by excessive mucus production in the bronchial tree. Usually there is a general increase in bulk (hypertrophy) of the large bronchi and chronic inflammatory changes in the small airways. Excessive amounts of mucus are found in the airways and semisolid plugs of this mucus may occlude some small bronchi. Also, the small airways are usually narrowed and show inflammatory changes.

In COPD, a reduction in airflow arises as a result of 1) partial airway occlusion by excess secretions, 2) airway narrowing secondary to smooth muscle contraction, bronchial wall edema and inflation of the airways, and 3) reduction in both lung elasticity and tethering forces exerted on the airways which maintain patency of the lumen. As a result of the COPD, the airways close prematurely at an abnormally high lung volume. As mentioned above, in an emphysematous lung there is a decrease of lung parenchyma as there are larger and fewer air sacs. Thus, there is a decrease in the amount of parenchymal tissue which radially supports the airways. This loss of radial traction allows the airway to collapse more easily. As lung recoil decreases and airway closure occurs at higher lung volumes, the residual volume of gas in the lung increases. Consequently, this increased residual gas volume interferes with the ability of the lung to draw in additional fresh gas during inspiration. As a result, a person with advanced COPD can only take short shallow breaths.

One aspect of an emphysematous lung is that the flow of air between neighboring air sacs, known as collateral ventilation, is much more prevalent as compared to a normal lung. Yet, while the resistance to collateral ventilation may be decreased in an emphysematous lung the decreased resistance does not assist the patient in breathing due to the inability of the gasses to enter and exit the lungs as a whole.

Currently, although there is no cure for COPD, treatment includes bronchodilator drugs, and lung reduction surgery. The bronchodilator drugs relax and widen the air passages thereby reducing the residual volume and increasing gas flow permitting more oxygen to enter the lungs. Yet, bronchodilator drugs are only effective for a short period of time and require repeated application. Moreover, the bronchodilator drugs are only effective in a certain percentage of the population of those diagnosed with COPD. In some cases, patients suffering from COPD are given supplemental oxygen to assist in breathing. Unfortunately, aside from the impracticalities of needing to maintain and transport a source of oxygen for everyday activities, the oxygen is only partially functional and does not eliminate the effects of the COPD. Moreover, patients requiring a supplemental source of oxygen are usually never able to return to functioning without the oxygen.

Lung volume reduction surgery is a procedure which removes portions of the lung that are over-inflated. The improvement to the patient occurs as a portion of the lung that remains has relatively better elastic recoil which allows for reduced airway obstruction. The reduced lung volume also improves the efficiency of the respiratory muscles. However, lung reduction surgery is an extremely traumatic procedure which involves opening the chest and thoracic cavity to remove a portion of the lung. As such, the procedure involves an extended recovery period. Hence, the long term benefits of this surgery are still being evaluated. In any case, it is thought that lung reduction surgery is sought in those cases of emphysema where only a portion of the lung is emphysematous as opposed to the case where the entire lung is emphysematous. In cases where the lung is only partially emphysematous, removal of a portion of emphysematous lung increases the cavity area in which the non-diseased parenchyma may expand and contract. If the entire lung were emphysematous, the parenchyma is less elastic and cannot expand to take advantage of an increased area within the lung cavity.

Both bronchodilator drugs and lung reduction surgery fail to capitalize on the increased collateral ventilation taking place in the diseased lung. There remains a need for a medical procedure that can alleviate some of the problems caused by COPD. There is also a need for a medical procedure that alleviates some of the problems caused by COPD irrespective of whether a portion of the lung, or the entire lung is emphysematous. The production and maintenance of collateral openings through an airway wall allows oxygen depleted/carbon dioxide rich air to pass directly out of the lung tissue responsible for gas exchange. These collateral openings ultimately decompress hyper inflated lungs and/or facilitate an exchange of oxygen into the blood.

SUMMARY OF THE INVENTION

This invention relates to devices and methods for altering gaseous flow in a diseased lung. In particular, the inventive method includes the act of improving gaseous flow within a diseased lung by the step of altering the gaseous flow within the lung. A variation of the inventive method includes the act of selecting a site for collateral ventilation of the diseased lung and creating at least one collateral channel at the site. The term "channel" is intended to include an opening, cut, slit, tear, puncture, or any other conceivable artificially created opening. A further aspect of the invention is to locate a site within a portion of a natural airway of the respiratory system of the patient having the diseased lung. The portion of the natural airway selected for the creation of the collateral channels may be, for example, the bronchi, the upper lobe, the middle lobe, the lower lobe, segmental bronchi and the bronchioles.

A variation of the invention includes selecting a site for creating a collateral channel by visually examining areas of collateral ventilation. One variation includes visually examining the lung with a fiber optic line. Another example includes the use of non-invasive imaging such as x-ray, ultrasound, Doppler, acoustic, MRI, PET computed tomography (CT) scans or other imaging. The invention further includes methods and devices for determining the degree of collateral ventilation by forcing gas through an airway and into air sacs, reducing pressure in the airway, and determining the reduction in diameter of the airway resulting from the reduction in pressure. The invention further includes methods and devices for determining the degree of collateral ventilation by forcing a volume of gas within the lung near to the airway and measuring pressure, flow, or the return volume of gas within the airway. The invention also includes methods and devices for occluding a section of the airway and determining the degree of collateral ventilation between the occluded section of the airway and the air sacs.

An important, but not necessarily critical, portion of the invention is the step of avoiding blood vessels or determining the location of blood vessels to avoid them. It is typically important to avoid intrapulmonary blood vessels during the creation of the collateral channels to prevent those vessels from rupturing. Thus, it is preferable to avoid intrapulmonary or bronchial blood vessels during the creation of the collateral channels. Such avoidance may be accomplished, for example by the use of non-invasive imaging such as radiography, computed tomography (CT) imaging, ultrasound imaging, Doppler imaging, acoustical detection of blood vessels, pulse oxymetry technology, or thermal detection or locating. The avoidance may also be accomplished using Doppler effect, for example transmission of a signal which travels through tissue and other bodily fluids and is reflected by changes in density that exist between different body tissue/fluids. If the signal is reflected from tissue/fluid that is moving relative to the sensor, then the reflected signal is phase shifted from the original signal thereby allowing for detection.

Another variation of the inventive device includes a device that detects motion within tissue using Doppler measurements. The device may include a flexible member having a transducer assembly that is adapted to generate a source signal and receive a reflected signal. The transducer assembly may include an acoustic lens which enables the transmission and detection of a signal over a tip of the device.

Another variation of the invention includes marking the site after it is located. Accordingly, once marked, a previously selected site can be located without the need to re-examine the surrounding area for collateral ventilation, or the presence or absence of a blood vessel. The marking may be accomplished by the deposit of a remotely detectable marker, dye, or ink. Or, the marking may comprise making a physical mark on the surface of the airway to designate the site. Preferably, the mark is detectable by direct visualization or such imaging methods as radiography, computer tomography (CT) imaging, ultrasound imaging, doppler imaging, acoustical detection, or thermal detection or locating.

The invention may also include a user interface which provides feedback once an acceptable site is located. For example, once a site is located a visual or audible signal or image is transmitted to the user interface to alert the user of the location of a potential site. The signal could be triggered once a blood vessel is located so that the site is selected in another location. In another example, the signal may trigger so long as a blood vessel is not located.

The invention may include adding an agent to the lungs for improving the imaging. For example, a gas may be inserted into the lungs to provide contrast to identify hyperinflation of the lungs during an x-ray or other non-invasive imaging. For example, $^{133}$Xe (Xenon 133) may be used as the agent. Also, a contrast agent may help in identifying blood vessels during CT scans. Another example includes inserting a fluid in the lungs to couple an ultrasound sensor to the wall of an airway.

The invention may also include providing a remotely detectable signal to indicate the presence or absence of any blood vessels at the target site. The invention also includes methods and devices for marking a desired site for the creation of a collateral channel.

The invention also includes the act of creating one or more collateral channels within the respiratory system of the individual. The collateral channels may have a cross sectional area anywhere between 0.196 mm$^2$ to 254 mm$^2$. Any subset of narrower ranges is also contemplated. The collateral channels may also extend anywhere from immediately beyond the epithelial layer of the natural airway to 10 cm or more beyond the epithelial layer. The channel or channels should be created such that the total area of the channel(s) created is sufficient to adequately decompress a hyperinflated lung. The channel may be, for example, in the shape of a hole, slit, skive, or cut flap. The channel may be formed by the removal of any portion of the airway wall; e.g., a circumferential or arc-shaped ring of material may be removed to form the channel. Such an excised periphery may be for example, perpendicular or angled with respect to the axis of the airway.

Also, it is anticipated that along with any method of creating a collateral channel any loose material or waste generated by the creation of the collateral channel is optionally removed from the airway.

Another variation for creating the collateral channel is the creation of the airway using electric energy, for example radio frequency. Or, for example, ultrasonic energy, a laser, microwave energy, chemicals, thermal, or cryo-ablative energy may be used to form a collateral channel as well. A feature of these methods often includes creation of a hemostasis in the event that any blood vessel is punctured. For example, use of RF energy provides a hemostasis given a puncture of a vessel by using heat to seal the vessel. Similarly, an ultrasonic scalpel also provides an area of hemostasis in case the vessel is punctured. It is understood that any combination of different methods may be used for forming a single or multiple collateral channels. A variation of the invention includes a limiter for limiting the depth of a collateral channel.

Another variation of the inventive device includes combining the doppler catheter described above with a hole-making assembly that is adapted to form collateral channels within tissue. The hole-making assembly may be an RF device and use portions of the tip of the device as RF electrodes, or the hole-making assembly may use ultrasound energy to make the hole. Alternatively, the hole-making assembly may be the transducer assembly described above which may be operated at an intensity which causes the transducer assembly to function as a hole-making device.

Another variation of the invention includes the act of inserting an implant or conduit within a collateral channel to maintain the patency of the channel over time during the expiration cycle of the lung. A conduit could, for example, have distal and proximal ends with a wall defining a lumen extending between the ends. The conduit could have, for example, a porous wall permitting the exchange of gasses through the wall. The conduit may, for example, be comprised of a material such as elastomers, polymers, metals, metal alloys, shape memory alloys, shape memory polymers, or any combination thereof. A variation of the invention includes an expandable conduit, either one that is self-expanding, or one that expands in diameter in relation to any applied radial, or axial force. For example, the conduit may be expanded into an opening of the natural airway upon the inflation of a balloon. A variation of the conduit may include the use of flanges or anchors to facilitate placement of the device within an airway. Another variation of the conduit includes placing a one-way valve within the conduit. Another variation includes using a self cleaning mechanism within the conduit to clear accumulating debris.

The invention includes the method of feeding a guidewire to a site within the lung, advancing a conduit to the site using the guidewire, and placing the conduit within the lung tissue at the site. The method may include inserting an access device, such as a bronchoscope, within airways of the lung to locate a site within the lung for creation of the collateral channel. The access device could also be used as an access device so that the required devices may be introduced to the site. A catheter having a conduit attached thereto may be advanced over the guide-wire for insertion of the conduit within the collateral channel.

The inventive conduit may be, for example, removable or permanent. Also, another variation of the device includes a means for inserting the conduit within a collateral channel. The conduit may be constructed to allow for passage of gasses through its wall, for example, the conduit may have a wall consisting of a braid. A variation of the conduit may be located through an opening in a wall of an airway and engage both an inside and outside of the wall. Another variation of the conduit includes a distal end having a porous member and a proximal end having a grommet member which engages an opening in a wall of the natural airway. Yet another variation of the implant, for example, comprises an expandable conduit-like apparatus which could bridge an opening within a wall of a natural airway. Another variation includes the conduit-like apparatus having a cutting portion exterior to the device wherein expansion of the device pierces the wall of the natural airway and creates a collateral channel.

An aspect of the invention is that conduits of varying cross-sectional areas may be placed in various sections of the lung to optimize the effect of the collateral channels.

Another variation of the invention includes the application of a cyano-acrylate, fibrin or other bio-compatible adhesive to maintain the patency of a collateral channel. The adhesive may be used with or without the conduit described above. For example, the adhesive may be deposited within the collateral channel to maintain patency of the channel or to create a cast implant of the channel. The inventive act further includes the act of delivering medications such as steroids which have been shown to inhibit the healing process, bronchodilators, or other such drugs which aid in breathing, fighting infection, or recovery from the procedure. The steroids inhibit inflammation and then promote the stabilization of the created channel.

Another variation of the inventive process includes promoting the flow of gasses through under-utilized parenchymal inter-conduits, or bypassing restricted airways. It is also contemplated that the gaseous flow may be altered by, for example, making separate inspiratory and expiratory paths. Also, relieving pressure on the external wall of a natural airway may be accomplished to assist the natural airway by maintaining patency during the expiration cycle of the lung. Yet another variation includes creating collateral channels parallel to existing airflow paths, or the existing airflow paths may be increased in cross-sectional area.

The invention further includes a modified respiratory airway having an artificially created channel allowing gaseous communication between an exterior of the airway and an interior of the airway.

The invention may include an endoscope or a bronchoscope configured to select sites and create collateral channels at those sites. An endoscope or a bronchoscope may also be configured to deploy conduits within the collateral channels. Another variation of the invention includes sizing the device to fit within the working channel of a bronchoscope.

The invention also includes methods for evaluating an individual having a diseased lung for a procedure to create collateral channels within an airway of the individual. The invention further includes the method of determining the effectiveness of the procedure.

The invention further includes the act of teaching or providing instructions for any of the methods described herein or for using any of the devices describe herein.

The invention further includes the method of sterilizing any of the devices or kits described above.

BRIEF DESCRIPTION OF THE DRAWINGS

FIGS. 1A–1C illustrates various states of the natural airways and the blood-gas interface.

DETAILED DESCRIPTION OF THE INVENTION

Figure 1D:
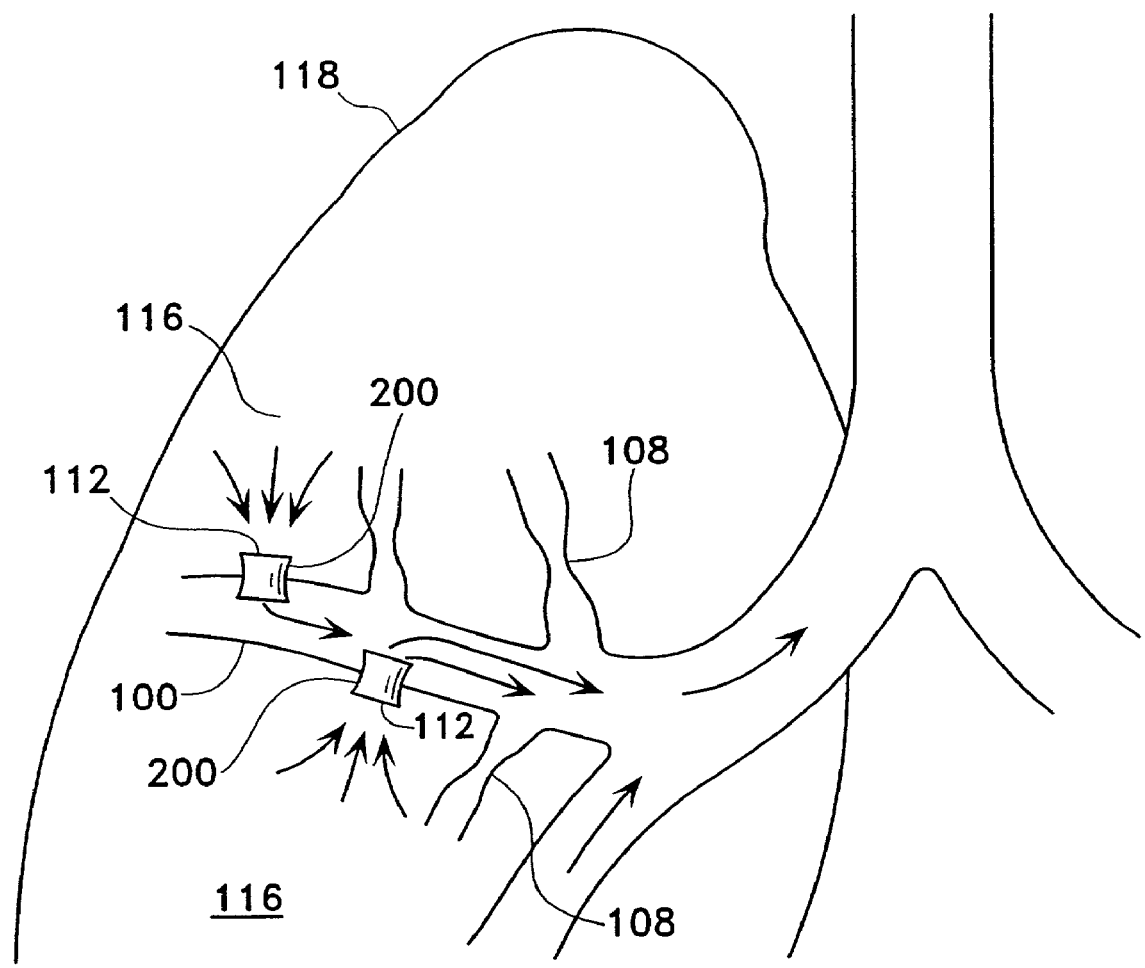
FIG. 1D illustrates a schematic of a lung demonstrating a principle of the invention described herein.

Prior to considering the invention, simplified illustrations of various states of a natural airway and a blood gas interface found at a distal end of those airways are provided in FIGS. 1A–1C. FIG. 1A shows a natural airway 100 which eventually branches to a blood gas interface 102. FIG. 1B illustrates an airway 100 and blood gas interface 102 in an individual having COPD. The obstructions 104 impair the passage of gas between the airways 100 and the interface 102. FIG. 1C illustrates a portion of an emphysematous lung where the blood gas interface 102 expands due to the loss of the interface walls 106 which have deteriorated due to a bio-chemical breakdown of the walls 106. Also depicted is a constriction 108 of the airway 100. It is generally understood that there is usually a combination of the phenomena depicted in FIGS. 1A–1C. More usually, the states of the lung depicted in FIGS. 1B and 1C are often found in the same lung.

The following illustrations are examples of the invention described herein. It is contemplated that combinations of aspects of specific embodiments or combinations of the specific embodiments themselves are within the scope of this disclosure.

As will be explained in greater detail below, central to this invention in all of its aspects is the production and maintenance of collateral openings or channels through the airway wall so that oxygen depleted/carbon dioxide rich air is able to pass directly out of the lung tissue and into the airways to ultimately facilitate exchange of oxygen into the blood and/or decompress hyper inflated lungs. The term 'lung tissue' is intended to include the tissue involved with gas exchange, including but not limited to, gas exchange membranes, alveolar walls, parenchyma and/or other such tissue. To accomplish the exchange of oxygen, the collateral channels allow fluid communication between an airway and lung tissue. Therefore, gaseous flow is improved within the lung by altering or redirecting the gaseous flow within the lung, or entirely within the lung. FIG. 1D illustrate a schematic of a lung 118 to demonstrate a principle of the invention described herein. As shown, a collateral channel 112 places lung tissue 116 in fluid communication with airways 100 allowing oxygen depleted/carbon dioxide rich air to directly pass out of the airways 100. The term channel is intended to include an opening, cut, slit, tear, puncture, or any other conceivable artificially created opening. As shown, constricted airways 108 may ordinarily prevent air from exiting the lung tissue 116. In the example illustrated in FIG. 1D, conduits 200 may be placed in the collateral channels 112 to assist in maintaining the patency of the collateral channels 112. Therefore, it is not necessary to pierce the pleura to improve gaseous flow within the lungs. While the invention is not limited to the number of collateral channels which may be created, it is preferable that 1 or 2 channels are placed per lobe of the lung. For example, the preferred number of channels is 2–12 channels per individual patient.

Accordingly, since the invention is used to improve the function of the lungs, a variation of the inventive device may include an endoscope or a bronchoscope configured to locate a site for creating a collateral channel and create the collateral channel. Another variation includes sizing the inventive device to fit within a working channel of an endoscope or a bronchoscope. For the sake of brevity, hereafter, any reference made to an endoscope includes the term bronchoscope.

The invention includes assessing the degree of the collateral ventilation taking place in an area of a lung to select a site for creation of a collateral channel. The invention may include locating a site for creation of a collateral channel by visually examining an airway for dynamic collapse. One method of visual examination includes the use of a fiber optic line or camera which may be advanced into the lungs and through the airways. Other variations of visually examining the lung to determine the location of a site for the creation of the collateral channel using non-invasive imaging, including but not limited to radiography, computer tomography, ultrasound, Doppler, and acoustic imaging. Such imaging methods may also be used to determine the amount of collateral channels to be created.

Also contemplated in the invention is the addition of various agents to assist during imaging of the airways or lungs. One example includes the use of a non-harmful gas, such as Xenon, to enhance the visibility of hyperinflated portions of the lung during radiological imaging. Another example includes the use of inserting a fluid in the lungs to provide an improved sound transmission medium between the device and the tissue in variations of the invention using ultrasound, acoustic, or other imaging.

Another variation of the invention includes methods and devices for triggering a collapse of the airway to determine the degree of collateral ventilation in the lung. One example includes forcing a fluid, such as a gas, air, oxygen, etc., through the airway and into the air sacs. Next, to assess the patency of the airway, the pressure is reduced in the airway. One example of how pressure is reduced in the airway includes evacuating the air in a direction opposite to the air sacs. Constriction of the airway given a drop in pressure may be an indication of collateral ventilation of the lung in that region.

Figure 2A:
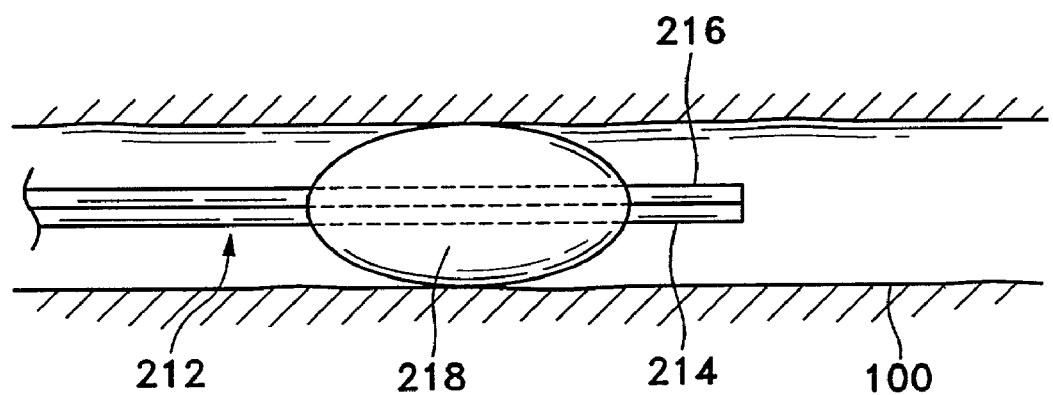
FIGS. 2A–2C illustrate devices and methods for determining the degree of collateral ventilation within a lung.

FIG. 2A, illustrates a method and device 212 for causing collapse of the airway wall 100. The device 212 includes a fluid delivery member 214 located at a distal end of the device 212. The fluid delivery member 214 is configured to deliver a volume of fluid through the airway 100 and into an air sac (not shown). The device 212 may also comprise a probe 216 configured to collect data within the lung. The probe 216 may also simply consist of a channel that transmits signals outside of the lung. Moreover, the fluid delivery member 214 and the probe 216 may not be separate channels. Also, the device 212 may, but does not necessarily, have an occlusion member 218 designed to isolate a section of the airway 100 between the occlusion member 218 and the air sacs (not shown). The occlusion member 218, which forms a seal against the airway 100 walls, may provide a partially closed system allowing a more effective search for collateral ventilation between the air sacs (not shown.) The device delivers a burst of fluid, through the fluid delivery member 214 and subsequently uses the probe 216 to measure characteristics such as pressure, flow, or return volume to determine the degree of collateral ventilation. The term fluid is intended to include, air or a gas, such as oxygen, etc. For example, if the air sacs are diseased (as shown in FIG. 1C), the forced fluid will escape/disperse through another air sac due to the collateral ventilation of the air sacs. As a result, the probe 216 may fail to record any increase in pressure, volume, flow, or any other characteristic of the fluid at the site. Another variation of the invention includes using the fluid delivery member 214 to add or remove fluid distally to the occluded segment and using the probe 216 to monitor flow or pressure changes in the area. For example, if after adding/removing fluid the pressure in the occluded segment fails to build/drop, the assumption may be made that the gas is being collaterally vented through diseased air sacs.

Figure 2B:
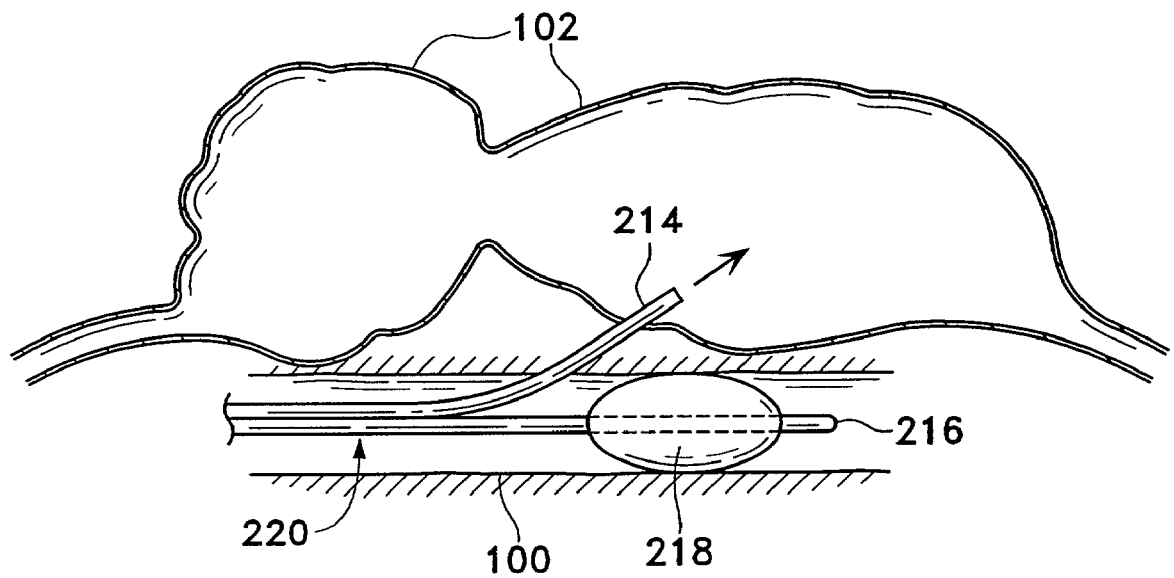

FIG. 2B illustrates another variation of the invention. In this example, the device 220 comprises a separated probe 216 and gas delivery member 214. In this variation, the fluid delivery member 214 is configured to pass through a wall of the airway 100 so that fluid may be directly forced into, or pulled out of an air sac 102.

Figure 2C:
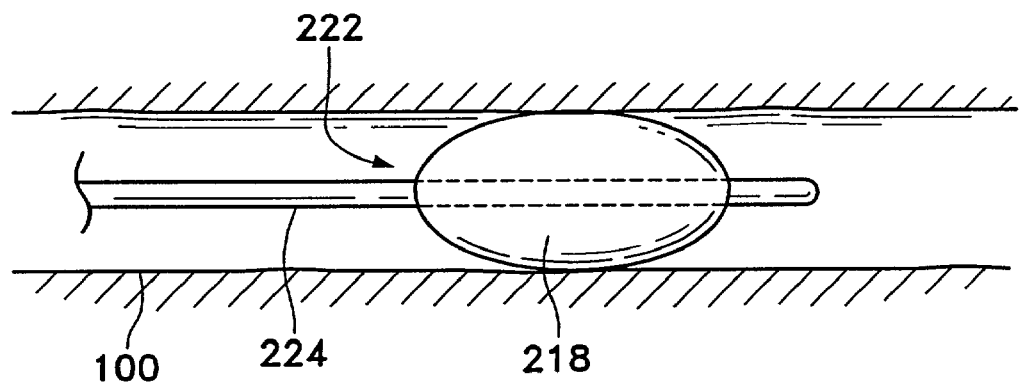

FIG. 2C illustrates yet another variation of the invention. In this variation, the device 222 may have at least one fluid exchange passageway 224. The device 222 may force fluid into the airway 100 via the passageway 224. Then, fluid can be pulled out via the passageway 224, thus decreasing pressure distally to the device 222. The decrease in pressure permits fluid to flow out of the airway 100 and away from the air sac (not shown). In this case, if the air sacs surrounding the airway 100 are diseased and collateral ventilation is taking place, then the airway 100 may collapse. A variation of the invention may include an expandable member 218, such as a balloon, to create a seal against the airway 100 walls. Forming a seal may provide a partially closed system to search for collateral ventilation between air sacs (not shown.) As described above, observation of a collapsing airway 100 may indicate a desired site for creation of a collateral channel.

FIGS. 3A–3I depict various ways of providing openings in the airway wall which may be used as collateral air passageways.

Figure 3A:
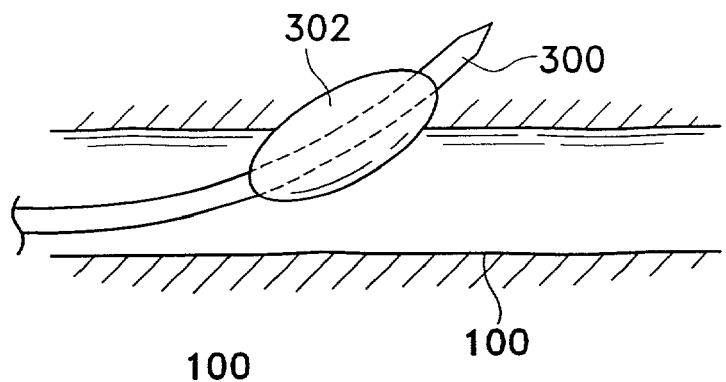
FIGS. 3A–3P illustrate methods of and devices for creating a collateral opening within a natural airway.

FIG. 3A illustrates an airway 100 having a piercing member 300 and a dilation member 302. In this example, the piercing member 300 makes an incision (not shown) in the airway 100 wall. Next, the piercing member 300 is advanced into the wall so that a dilation member 302 can expand the incision to thereby provide a collateral channel. In this example, the dilation member 302 is depicted as a balloon. One variation of the invention includes filling a balloon with a heated fluid as the balloon dilates the tissue to form the collateral channel. Use of a heated balloon allows the transfer of heat to the collateral channel for modifying the healing response. However, it is also contemplated that the dilation member may be an expanding wedge (not shown) or other similar device.

Figure 3B:
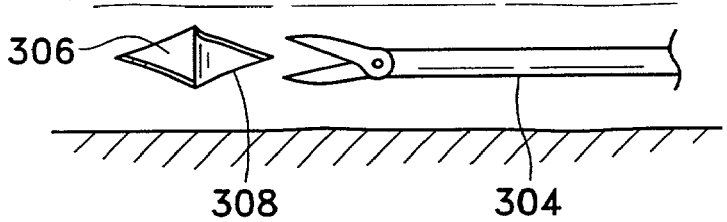

FIG. 3B shows a cutting device 304 and an airway 100 having an opening 306 cut from a wall. In this example, a flap 308 is cut from the wall and is attached to an outside or an inside wall of the airway 100. As will be mentioned below, the flap may be glued, using for instance, fibrin-based or cyano-acrylate-based glues or stapled to that wall.

Figure 3C:
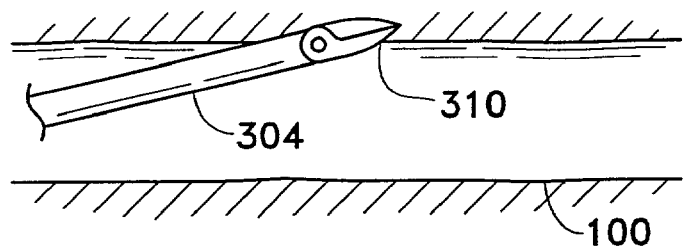
Figure 3D:
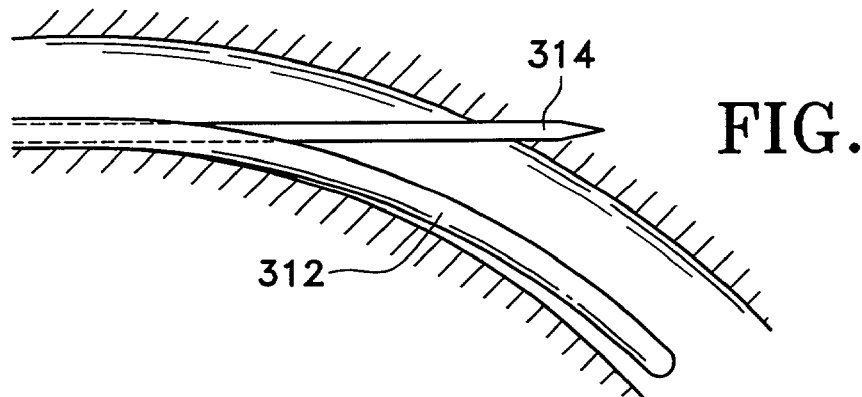

FIG. 3C illustrates a cutter 304 making an incision 310 in a wall of the airway 100. FIG. 3D illustrates one example of placing the walls of the airway 100 in tension and inserting a blunt instrument 314 into the incision. In this example, the delivery device 312 is flexible and maybe shaped to the contour of an airway 100 to provide support for the blunt instrument 314 so that the instrument 314 can advance into the incision. The delivery device 312 is also used to deliver a blunt instrument 314 which expands the original incision. The blunt instrument 314 may have a hooked configuration as needed.

Figure 3E:
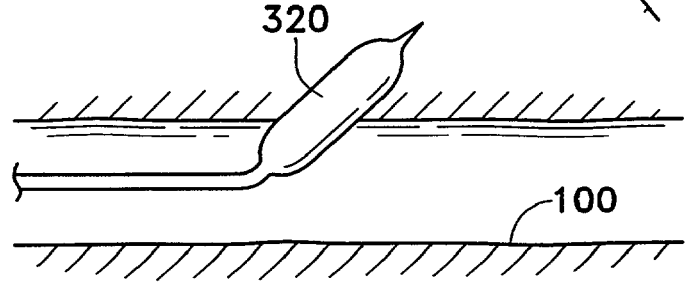

FIG. 3E shows the use of a balloon 320 to dilate a previously formed collateral channel in the airway wall 100. This procedure may be used variously with other mechanical, chemical, cryo-energy, thermal or RF based penetration systems to expand the size of that previously-formed opening. It should be noted, that variations of the inventive device described herein using energy to create a collateral channel will require a power supply to be coupled to the active heating element. For sake of convenience, the power supply is not always illustrated in the Figures.

Figure 3F:
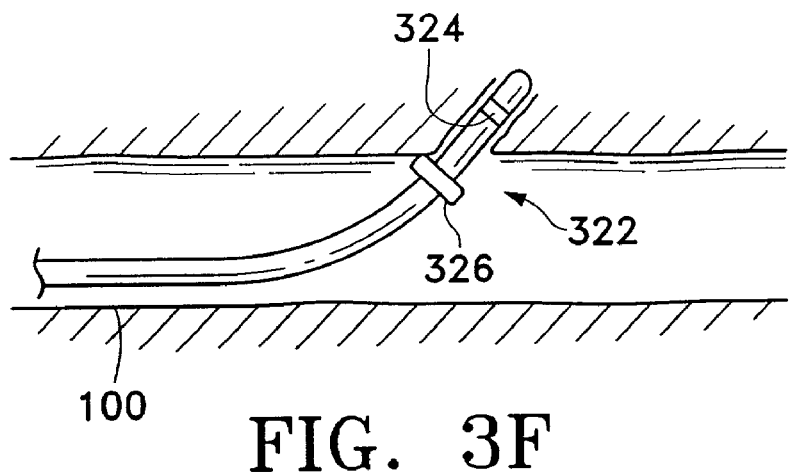
Figure 3G:
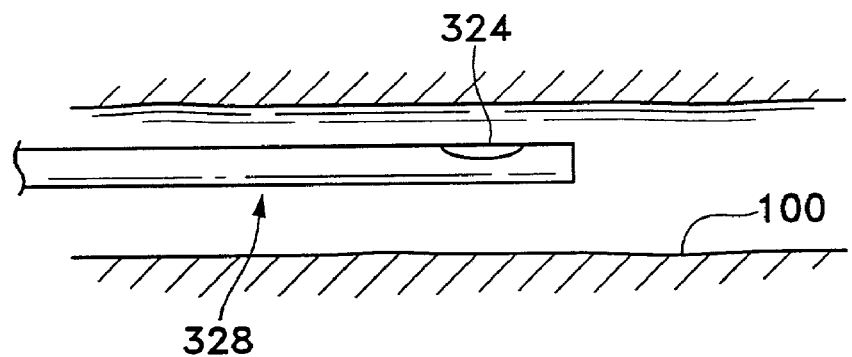
Figure 3H:
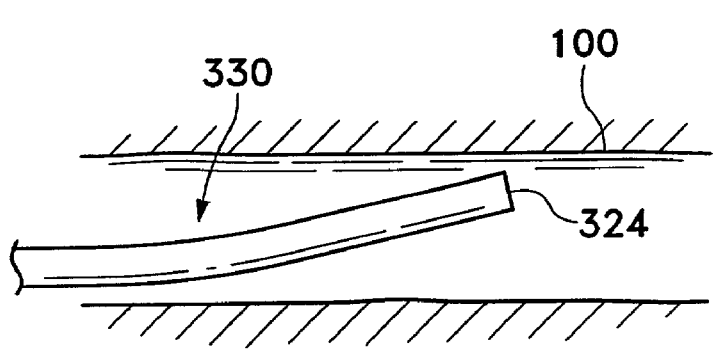
Figure 3I:
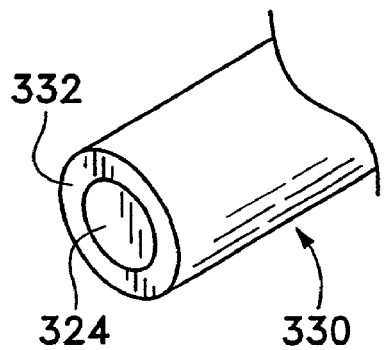

FIG. 3F illustrates a variation of the device 322 having an RF electrode 324. This variation of the invention uses RF energy to create a collateral channel. The device 322 may be mono-polar or bi-polar. The RF energy throughout this invention is similar to that of a typical RF cutting probe operating between the 300 KHz–600 KHz range. FIGS. 3G–3I illustrates additional variations of devices of the present invention used to create collateral channels. The devices may use RF energy, either monopolar or bipolar, or the devices may use light, infrared heat, or any of the other methods describe herein. In the variation of FIG. 3G, the device 328 has an electrode 324 located on a side of the device. This variation of the device 328 automatically limits the depth of the collateral channel as the body of the device 328 remains against an airway 100 wall while the electrode 324 creates a channel.

FIGS. 3H and 3I illustrates another variation of a device 330 of the present invention having an electrode 324 located on a front face of the device. FIG. 3I illustrates a perspective view of the device 330 with an electrode on the front face 324. The device 330 may either have an electrode 324 disposed on a front surface of the device 330 or the device may comprise a conductive material with an insulating layer 332 covering the device 330 and leaving an electrode surface 324 exposed. In the variations illustrated in FIGS. 3G–3I, the size of the electrode may be selected based upon the size of the desired collateral channel.

The device of the present invention may also be configured to limit the depth of the collateral channel. In one example, FIG. 3F, the invention may include a shoulder or stop 326 to limit the depth of the collateral channel. Another example includes graduated index markings on a proximal end of the device or on the distal end so long as they are remotely detectable. Also contemplated is the use of RF impedance measuring. In this example, the use of RF impedance may be used to determine when the device leaves the wall of the airway and enters the air sac or less dense lung tissue.

Figure 3J:
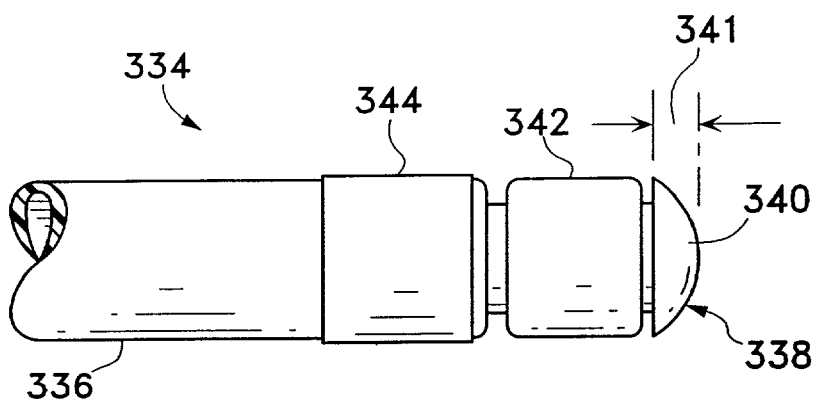

FIG. 3J illustrates another variation of a device 334 of the present invention adapted to create collateral channels. In this variation, the device 334 includes an elongate body 336 which may have a lumen extending therethrough. The device 334 further includes a heating element 338 extending from the elongate body 336. The heating element described herein for the variations of the invention may be the type which actually generates heat in the element, such as, for example, a resistive heating element. Furthermore, the heating element described herein for the variations of the invention may be the type which actually generates heat directly within the tissue, for example, an RF electrode. In any case, the heating element of the present invention shall have a heating surface located on the front surface of the heating element that is adapted to minimize heat in a radial direction from the heating element. Accordingly, the heating element will preferably be a cone, hemispherical, or similar member that is shallow in depth. In one variation, the heating surface will have a depth (as illustrated by depth 341 in FIG. 3J) which is less than the diameter of the heating surface. For example, the depth could be less than the radius of the heating surface. As a result of this configuration, heat generated by the heating element is directed towards creating channels or holes. Minimizing heat in a radial direction from the heating element prevents excessive heating of the walls of the collateral channel or hole within the tissue.

The heating element 338 shown in FIG. 3J includes a heating surface 340 which is located over the front surface of the heating element 338. The heating element 334 may be any type of heat generating device described herein and is coupled to its respective power supply. In one variation, the heating element 338 comprises an RF electrode. In such a case, the heating element 338 is coupled to an RF generator (not shown). Although not illustrated, a variation of the device includes a heating element which extends through the lumen of the elongate member. The heating element may extend throughout the elongate member or it may extend partially into the elongate member.

The variation of the devices described herein may also include insulating surfaces. For example, in FIG. 3J, the device 334 may have at least one insulating surface 342 located adjacent to the heating surface 340. The insulating surface 342 shields tissue from heat generated by the heating element 338 as the heating element 338 creates a collateral channel in tissue. The insulating surfaces described herein may be configured to shield tissue from heat generated by the heating element, or, the insulating surface may prevent heat from being generated in the tissue which is adjacent to the insulating surface (e.g., in an RF hole-making device). Each of these materials is selected to have sufficient properties (e.g., low thermal conductivity, non-conductive, etc.). An insulating surface may comprise a ceramic material, such as alumina oxide, zirconia oxide, silicon nitride, silicate, etc. The insulating surface may also comprise a plastic tubing such as Nylon, polyimide, PTFE, Pebax, etc. Other examples include insulating surfaces comprising, for example, an epoxy, or a bio-compatible coating such as paralene. Alternatively, the insulating surface may comprise a combination of the above listed materials. As discussed above, it is noted, that the device may be used without an insulating surface 342.

Figure 3K:
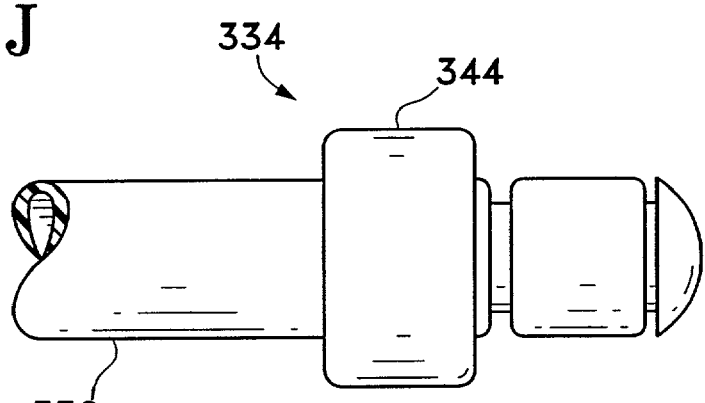

The device 334 may further include a shoulder 344 located on the elongate body 336 and proximate to the heating element 338. The shoulder 344 is configured to expand to a diameter greater than a diameter of the elongate body 336. Accordingly, the shoulder 334 serves as a stop or depth limiter for the device 334 as it creates a collateral channel. In the variation illustrated in FIG. 3J, the shoulder 344 comprises a balloon, which has a reduced profile (illustrated) and an expanded profile. FIG. 3K illustrates the balloon 344 in the expanded profile. The maximum diameter of a shoulder used in any variation of the invention described herein may vary depending upon the application. Currently, it is believed that a shoulder should be greater than 3 mm in diameter. The balloon may be constructed from silicone, urethane, or other such materials. The elongate member of the variations describe herein may be comprised of a nylon, polyethylene, polycarbonate, etc., or a combination thereof.

It is noted that a variation of the device of the present invention may have a shoulder 344 comprised of other than a balloon, but is simply a structure which has a diameter greater than a diameter of a heating element on the device. In such a case, referring to the illustration of FIG. 3K, the shoulder 344 would not be adjustable in a radial direction from the elongate member 336.

Figure 3L:
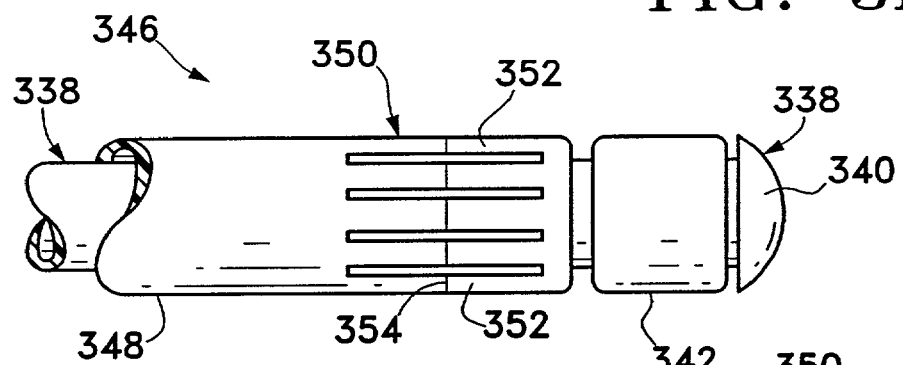

FIG. 3L illustrates another variation of a device 346 of the present invention adapted to create collateral channels. In this variation, the device 346 includes an elongate body 348 which may have a lumen extending therethrough. The device 346 further includes a heating element 338 extending from the elongate body 348. Wherein the heating element 338 includes a heating surface 340 which may be located over the front surface of the heating element 338. As described above, the heating element 338 may be any type of heat generating device described herein and is coupled to its respective power supply. In one variation, the heating element 338 comprises an RF electrode. In such a case, the heating element 338 is coupled to an RF generator (not shown).

The variation of the device 346 illustrated in FIG. 3L may also includes an insulating surface 342 located adjacent to the heating surface 340. The insulating surface 342 shields tissue from heat generated by the heating element 338 as the heating element 338 creates a collateral channel in tissue.

Figure 3M:
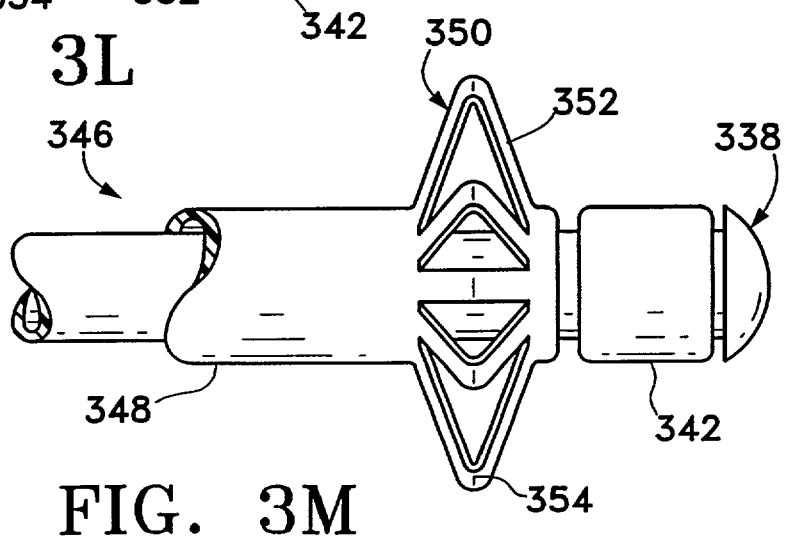

The device 346 of FIG. 3L further includes a shoulder 350 located on the elongate body 348 and proximate to the heating element 338. As described above, the shoulder 350 is configured to expand to a diameter greater than a diameter of the elongate body 348 allowing the shoulder 350 to serve as a stop or depth limiter for the device 346 as it creates a collateral channel. In the variations illustrated in FIGS. 3L and 3M, the shoulder 350 is comprised of a plurality of hinged members 352 each of which is adapted to expand in diameter from the expandable member 348. In this variation, the hinged members 352 each have a living hinge 354 which allows the hinged members 352 to assume an expanded or reduced profile. In the variation depicted in FIGS. 3L and 3M, the hinged members 352 expand away from the elongate member 348 given relative movement between the elongate member 348 and the heating element 338. For example, as illustrated in FIG. 3M, the heating element 338 may be pulled in a proximal direction against the elongate member 348 causing the insulating surface 342 to force the hinged members 352 outwardly. As a result, the shoulder 350 assumes an expanded profile. Although the hinged members 352 are illustrated as being parallel to the lumen of the elongate member 348, the invention is not limited as such. Moreover, the number of hinged members 352 is not limited to that which is illustrated. It is contemplated that variations of the inventive device may include 2 or more hinged members.

In the devices illustrated in FIGS. 3J–3M, although the heating element is depicted as being spaced from the elongate member, the invention is not limited as such. For example, in variations where the heating element is not slidably located in the elongate member, a device may have a gap between the heating element and the elongate member such that the insulating surface is against or within the elongate member. Moreover, the device may be designed to have a pre-determined gap between the insulating surface and the elongate member. Alternatively, for any of the variations described herein, there may be no gap between the insulating surface and the elongate member.

Figure 3O:
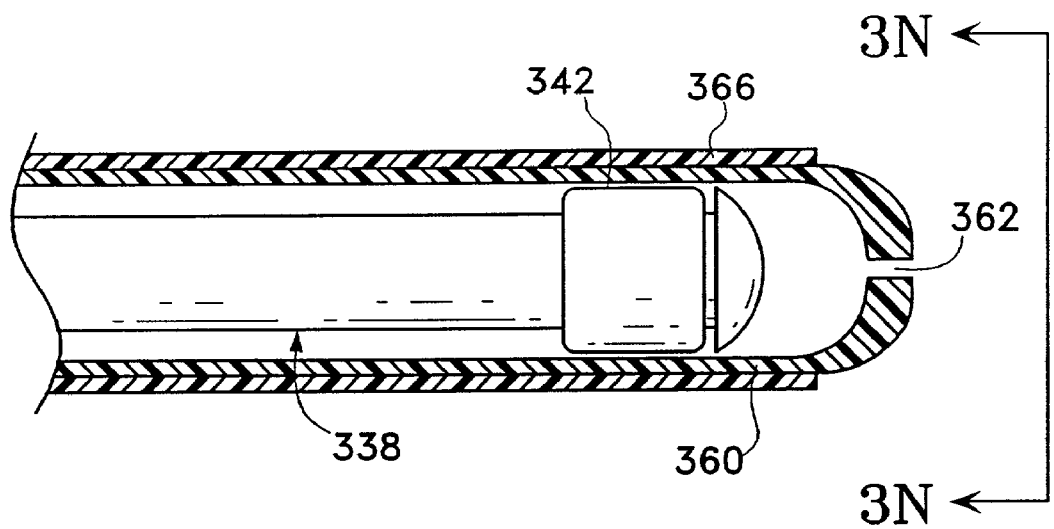
Figure 3N:
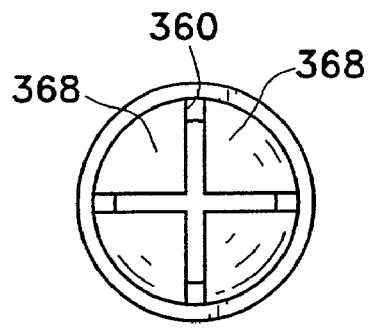
Figure 3P:
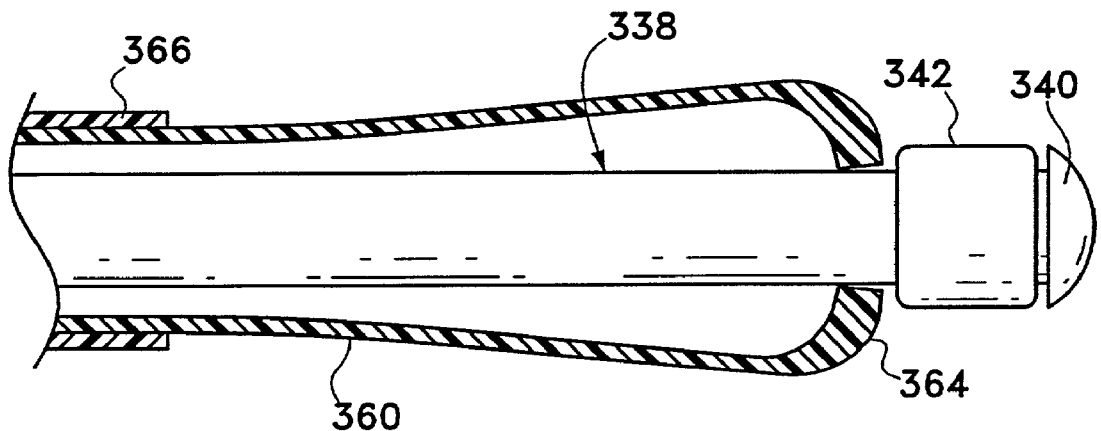

FIGS. 3N-3P illustrate another variation of the inventive device which is adapted to create collateral channels. In this variation, the heating element 338 is moveably located within an elongate member 360. At least a portion of the lumen of the elongate member 360 has a reduced opening 362 which is smaller than a diameter of the heating element 338. As shown in FIG. 3P, a distal end of the elongate member 360 may be radially adjustable to permit the heating element 360 to move in and out of the lumen. In the variation of the device depicted in FIG. 3P, the front surface of the elongated member 360 functions as a shoulder 364 when the heating element 338 extends from the front of the elongated member 360. The distal end of the elongated member 360 may be remotely actuated to expand, or, the distal end may be biased to expand outwardly. In the latter case, the distal end may be restrained, for example, by an outer tubular member 366. The outer tubular member 336 may also be used to reduce the diameter of the distal end to close against the heating element 338, as shown in FIG. 3P. The distal end of the elongated member 360 may be a continuous tubular structure which expands in diameter, or it may be a tubular structure that divided into any number of portions which permit the radial expansion of the distal end. For example, FIG. 3N illustrates a front view of the device of FIG. 3O in which at least a segment of the elongated member 360 is divided into four portions 368 so that it may be radially adjustable. It is understood that the number of portions 368 illustrated are merely exemplary, as the number may be varied as needed. Furthermore, the elongated member 360 may not be divided into any such portions 368 and instead may be an expandable elastic member comprised of, for example: silicone, urethane, etc.

Figure 4A:
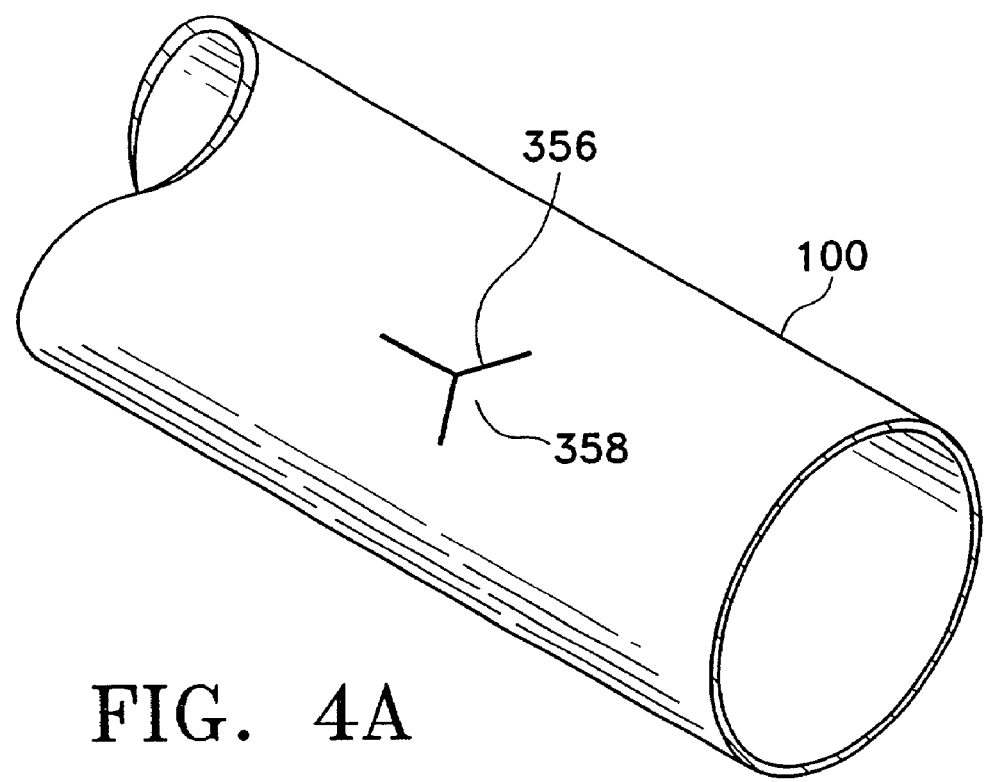
FIGS. 4A–4B illustrate a method of folding epithelial tissue through a collateral channel.
Figure 4B:
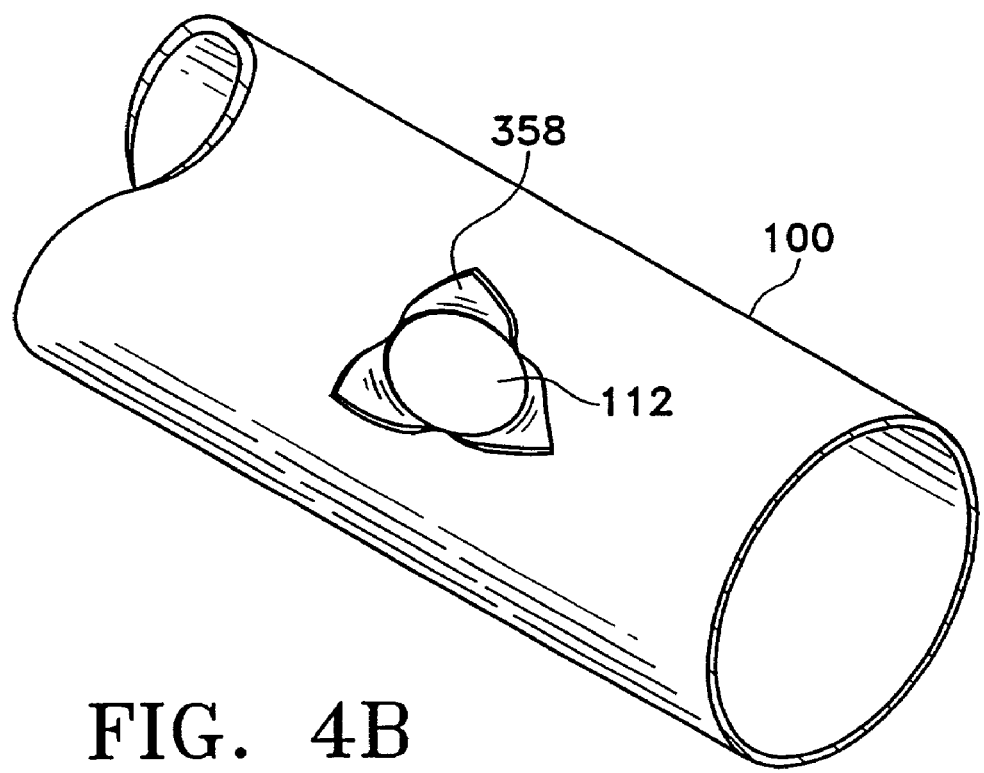

The invention also includes creating a collateral channel by making a single or a series of incisions in an airway wall then folding back the cut tissue through the collateral channel. This procedure allows the surface epithelium which was previously on the inside of the airway wall to cover the walls of the newly formed collateral channel. As discussed herein, promoting growth of the epithelium over the walls of the collateral channel provides a beneficial healing response. The incision may be created by the use of heat or a mechanical surface. For example, FIG. 4A illustrates a section of an airway 100 having several incisions 356 forming a number of sections 358 of airway wall tissue the airway 100. FIG. 4B illustrates the sections or flaps 358 of the airway wall folded through the collateral channel 112. Any number of incisions 358 may be made to form any number of sections 358 of airway wall tissue as desired. For example, a plus-shaped incision would result in four sections of tissue that may be folded through a channel. The sections 358 may be affixed with a suture material, an adhesive, or the sections 358 may simply be inserted into surrounding tissue to remain folded through the collateral channel 112.

Another variation of the device includes safety features such as probes to determine the presence of blood. If a probe indicates that a blood vessel is contacted or penetrated, a signal is sent which prevents the channel making device from causing further harm to the vessel. Such a feature minimizes the risk of inadvertently puncturing a blood vessel within the lungs.

Although the examples depict mechanically forming a collateral opening, the invention is not limited to such. Alternative methods of forming the opening are contemplated in the use of RF energy, bi-polar, or single pole electrosurgical cutters, ultrasonic energy, laser, microwave, cryo-energy, thermal, or chemicals.

Another variation of the invention includes methods and devices for determining whether a blood vessel is in proximity to a potential site. Making this determination prior to creating the channel is advantageous as the risk of puncturing a blood vessel is minimized. It is important that the devices of the present invention do not 'wander' resulting in the creation of a collateral channel at a distance from the area originally searched. Such an occurrence may compromise a blood vessel (e.g., puncture, rupture, or otherwise open the blood vessel) even though the step of detecting the location indicated the absence of a blood vessel. In those cases, a device having a stiffer wall provides added benefits. Accordingly, the devices must be flexible to navigate to a target site, yet once they reach the target site the device should be configured to minimize subsequent movement.

The present invention includes the use of a device which is able to detect the presence or absence of a blood vessel by placing a front portion of the device in contact with tissue. One variation of the invention includes the use of Doppler ultrasound to detect the presence of blood vessels within tissue. It is known that sound waves at ultrasonic frequencies travel through tissue and reflect off of objects where density gradients exist. In which case the reflected signal and the transmitted signal will have the same frequency. Alternatively, in the case where the signal is reflected from the blood cells moving through a blood vessel, the reflected signal will have a shift in frequency from the transmitted signal. This shift is known as a Doppler shift. Furthermore, the frequency of the signals may be changed from ultrasonic to a frequency that is detectable within the range of human hearing.

The ultrasound Doppler operates at any frequency in the ultrasound range but preferably between 2 Mhz–30 Mhz. It is generally known that higher frequencies provide better resolution while lower frequencies offer better penetration of tissue. In the present invention, because location of blood vessels does not require actual imaging, there may be a balance obtained between the need for resolution and for penetration of tissue. Accordingly, an intermediate frequency may be used (e.g., around 8 Mhz). A variation of the invention may include inserting a fluid into the airway to provide a medium for the Doppler sensors to couple to the wall of the airway to detect blood vessels. In those cases where fluid is not inserted, the device may use mucus found within the airway to directly couple the sensor to the wall of the airway.

Figure 5A:
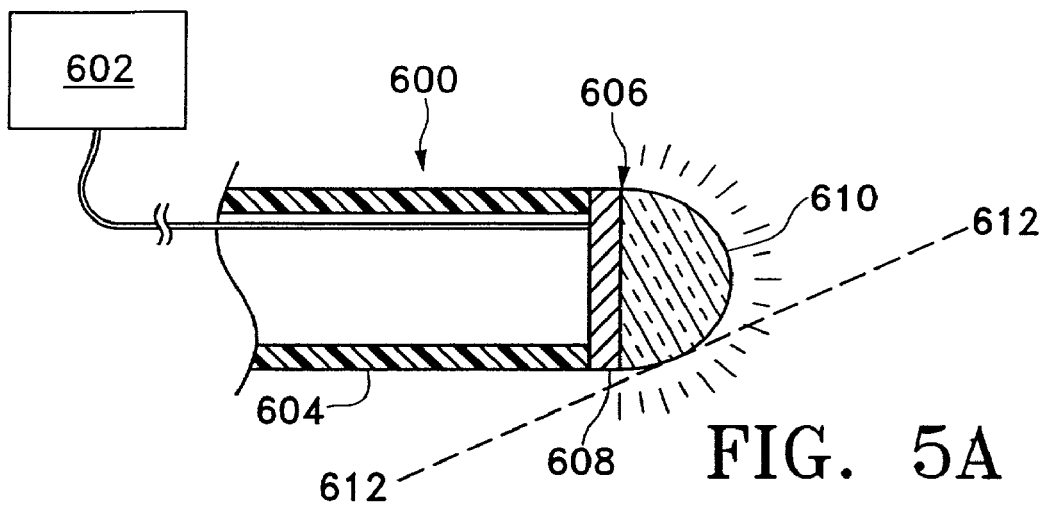
FIGS. 5A–5D illustrate devices for detecting blood vessels within tissue.

FIG. 5A illustrates a variation of a device 600 adapted to determine the presence of blood vessels as previously mentioned. The device 600 includes a flexible elongate member 604 having a transducer assembly 606, at least a portion of which is located adjacent to a distal end of the elongate member 604. Although the elongate member 604 is illustrated as having a lumen, the elongate member 604 may also be selected to be solid, or the elongate member 604 may have a support member (not shown) such as a braid to increase the strength and/or maneuverability of the device. The transducer assembly 606 is adapted to generate a source signal and receive a reflected signal. It may use a single transducer or multiple transducers. For example, at least a first transducer may be used to generate a signal and at least a second transducer may be used to receive the signal.

The transducer or transducers may comprise a piezo-ceramic crystal. In the current invention, a single-crystal piezo (SCP) is preferred, but the invention does not exclude the use of other types of ferroelectric material such as poly-crystalline ceramic piezos, polymer piezos, or polymer composites. The substrate, typically made from piezoelectric single crystals (SCP) or ceramics such as PZT, PLZT, PMN, PMN-PT; also, the crystal may be a multi layer composite of a ceramic piezoelectric material. Piezoelectric polymers such as PVDF may also be used. The transducer or transducers used may be ceramic pieces coated with a conductive coating, such as gold. Other conductive coatings include sputtered metal, metals, or alloys, such as a member of the Platinum Group of the Periodic Table (Ru, Rh, Pd, Re, Os, Ir, and Pt) or gold. Titanium (Ti) is also especially suitable. For example, the transducer may be further coated with a biocompatible layer such as Parylene or Parylene C. The transducer is then bonded on the lens. A coupling such as a biocompatible epoxy may be used to bond the transducer to the lens. The transducer assembly 606 communicates with an analyzing device 602 adapted to recognize the reflected signal or measure the Doppler shift between the signals. As mentioned above, the source signal may be reflected by changes in density between tissue. In such a case, the reflected signal will have the same frequency as the transmitted signal. When the source signal is reflected from blood moving within the vessel, the reflected signal has a different frequency than that of the source signal. This Doppler effect permits determination of the presence or absence of a blood vessel within tissue. Although depicted as being external to the device 600, it is contemplated that the analyzing device 602 may alternatively be incorporated into the device 600. The transducer assembly of the invention is intended to include any transducer assembly that allows for the observation of Doppler effect, e.g., ultrasound, light, sound etc. The device 600 illustrated in FIG. 5A includes a transducer assembly 606 comprising an ultrasound transducer 608 and an acoustic lens 610 that is adapted to refract and disperse a source signal over an outer surface of the lens 610. The lens 610 is designed such that it interferes and redirects the signals in a desired direction. The lens 610 may be comprised of materials such as dimethyl pentene (plastic-TPX), aluminum, carbon aerogel, polycarbonate (e.g., lexan), polystyrene, titanium, etc. It also may be desirable to place an epoxy between the lens 610 and the transducer 608. Preferably, the epoxy is thin and applied without air gaps or pockets. Also, the density/hardness of the epoxy should provide for transmission of the signal while minimizing any effect or change to the source signal. The configuration of the transducer assembly 606 permits the lens 610 to disperse a signal over a substantial portion of the outer surface of the lens 610. The lens 610 also is adapted to refract a reflected signal towards the transducer 608. Accordingly, given the above described configuration, the device 600 of FIG. 5A will be able to detect vessels with any part of the lens 610 that contacts tissue (as illustrated by the line 612—612.)

Although the lens 610 is illustrated as being hemispherical, as described below, the lens 610 may have other shapes as well.

Figure 5B:
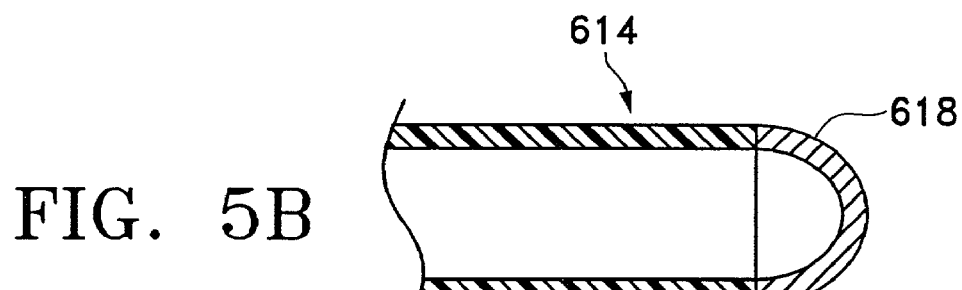

FIG. 5B illustrates another variation of the device 614 having a hemispherical shaped ultrasound transducer 618 affixed to an end of a flexible elongate member 616. The transducer 618 communicates with an analyzing device (not shown) to measure the Doppler effect to determine the location of a blood vessel.

Figure 5C:
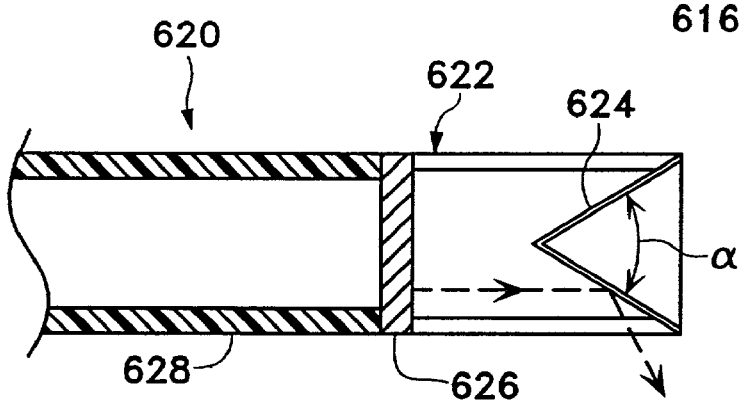

FIG. 5C illustrates another variation of the device 620 including a transducer assembly 622, at least a portion of which is located adjacent to a distal end of the elongate member 628. The transducer assembly 622 includes a flat ultrasound transducer 626, and a cone or wedge-like acoustic mirror 624. The mirror 624 is adapted to reflect the signal over an area 360° around the device. The angle α of the mirror may be varied to optimally direct the signal as needed.

Figure 5D:
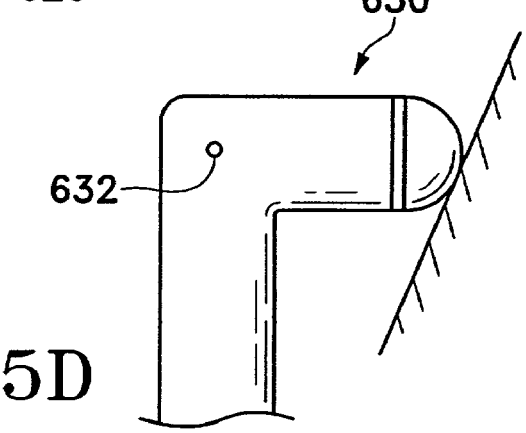

FIG. 5D illustrates a variation of a device 630 of the present invention further comprising a joint 632 to articulate an end of the device either to make sufficient contact with an area of tissue to be inspected for the presence of a blood vessel, or to navigate within the body to access the area to be inspected.

The variations of the invention described herein may also be adapted to use ultrasound energy, for example, high energy ultrasound, to produce openings in or marks on tissue. In such a case, the transducer assembly and acoustic lens also functions as a hole-making or site marking device. In this case, use of ultrasound in a low power operation permits the detection of a blood vessel and location of a site for a collateral channel. Using the same device and switching the operation of the device to a high power ultrasound permits the use of the ultrasound to create a collateral channel.

Figure 5E:
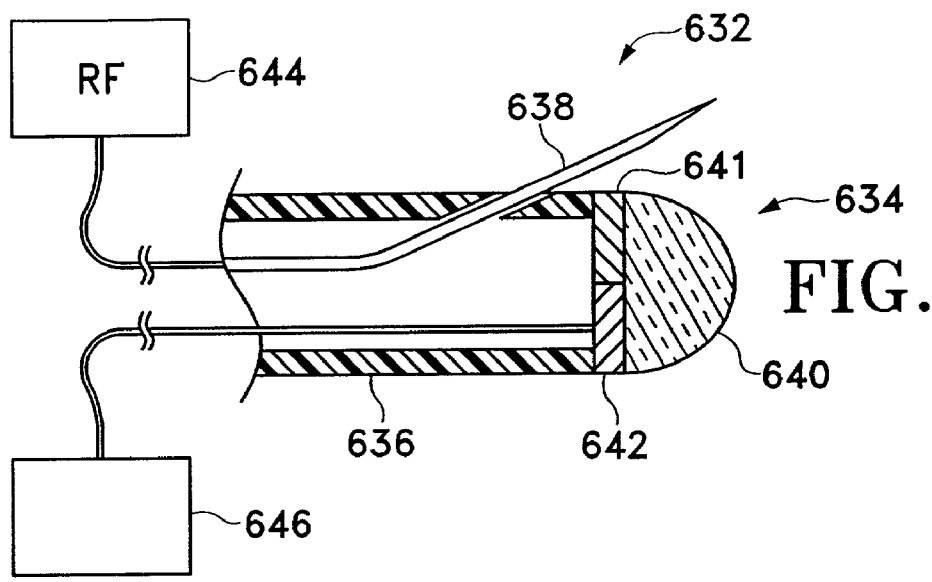
FIGS. 5E–5V illustrates various devices for detecting blood vessels within tissue where the devices also include hole-making assemblies.

FIG. 5E illustrates a variation of a device 632 comprising a transducer assembly 634 connected to a flexible elongate member 636. In this example, the transducer assembly 634 comprises a first transducer 641, a second transducer 642, and an acoustic lens 640. As mentioned above, in variations using alternate transducers 641, 642, one transducer may transmit a signal while the other receives a signal. Also, both transducers 641, 642 may simultaneously transmit and receive signals. It is intended that any combination of using the transducers to send and receive signals is contemplated. The device 632 also includes a hole-making assembly 638 for creating a channel in tissue. FIG. 5E illustrates the hole-making assembly 638 as an RF wire-like member. As illustrated, the device 632 is connected an RF generator 644 as well as an analyzing device 646 which is adapted to measure the Doppler shift between the generated and reflected signals.

Figure 5F:
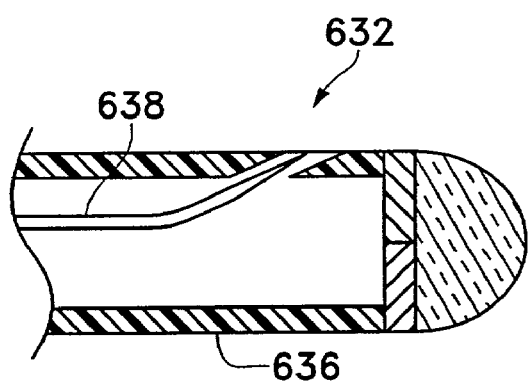

FIG. 5F illustrates the device 632 of FIG. 5E where the hole-making assembly 638 is retracted within the device 632, in this case within the elongated member 636.

Figure 5G:
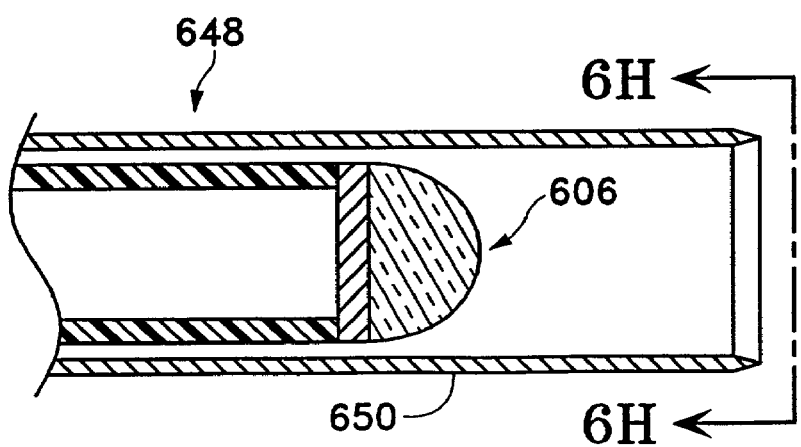
Figure 5H:
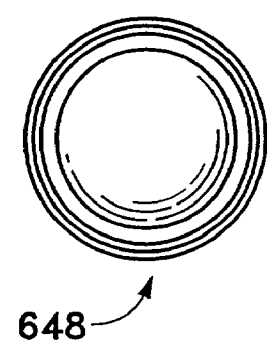

FIG. 5G illustrates another variation of a device 648 where a hole-making assembly 650 is exterior to a transducer assembly 606. The hole-making assembly 650 may be either an RF device or a mechanical device that simply cuts the tissue. For example, the hole making assembly 650 can be a hypotube placed over the transducer assembly 606. In this variation of the device 648, the transducer assembly 606 may be moveable within the hole-making assembly 650, or the hole-making assembly 650 may be moveable over the transducer assembly 606. In either case, the transducer assembly 606 may be advanced out of the hole-making assembly 650 to determine the presence of a blood vessel. If no blood vessel is found, the transducer assembly 606 may be withdrawn into the hole-making assembly 650 allowing the hole-making assembly 650 to create a channel in the tissue either by mechanically cutting the tissue, or by using RF energy to create the channel. FIG. 5H illustrates a view taken along the line 5H in FIG. 5G.

Figure 5I:
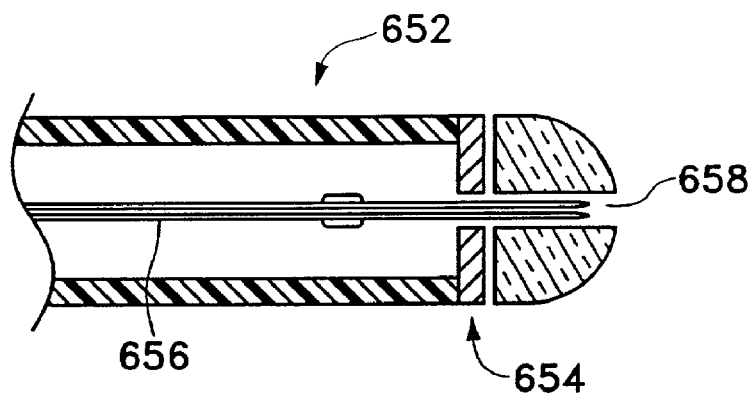
Figure 5J:
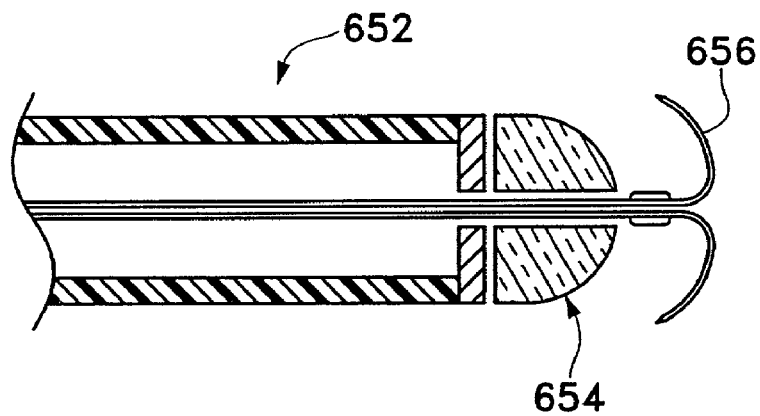

FIG. 5I illustrates another version of a device 652 of the present invention wherein the device has a transducer assembly 654 with an opening 658 through which a hole-making assembly 656 may extend. FIG. 5J illustrates the hole-making assembly 656 extended through the transducer assembly 654. The hole-making assembly 656 may comprise RF electrodes or needle-like members which puncture the tissue to create the channels.

Figure 5K:
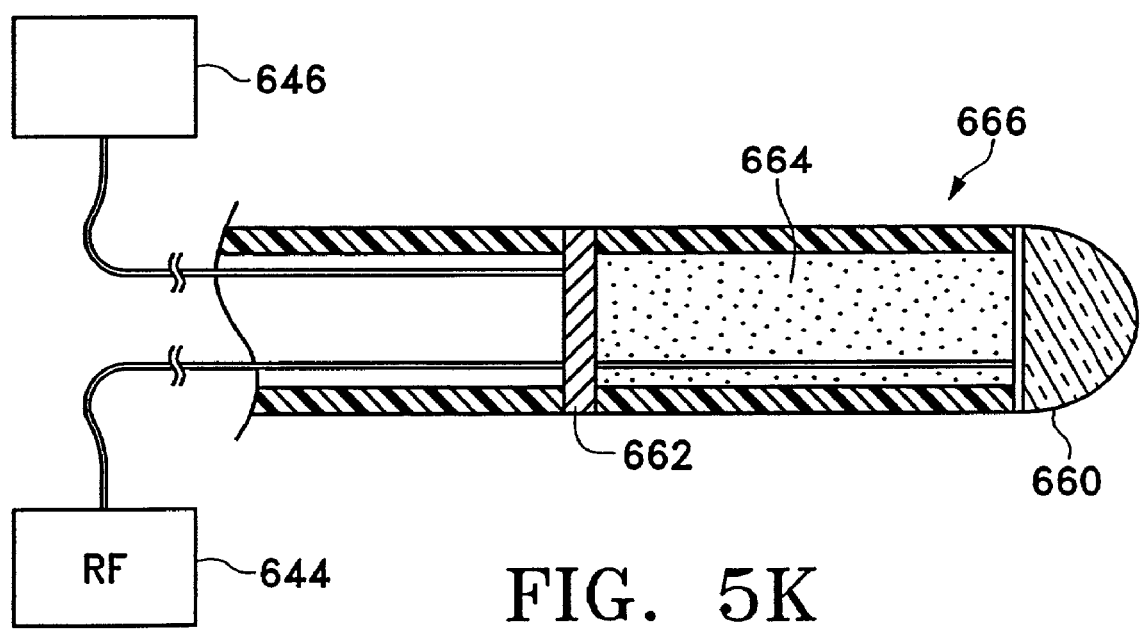

FIG. 5K illustrates a variation of a device 666 of the present invention where a tip 660 of the device has a conductive portion allowing the tip to serve as both an acoustic lens and an RF electrode. In such a case, the tip 660 is connected to an RF generator 644 for creating channels within tissue and a transducer 662 is placed in communication with an analyzing device 646 that is adapted to measure the Doppler shift between generated and reflected signals. In this variation, the tip 660 is separated from the transducer 662, but both the tip 660 and transducer 662 are in acoustic communication through the use of a separation medium 664. The separation medium 664 transmits signals between the tip 660 and the transducer 662. The spacing of the transducer 662 from the tip 660 serves to prevent heat or RF energy from damaging the transducer 662. It is intended that the spacing between the transducer 662 and tip 662 shown in the figures is for illustration purposes only. Accordingly, the spacing may vary as needed. The separation medium must have acceptable ultrasound transmission properties and may also serve to provide additional thermal insulation as well. For example, an epoxy may be used for the separation medium.

Figure 5L:
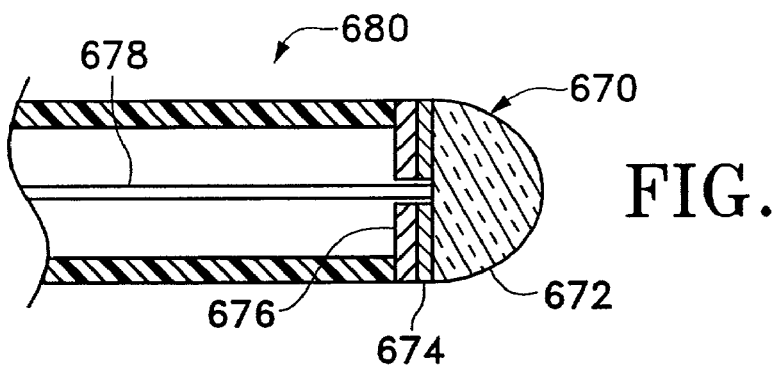
Figure 5M:
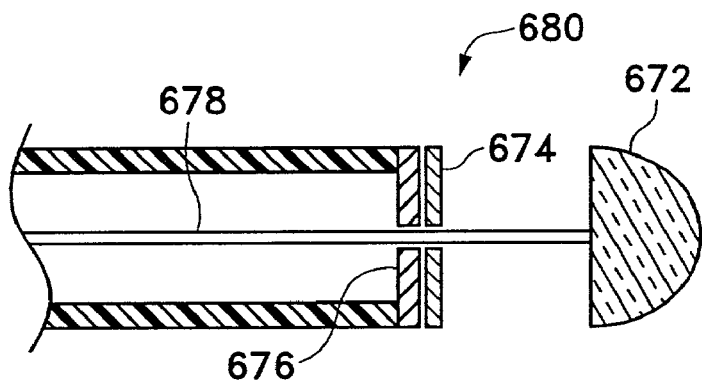

FIG. 5L illustrates a variation of a device 680 of the present invention wherein the transducer assembly 670 comprises a tip 672, an ultrasound coupling medium 674, a transducer 676, and an extension member 678. In this variation of the invention, the tip 672 of the device serves as an acoustic lens and also has conductive areas (not shown) which serve as RF electrodes. As shown in FIG. 5M, the tip 672 may extend from the device 680 and separate from the transducer 676. Separation of the tip 672 protects the transducer 676 from heat or RF energy as the tip 672 creates a channel in tissue. The extension member 678 may serve as a conductor to connect the tip 672 to an RF energy supply (not shown). When the tip 672 of the device 680 is being used in an ultrasound mode, the tip 672 may be coupled to the transducer 676 via the use of an ultrasound coupling medium 674. Any standard type of ultrasound gel material may be used, also highly formable silicone may be used. It is desirable to use a fluid boundary layer (such as the gel) which may be permanent or temporary. In those cases where the boundary layer is temporary, subsequent applications of the boundary layer may be necessary.

Figure 5N:
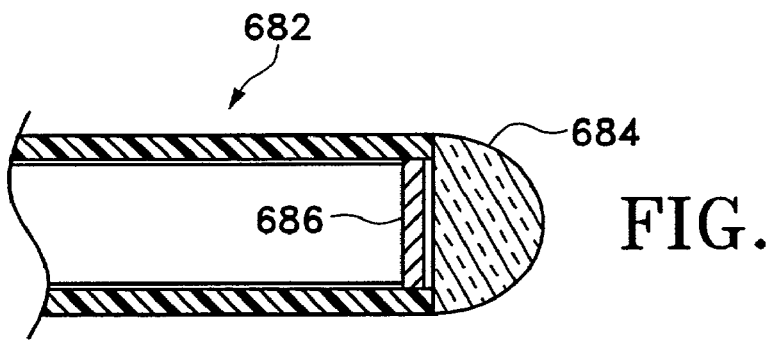
Figure 5O:
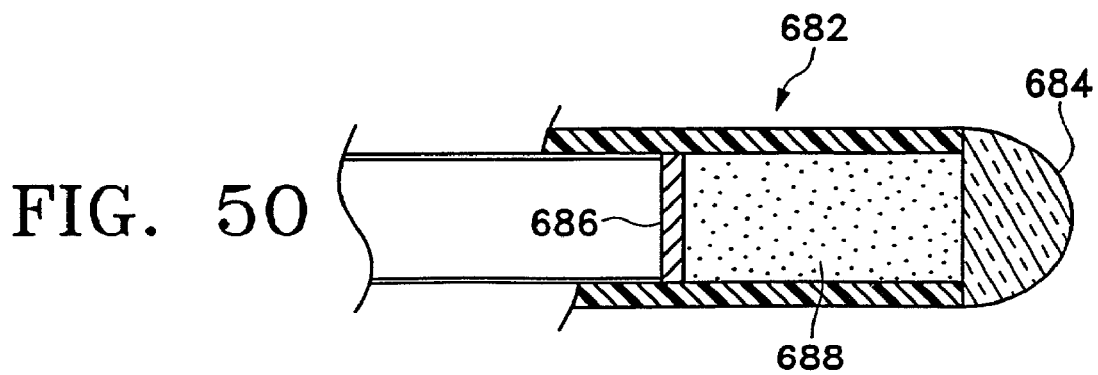

FIG. 5N illustrates another variation of a device 682 of the present invention having a tip 684 and transducer 686 that are separable from each other. Again, the tip 684 may include conductive areas and serve as both an RF electrode (not shown) as well as an acoustic lens. As shown in FIG. 5N, the tip 684 may be separable from the transducer 686 when creating a channel to protect the transducer 686 from heat or RF energy. The tip 684 may be placed in contact with the transducer 686 for operation in an ultrasound mode, or the device 682 may contain a separation medium 688 which permits acoustic coupling of the transducer 686 with the tip 684 when separated.

FIG. 5Q illustrates another variation of the inventive device 740 which is able to detect the presence or absence of a blood vessel using Doppler ultrasound and which is also able to create collateral channels within the lung tissue. The device includes a transducer adapted to generate a source signal and receive a reflected signal with a portion of the assembly located adjacent to the distal end of the elongate member 748. The transducer assembly may include at least one ultrasound transducer 742 and a lens 744 which enables the transmission and detection of a signal over a tip of the device 740. The device 740 further includes at least one heating element 746 located at a distal end of the lens 744. The heating element permits the device to create collateral channels. In the variation depicted in FIG. 5Q, the heating element 746 comprises a plurality of openings 750 which allow for passage of ultrasound signals through the heating element 746. Accordingly, the device 740 may use the transducer assembly to confirm the absence of a blood vessel at a particular site, and then use the heating element to create a collateral channel. FIG. 5P illustrates a front view of the device 740 of FIG. 5P further illustrating the heating element 746 with a number of openings 750. The number of openings 750 on a heating element is not limited to that shown. Moreover, the heating element 746 may comprise a mesh having a plurality of openings.

FIG. 5R illustrates a variation of the inventive device wherein the transducer assembly is moveable within a lumen of the elongate member 748. As described elsewhere herein, the transducer assembly may be moved when the heating element 746 is activated to create collateral channels. FIG. 5R depicts the device 740 as being connected to a power supply 752 and to an ultrasound controller device 754.

FIG. 5S illustrates another variation of a device of the present invention where the transducer assembly comprises at least one transducer 608 and an acoustic lens 610 that is adapted to refract and disperse a source signal over an outer surface of the lens 610. As described herein, the lens 610 is designed such that it interferes and redirects the signals in a desired direction. As illustrated, the transducer assembly is coupled to an ultrasound controller device 754. The device 756 further includes a heating element 758 located distally of the lens 610. The heating element 758 is coupled to a power supply 752. Although the heating element 758 is illustrated as extending into the elongate member 604 of the device 756, the device is not limited as such. In one variation of the invention, the heating element 758 may be configured in a "U" shape. With this configuration, after the device 756 penetrates tissue, rotation of the device 756 permits coring of the tissue to create a collateral channel. However, the heating element 758 may be configured in other shapes as needed.

Figure 5T:
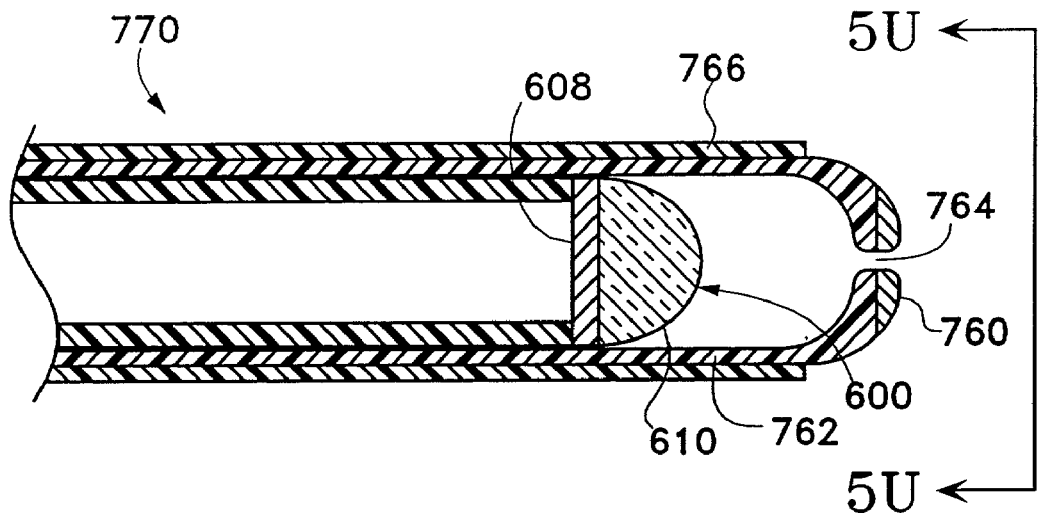
Figure 5U:
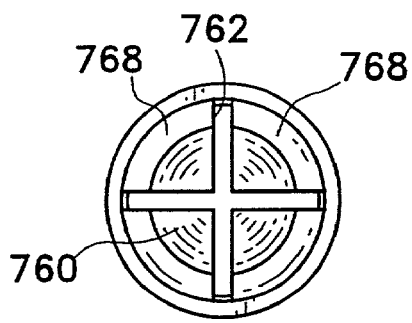
Figure 5V:
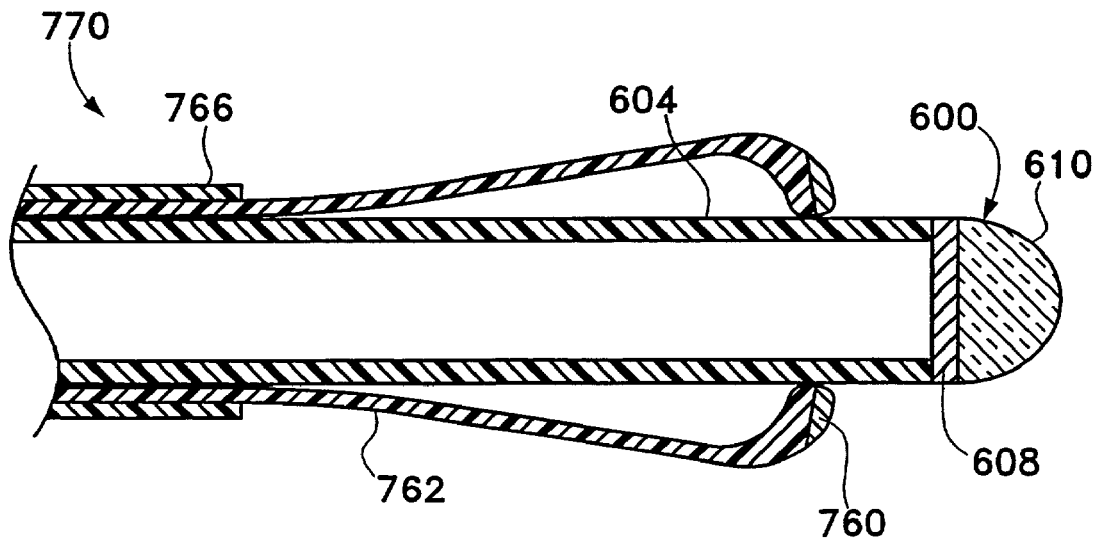

FIGS. 5T–5V illustrate another variation of the inventive device 770 which is adapted to detect the presence or absence of a blood vessel using Doppler ultrasound and which is also able to create collateral channels within the lung tissue. In this variation, the device 770 includes a detection device 600 adapted to determine the presence of blood vessels, as discussed above, is moveably located within an elongate member 762. At least a portion of the lumen of the elongate member 762 has a reduced opening 764 which is smaller than a diameter of the detection device 600. It is noted, that the detection device may be any detection device described herein.

As shown in FIG. 5V, a distal end of the elongate member 762 may be radially adjustable to permit movement of the detection device 600 in and out of the lumen. In the variation of the device depicted in FIG. 5V, a heating element 760 is placed on a distal end of the elongate member 762. Accordingly, when the detection device 600 is advanced out of the elongate member 762, the detection device 600 may determine the presence or absence of a blood vessel. Once a suitable location is found for the creation of a collateral channel, the detection device 600 is retracted into the elongate member 762, thereby positioning the heating element 760 to create a collateral channel. Optionally, as the heating element 760 generates heat as it creates the collateral channel, the detection device 600 may be moved proximally to minimize the possibility of any damage resulting from the generated heat. It should be noted that the elongate member may contain a shoulder to limit the depth of the collateral channel. Alternatively, in another variation of the invention, the detection device 600 may be configured to create a collateral channel via ultrasound energy. In such a case, no heating element is required and the expandable distal end of the elongate member 762 may serve as a shoulder to limit the depth of the collateral channel. In any case, as shown in FIG. 5U, when the device 770 is advanced through the airways of a lung, the detection device 600 may remain within the elongate member 762.

As with similar embodiments described herein, the distal end of the elongated member 762 may be remotely actuated to expand, or, the distal end may be biased to expand outwardly. In the latter case, the distal end may be restrained, for example, by an outer tubular member 766. The outer tubular member 766 may also be used to reduce the diameter of the distal end to secure against the detection device 600, as shown in FIG. 5V. The distal end of the elongated member 762 may be a continuous tubular structure which expands in diameter, or it may be a tubular structure that divided into any number of portions 768 which permit radial expansion of the distal end. For example, FIG. 5U illustrates a front view of the device of FIG. 5T in which at least a segment of the elongated member 762 is divided into four portions 768 so that it may be radially adjustable. It is understood that the number of portions 768 illustrated are merely exemplary, as the number may be varied as needed. Furthermore, the elongated member 762 may not be divided into any such portions 768 and instead may be an expandable elastic member.

Figure 6A:
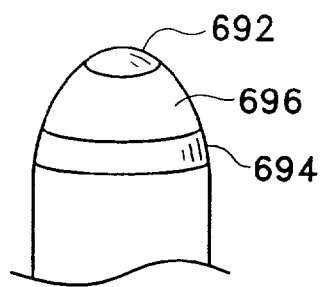
FIGS. 6A–6G illustrate various electrode configurations for the hole-making assemblies of the device.
Figure 6B:
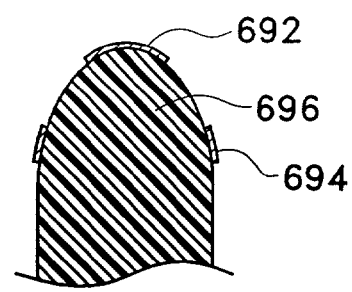
Figure 6C:
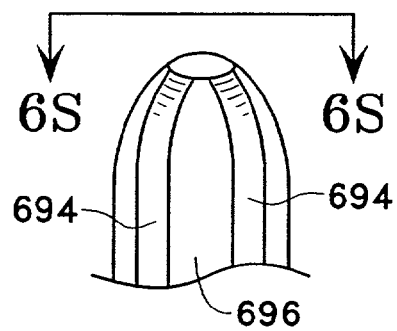
Figure 6D:
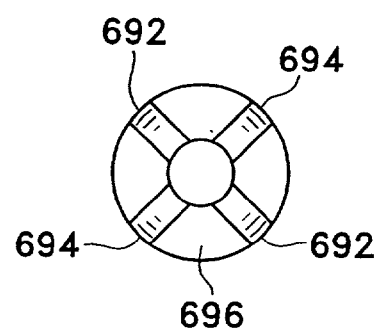
Figure 6E:
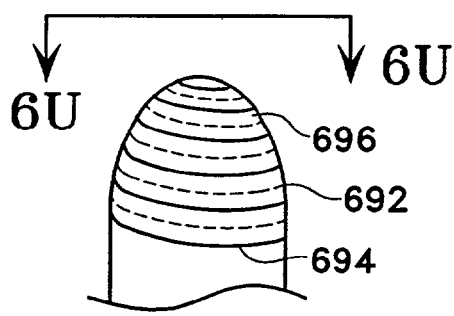
Figure 6F:
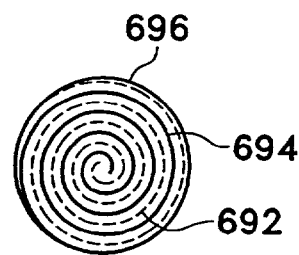
Figure 6G:
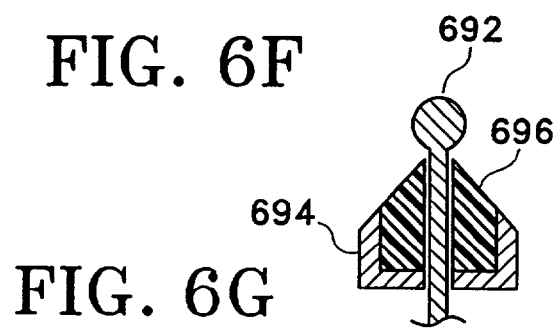

FIGS. 6A–6F illustrate variations of RF electrode tip 690 configurations for use with the present invention. As illustrated, the electrodes may be placed around a circumference of a tip, longitudinal along a tip, spirally along a tip, or a combination thereof. The electrodes 692, 694 may be used with a device having an acoustic lens or the electrodes may be employed solely as an RF hole-making device. While the variations illustrated in FIGS. 6A–6F show bipolar RF devices, the invention may also use a single electrode (monopolar.) The tip 690 may contain a first electrode 692 separated from a second electrode 694 by an electrical insulator 696 (e.g., ceramic, or plastic insulator). In variations of the device where electrodes are positioned on an acoustic lens, a sufficient amount of surface area of the lens must remain uncovered so that sufficient coupling remains for transmission of a signal between the lens and tissue. FIG. 6G illustrates a co-axial variation of a bi-polar RF tip having a first electrode 692, a second electrode 694, and an insulator 696.

Figure 6H:
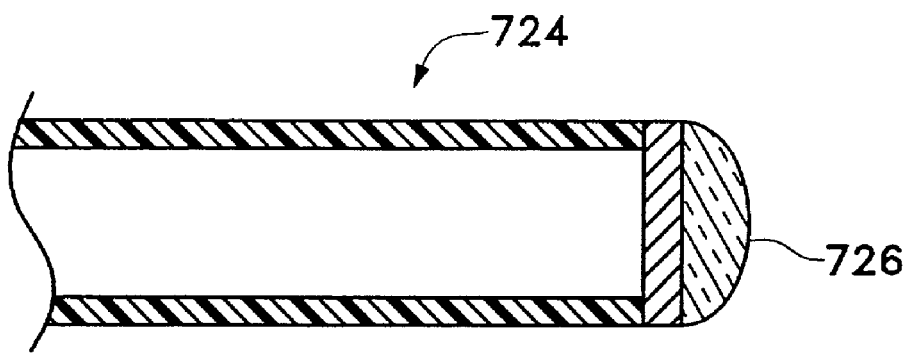
FIGS. 6H–6J illustrates additional variations of the lens of the present invention.
Figure 6I:
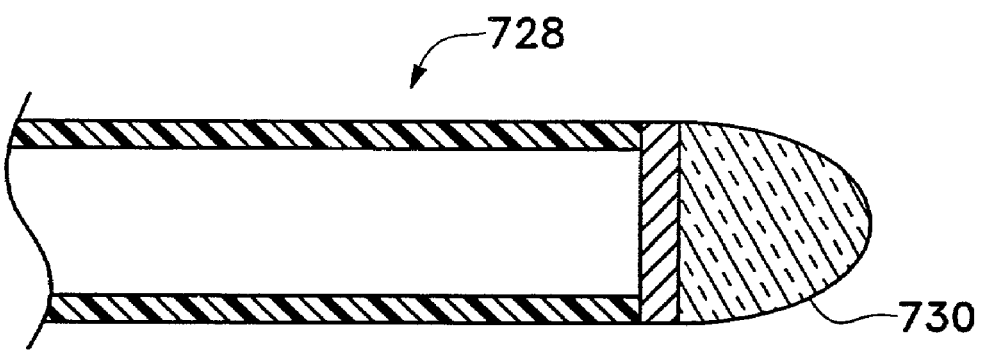
Figure 6J:
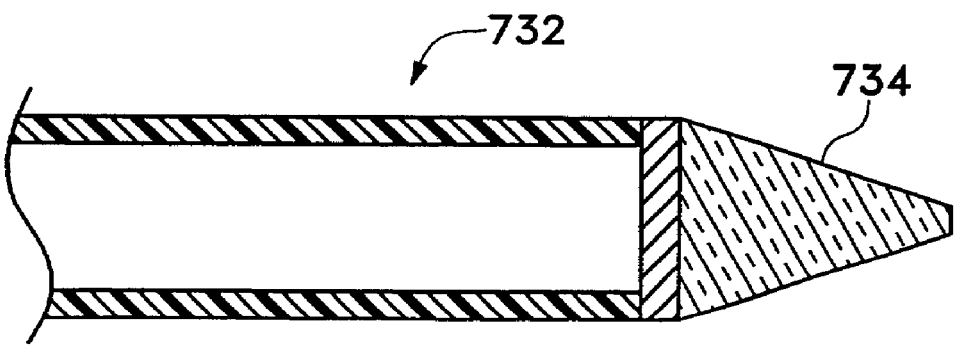

FIGS. 6H–6J illustrates additional variations of the lens of the present invention. FIG. 6H illustrates a device 724 with an acoustic lens 726 having an oblate spheroid shape. FIG. 6I illustrates a device 728 with an acoustic lens 730 having a prolate spheroid shape. FIG. 6J illustrates a device 732 having a conical-shaped acoustic lens 734. These variations are only intended to illustrate variations of the lens. It is contemplated that the shape of a lens may not follow a mathematical description such as conical, prolate, oblate or hemispherical. The design of the shape relates to the distribution pattern of the signal over the lens. The shapes can affect the distribution pattern by making it wider or narrower as needed. In any case, the lens is of a shape that provides coverage over the front face of the device.

Figure 7A:
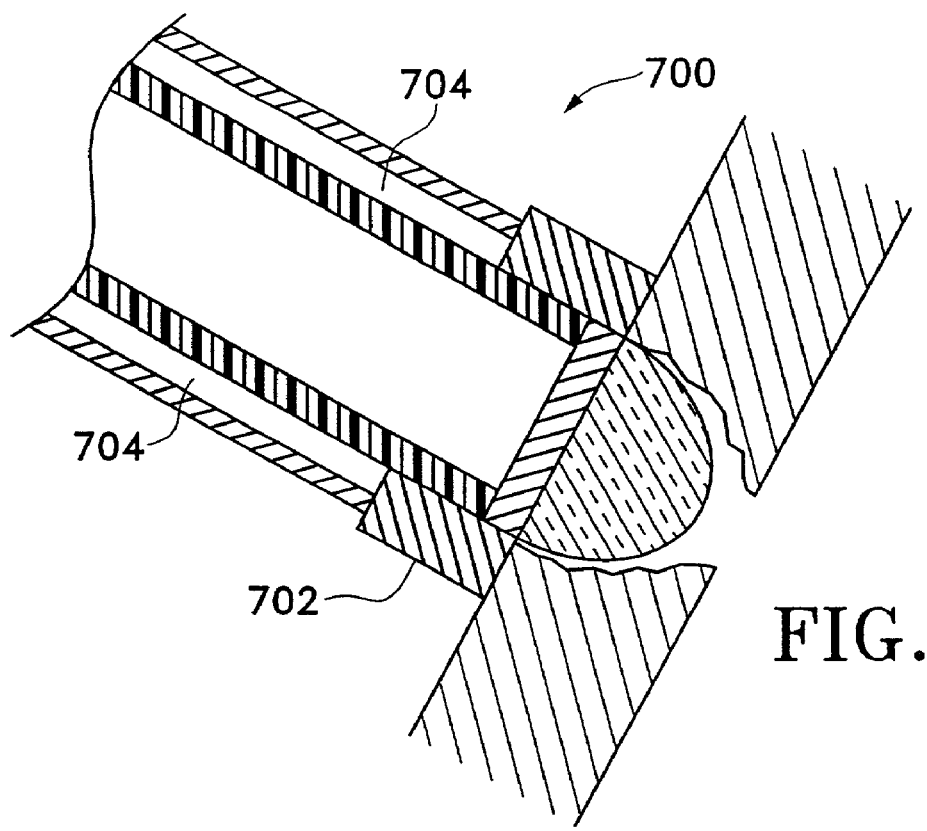
FIGS. 7A–7B illustrate devices and methods for creating a collateral channel with a device having a hole-making assembly and also preserving the tissue surrounding the collateral channel.

FIG. 7A illustrates a variation of the invention where a device 700 includes a heat-sink member 702. The heat-sink member 702 may preserve surround tissue during creation of the collateral channel. Or, the heat-sink member 702 may be a section of conductive material or a balloon. The heat-sink member 702 may be in fluid communication with a lumen 704 that provides a fluid, such as saline, that conducts heat away from the area surrounding the channel.

Figure 7B:
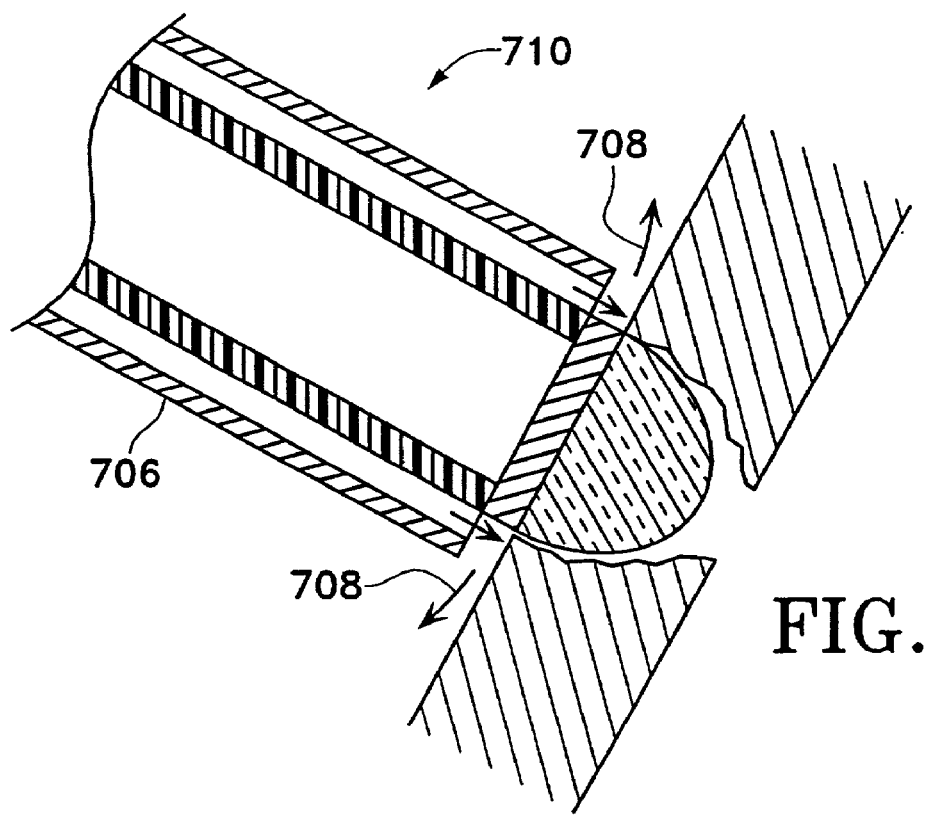

FIG. 7B illustrates another variation of a device 710 having a fluid delivery assembly 706 which assists in preserving surrounding tissue while a channel is being created. The fluid delivery assembly 706 may spray, mist, or otherwise apply fluid 708 to the area surrounding the channel. For example, cooled saline may be applied to the area to prevent excessive heating of the target area.

Figure 7C:
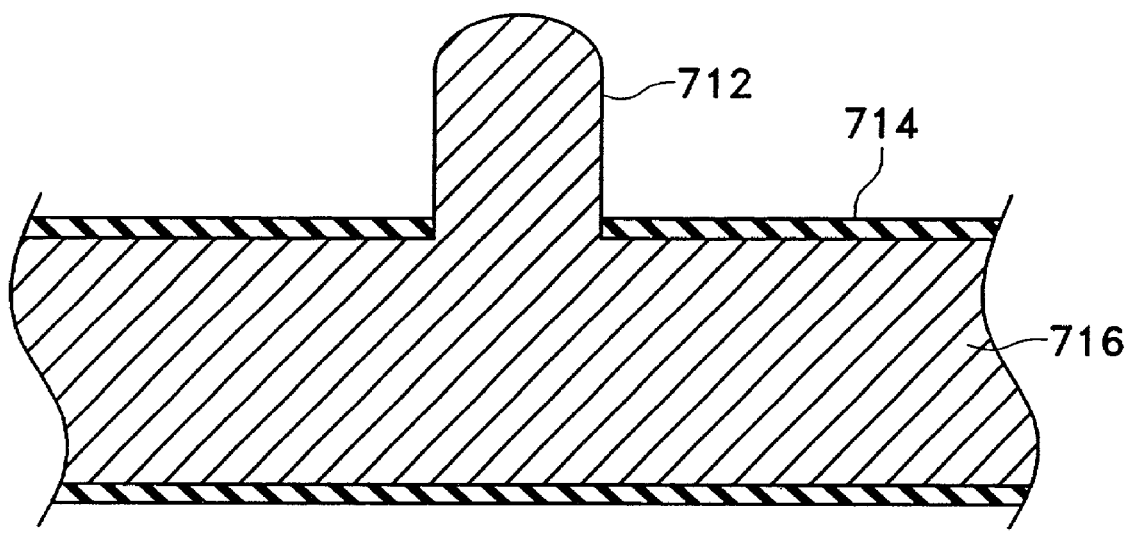
FIGS. 7C–7D illustrate additional electrode configurations for use with a device of the present invention where the structure of the electrodes limits the possible depth of a collateral channel formed by the electrode.
Figure 7D:
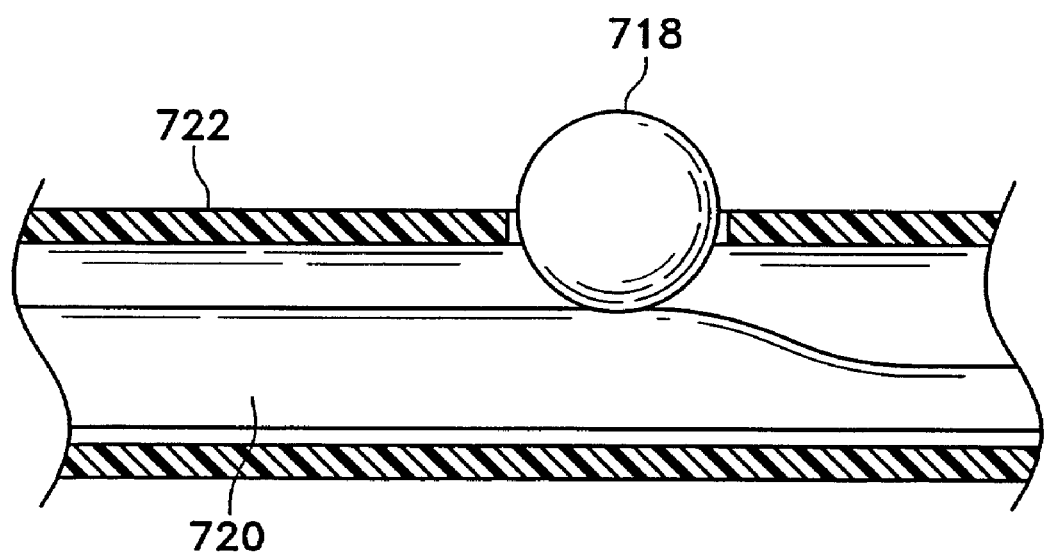

The invention includes the use of hole-making assembly on the side of the device with a transducer assembly on the tip of the device. For example, FIG. 7C illustrates a variation of an RF electrode 712 for use with the present invention. The electrode 712 may be a protrusion extending from a conductive member 716 that is covered with an insulating material 714. In this variation, the electrode 716 limits the depth of the channel due to the amount of material extending from the conductive member 716. The conductive member 716 may be connected to a source of RF energy (not shown) or may use another heating element (not shown). FIG. 7D illustrates another variation of an electrode configuration. In this variation, the electrode comprises a spherical member 718 extending from an elongate member 722. The electrode 718 is retractable through the elongate member 722 by use of an actuator 720. The actuator 720 may be conductive and connected to a source of RF energy to conduct energy through the electrode 718. Again, the design of the electrode 718 limits the depth of penetration of the electrode 718 while creating a channel in tissue. The electrodes described herein may also be used in conjunction with a device having a Doppler arrangement.

Also, a variation of the invention contemplates the delivery of drugs or medicines to the area of the collateral opening. Also contemplated is the use of a fibrin, cyanoacrylate, or any other bio-compatible adhesive to maintain the patency of the opening. For example, the adhesive could be deposited within the collateral channel to maintain patency of the channel or to create a cast implant of the channel. The adhesive could also coat the channel, or glue a flap to the wall of the airway. Also, the use of a bioabsorbable material may promote the growth of epithelium on the walls of the conduit. For example, covering the walls of a channel with small intestine submucosa, or other bioabsorbable material, may promote epithelium growth with the bioabsorbable material eventually being absorbed into the body.

Figure 8A:
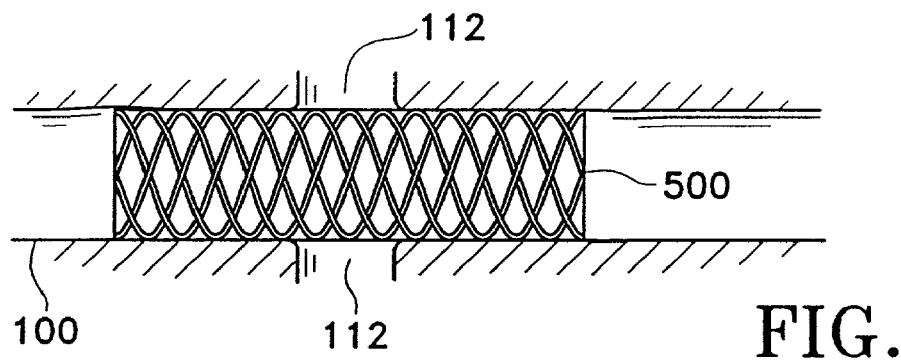
FIGS. 8A–8V illustrate various configuration of implantable conduits.

FIG. 8A illustrates an implant or conduit 500 placed within a natural airway 100. As shown, the airway 100 has a portion of its wall removed, thereby providing a collateral opening 112 within the airway 100. The implant 500 typically has a porous structure which allows gasses to pass between the airway and the channels 112 and into the lung. Moreover, the structure of the insert 500 also maintains patency of the airway 100 and the channel 112.

Any variation of a conduit described herein may comprise a barrier layer which is impermeable to tissue. This aspect of the invention prevents tissue in-growth from occluding the channel. The barrier layer may extend between the ends of the body or the barrier layer may extend over a single portion or discrete portions of the body of the conduit.

Figure 8B:
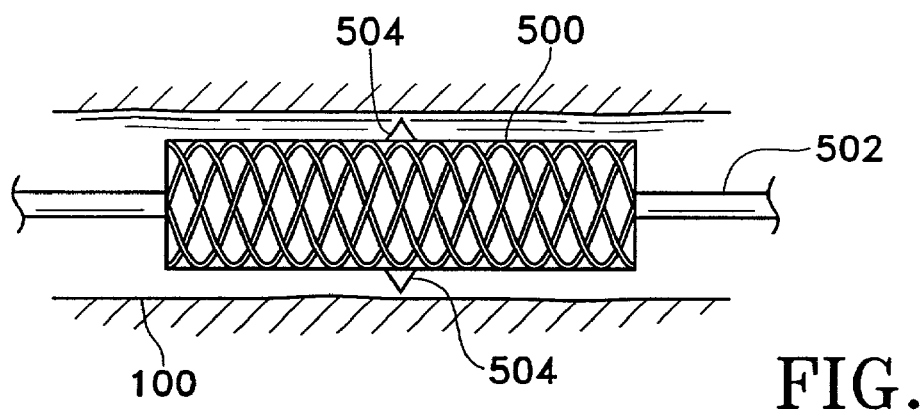
Figure 8C:
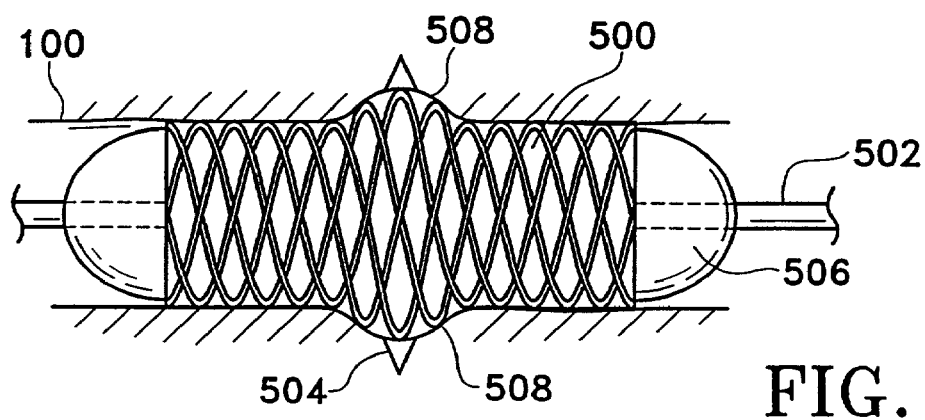

FIG. 8B illustrates an conduit 500 having an expandable structure within an airway 100. Usually, the conduit 500 has a porous wall that allows the passage of gasses through the wall. The conduit 500 is delivered via a delivery device 502 which may also contain an expandable member (not shown) which expands the conduit 500. As shown in FIG. 8C, the conduit may have piercing members 504 attached on an outer surface which enable the conduit 500 to create an incision within the airway 100.

FIG. 8C illustrates the conduit 500 after being expanded by an expandable member 506, e.g. a balloon device, an expandable mechanical basket, or an expandable wedge. In this example, the conduit 500 expands through the walls of the airway 100 at sections 508. In this variation, the conduit 500 is lodged within the walls of the airway 100.

Figure 8D:
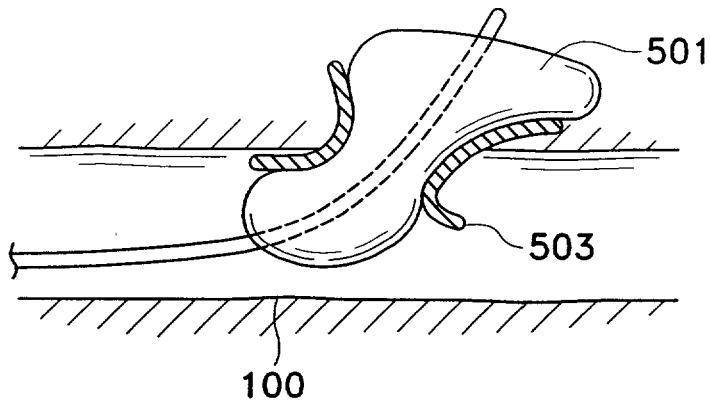

FIG. 8D illustrates a grommet-like insert 503 where the lumen of the insert 503 extends longitudinally through the collateral channel. In this example, an expanding member 501, e.g., a balloon, an expanding mechanical basket, or the like is used to secure the conduit 503 within the collateral channel.

Although not illustrated, the invention includes conduits having a length to diameter ratio approximately 1:1. However, this ratio may be varied as required. The cross-section of an implant may be circular, oval, rectangular, elliptical, or any other multi-faceted or curved shape as required. The cross-sectional area of an implant 500 may be between 0.196 mm$^2$ to 254 mm$^2$.

The conduit may also be any device capable of maintaining a patent opening, e.g., a plug, that is temporarily used as a conduit and then removed after the channel has healed in an open position. In another variation the plug may be a solid plug without an opening that is either bio-absorbable or removable. In such a case, the plug may be placed within an opening in tissue and allow the tissue to heal forming a collateral channel with the plug being ultimately absorbed into the body or removed from the body.

Figure 8E:
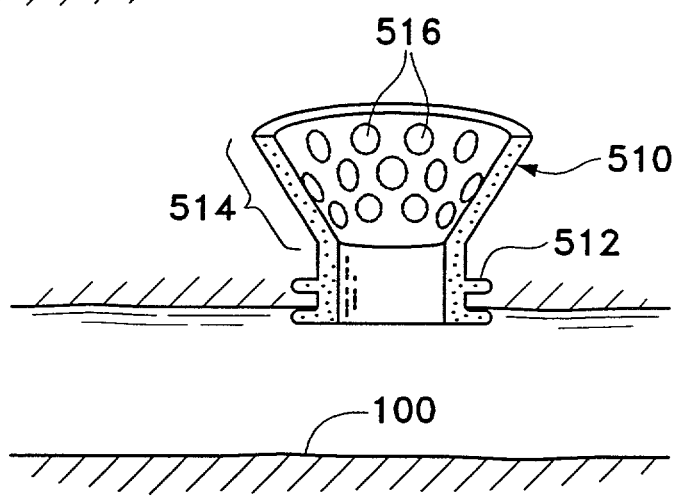

Another variation of the conduit is illustrated in FIG. 8E. In this example the conduit 510 comprises a cone 514 with a grommet 512 for attachment to a wall of the airway 100. The cone 514 may be porous or have other openings 516 to facilitate the passage of gas through the collateral channel. In the event that the distal opening of the cone become occluded, the porous cone permits the continued exchange of gasses between the collateral channel and the natural airway.

Figure 8F:
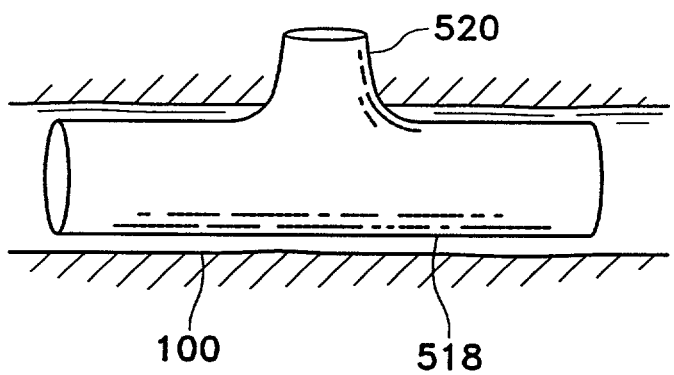

Another variation of the conduit is illustrated in FIG. 8F. For example, the conduit 518 may be configured in a 't-shape' with a portion 520 of the conduit extending through the collateral channel. Again, the conduit 518 may be constructed to have a porous wall to allow gas exchange through the wall. The conduit may be configured in a variety of shapes so long as a portion of the conduit extends through the collateral channel. The portion may be formed into a particular shape, such as the 't-shape' described above, or, the portion may be hinged so that it may be deployed within the channel. In such a case, a portion of a wall of the conduit may have a hinge allowing the wall of the conduit to swivel into a channel.

Figure 8G:
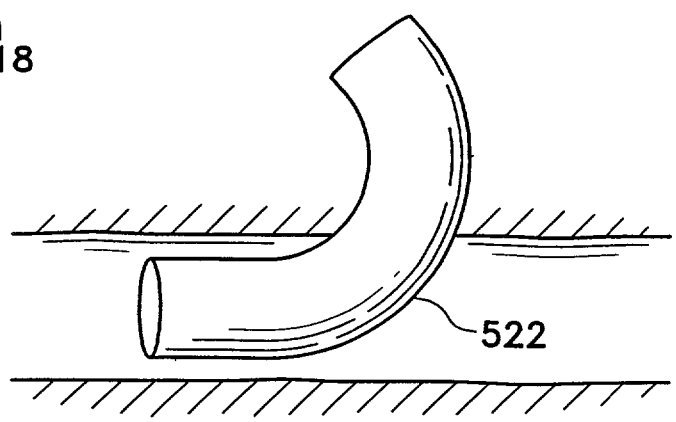

Yet another variation of the conduit is found in FIG. 8G. In this example, the conduit 522 is constructed with a geometry that reduces the chance that the conduit 522 will migrate within the airway 100.

Figure 8H:
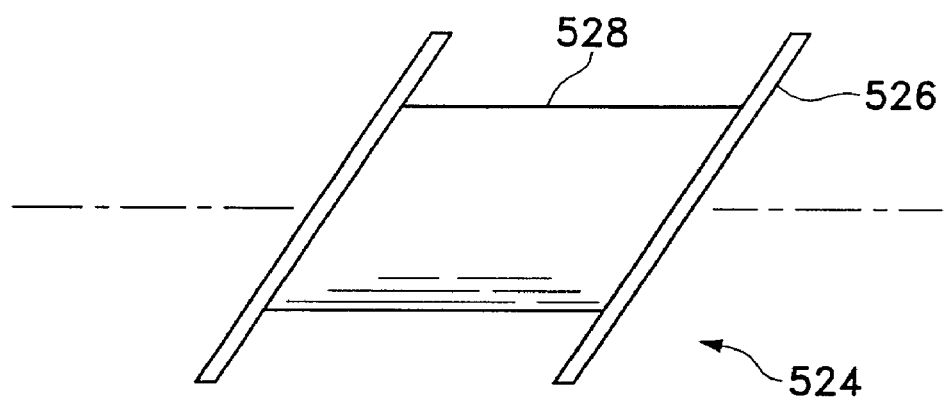
Figure 8I:
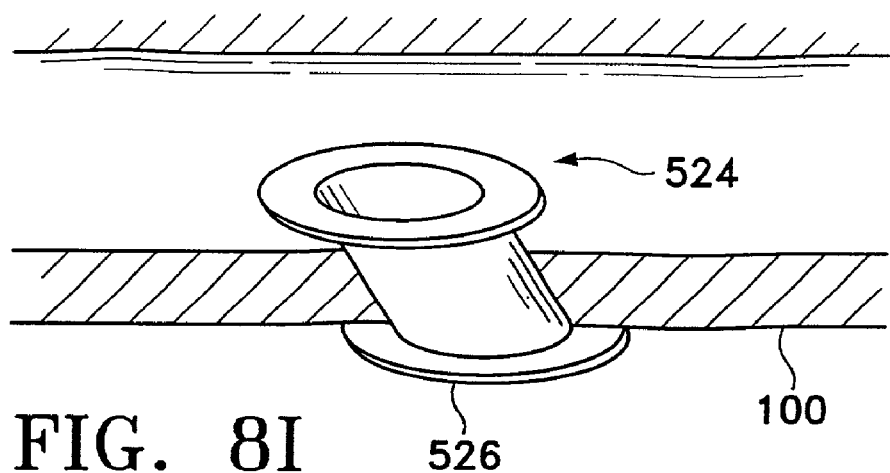

FIG. 8H illustrates an example of a conduit 524 having an asymmetrical profile. The conduit 524 may have a flange 526 at either or both ends of the body 528. Although not shown, the flange 526 may have a cone-like profile to facilitate placement within an airway. As illustrated in FIG. 8I, the asymmetrical profile of the conduit 524 assists in preventing obstruction of the airway.

Figure 8J:
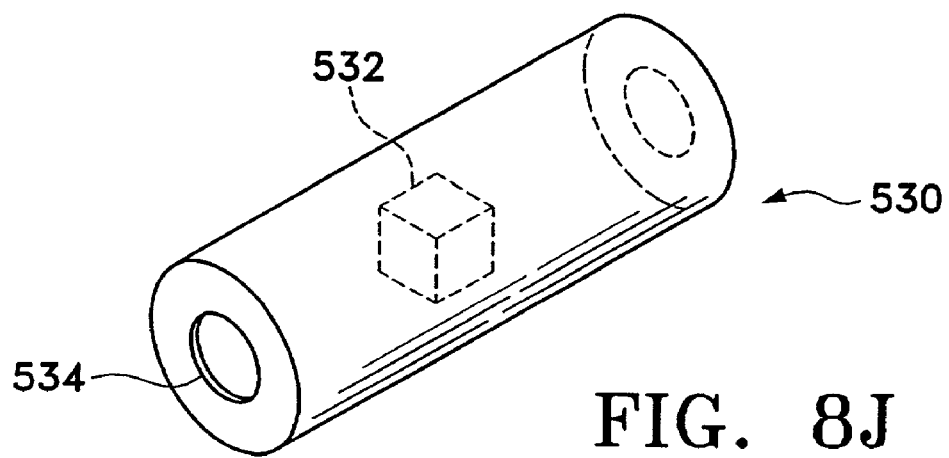

FIG. 8J illustrate a variation of the conduit 530 having a self-cleaning mechanism. In this example, the self cleaning mechanism is a floating ball bearing 532. The ends of the conduit 530 have a reduced diameter 534 which prevents the bearing 532 from escaping. As gas passes through the conduit 530, the bearing 532 moves about the conduit 530 clearing it of debris. The shape of the bearing 532 and the size and shape of the reduced diameter 534 may be varied to optimize the self-cleaning effect of the device.

Figure 8K:
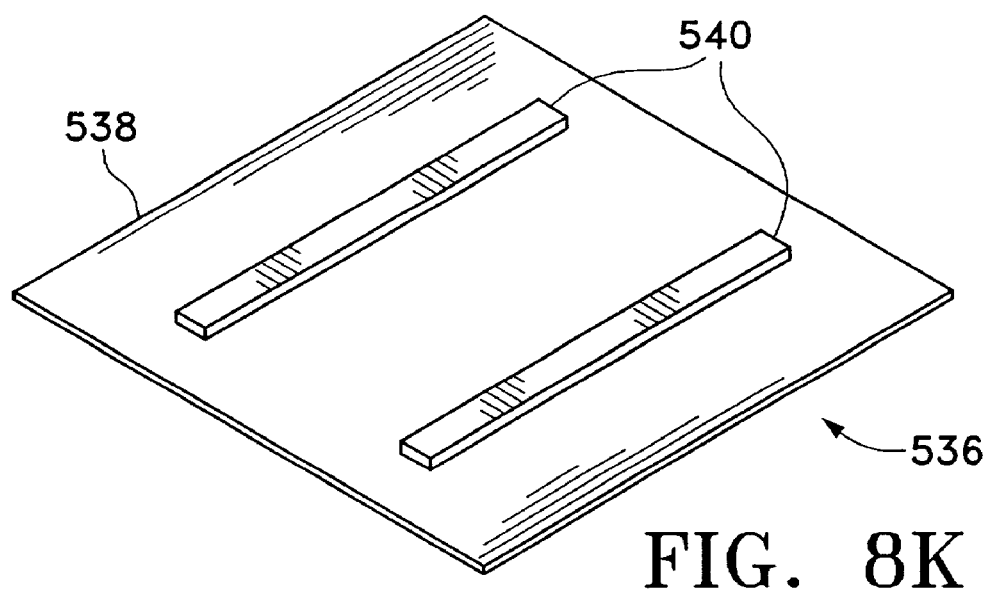
Figure 8L:
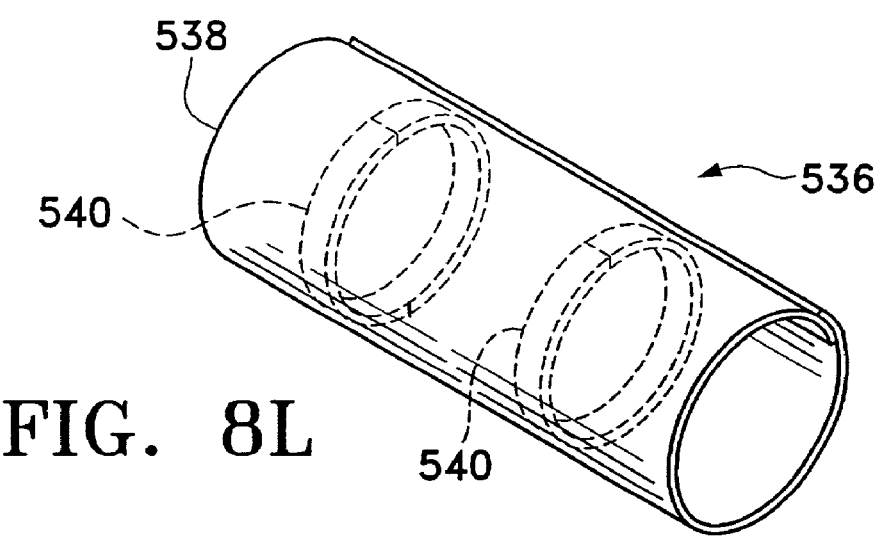

FIGS. 8K and 8L illustrate another variations of a self-expanding conduit 536. In this example, as shown in FIG. 8K, the conduit 536 may be constructed from a flat material 538 having a spring or springs 540. As shown in FIG. 8L, the conduit 536 is formed by rolling the assembly. The spring 540 provides an expanding force against the material 538. The conduit 536 may also be constructed so that the flat material 538 is resilient thus eliminating the need for springs 540.

Figure 8M:
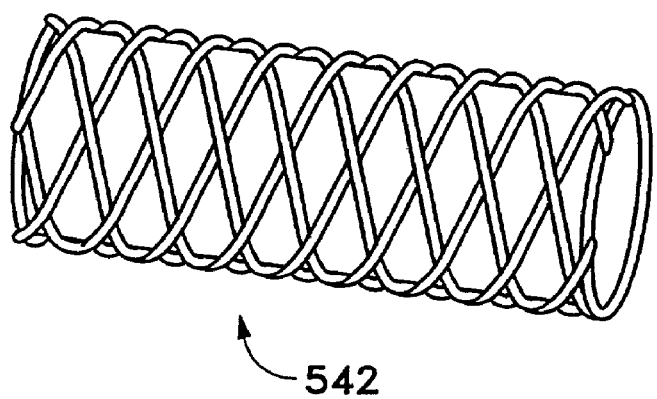

FIG. 8M illustrates another variation of an expandable conduit 542 constructed from a braided material. The conduit 542 may be constructed so that the diameter is dependent upon the length of the device 542. For example, the diameter of the device 542 may decrease as the length is stretched, and the diameter may increase as the length of the device 542 is compressed. Such a construction being similar to a 'finger cuff' toy.

Figure 8N:
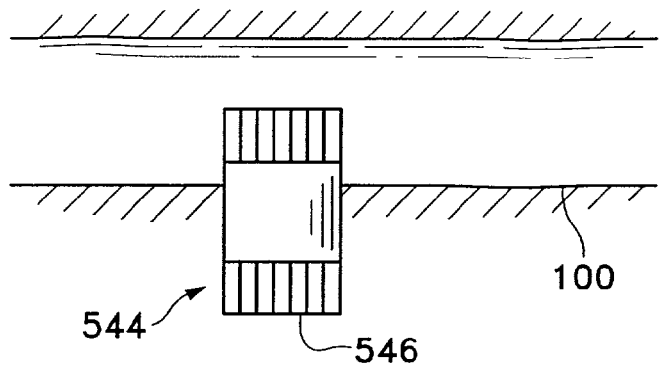
Figure 8O:
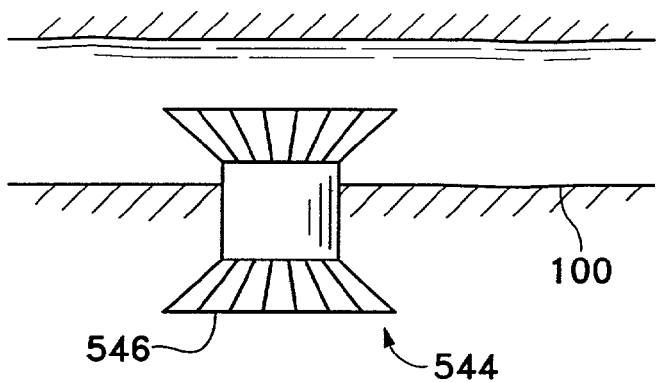
Figure 8P:
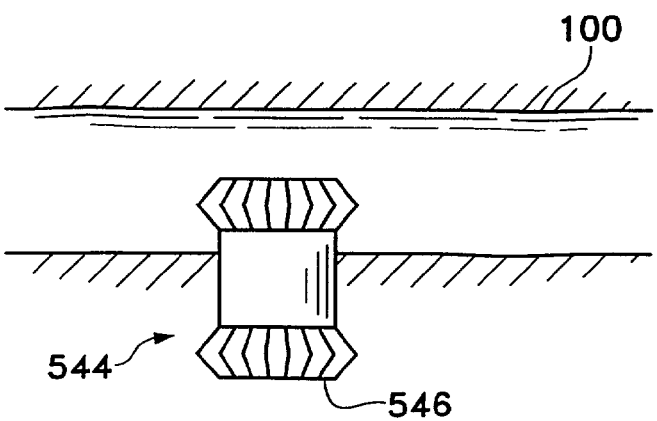

FIGS. 8N–8P illustrate another variation of a grommet-type conduit. FIG. 8N illustrates a conduit 544 having expandable ends 546. In one variation the ends 546 of the device 544 may flare outwards as illustrated in FIG. 5P. FIG. 8N illustrates another variation of the device 544 in which the ends 546 compress in length to expand in diameter.

Figure 8Q:
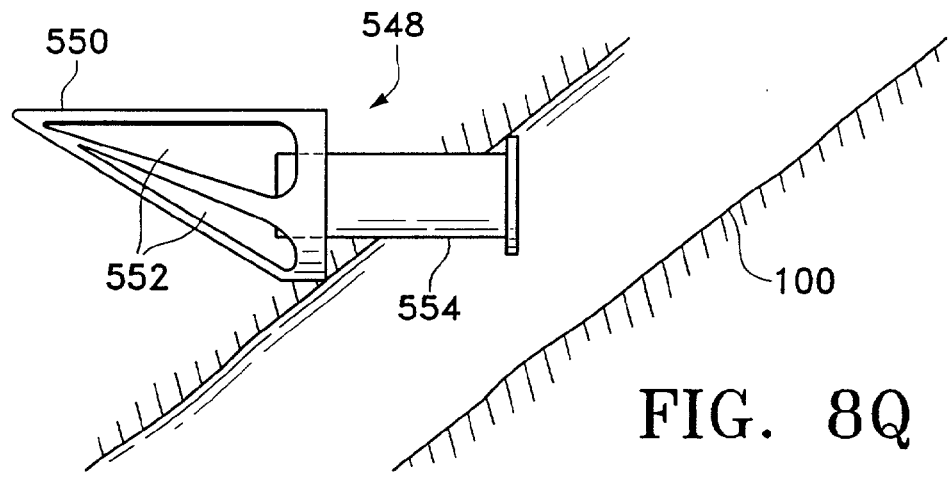
Figure 8R:
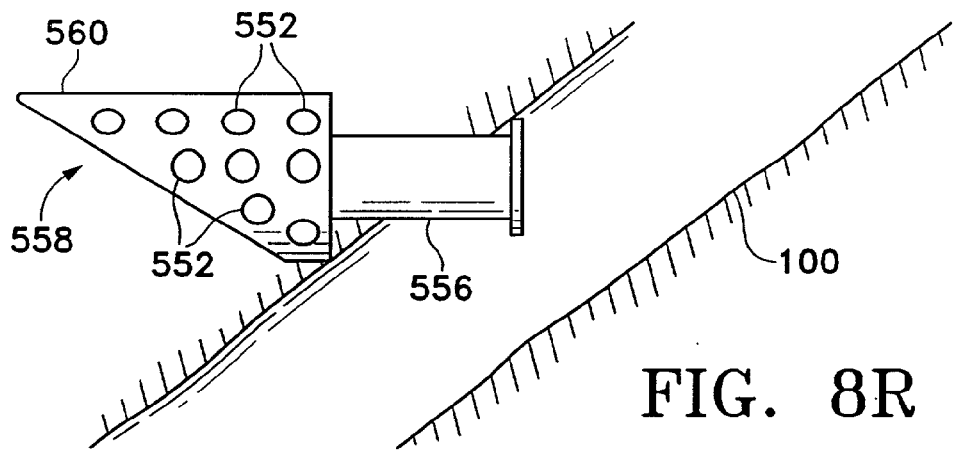

FIGS. 8Q and 8R illustrate variations of a conduit having an anchor. In FIG. 8Q, the conduit 548 has an anchor 550 at a distal end of a hollow plug 540. The anchor 550 may be tapered to facilitate entry into the airway 100 wall or may have another design as required. The anchor 550 also contains ventilation openings 552 to facilitate gas exchange through the device. FIG. 8R illustrates another variation of the device.

Figure 8S:
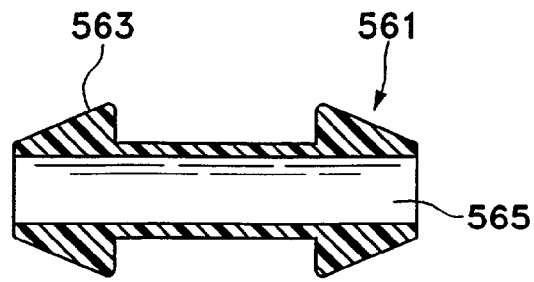

FIG. 8S illustrates a variation of a conduit 561 having flanges 563 at either end to assist in placement of the conduit within an airway wall (not shown). The ends of the conduit 565 may be tapered to ease placement through a collateral channel. The conduit has an opening 565 to facilitate passage of air. To simplify construction, the conduit 561 may be constructed from a biocompatible material, such as stainless steel, or plastic.

Figure 8T:
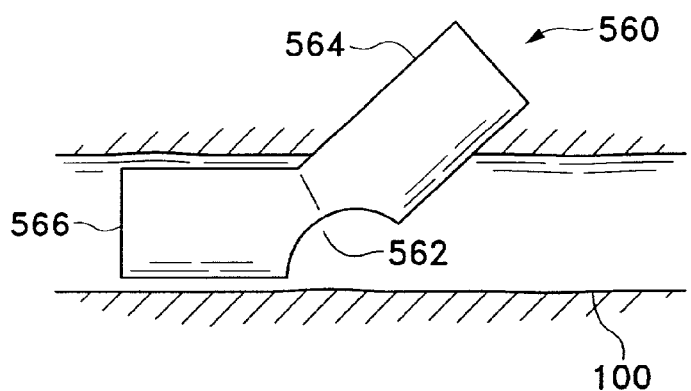

FIG. 8T illustrates a variation of the invention having multiple openings for gas flow. The conduit 560 has a first hollow end 564 which can extend through a wall of the airway 100 and a second hollow end 566 which can remain parallel to the airway 100. This example also includes an opening 562 which allows gas to flow through the airway 100.

Figure 8U:
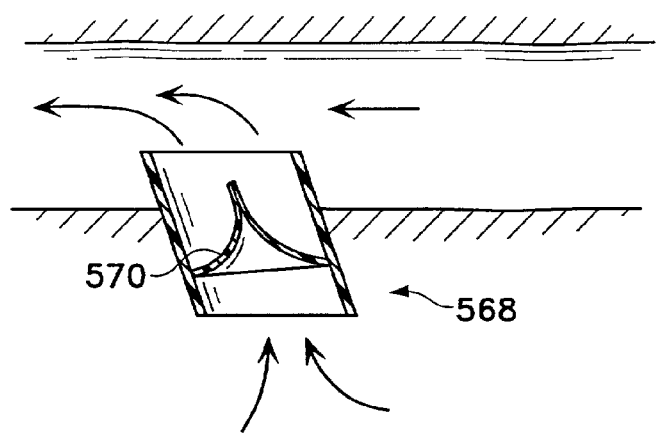

FIG. 8U illustrates a variation of the device having a one-way valve 570. The valve 570 allows the conduit 568 to permit exhaust of the air sac but prevents the conduit 568 from serving as another entrance of gas to the air-sac. The valve 570 may be placed at ends of the conduit or within a lumen of the conduit. The valve 570 may also be used as bacterial in-flow protection for the lungs.

Figure 8V:
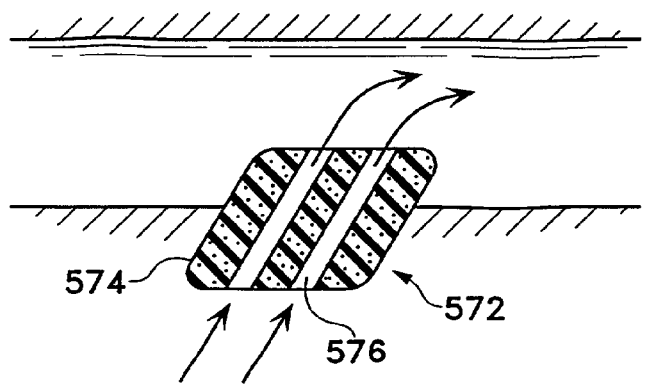

FIG. 8V illustrates another variation of a conduit 572. In this variation, the conduit 572 may be a sponge material, or constructed of an open cell material 574, which allows air flow through the material. Or, the conduit 572 may have lumens 576 which allow flow through the conduit 572. To assist the conduit 572 in remaining within a channel, the conduit material may be selected such that it expands as it absorbs moisture. Also, the sponge material/open cell material may be bio-absorbable to allow for temporary placement of the conduit 572.

FIGS. 9A–9F illustrate another variation of a conduit 800 of the present invention. The conduit 800 has a center section 802 having extension members 804 located at either end of the center section 802. The center section 802 illustrated is tubular but may be of any other shape as needed for the particular application. The conduit of the invention has a passageway extending between the ends of the conduit suited for the passage of air. The variation of the conduit 800 illustrated in FIG. 9A has a center section 802 comprising a mesh formed from a plurality of ribs 806. FIGS. 9A and 9B illustrate the conduit 800 in a reduced profile while FIGS. 9C and 9D illustrate the conduit 800 in an expanded profile after expansion of the center section 802 of the conduit 800. As shown in FIGS. 9E and 9F, each free end 808 of each extension member 804 is unattached to the center section 802 and is bendable about the respective end of the center section 802 to which it is attached. Accordingly, once a conduit 800 is placed within a collateral channel (not shown), the extension members 804 are bent about the end of the center section 802 and form a cuff or grommet which assists in keeping the conduit 800 within a collateral channel. Accordingly, the cross section and number of extension members 804 located about either end of the conduit 800 may be selected as necessary to assist in placement and securing of the conduit 800 within a channel.

The conduits described herein may have a fluid-tight covering, as discussed below, about the center section, the extension members, or the entire conduit. Also, the conduit may be designed to limit a length of the center section to less than twice the square root of a cross sectional area of the center section when the center section is in the expanded profile.

Figure 9G:
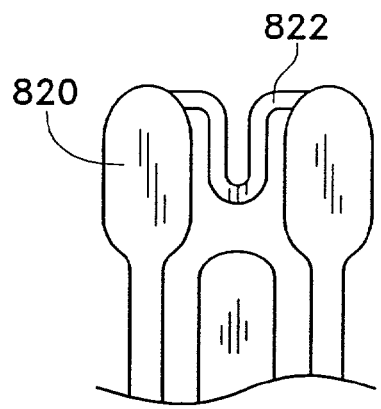
FIGS. 9A–9U, 10A–10B, and 11A–11C illustrate variations of conduits of the present invention.
Figure 9H:
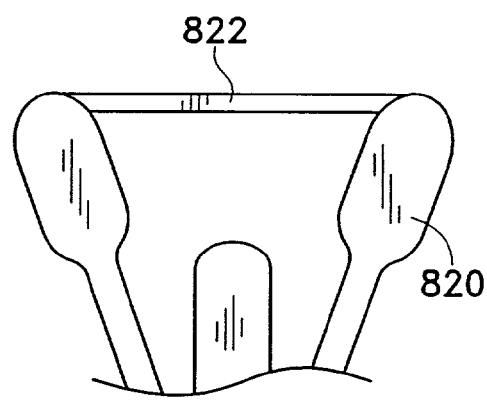
Figure 9I:
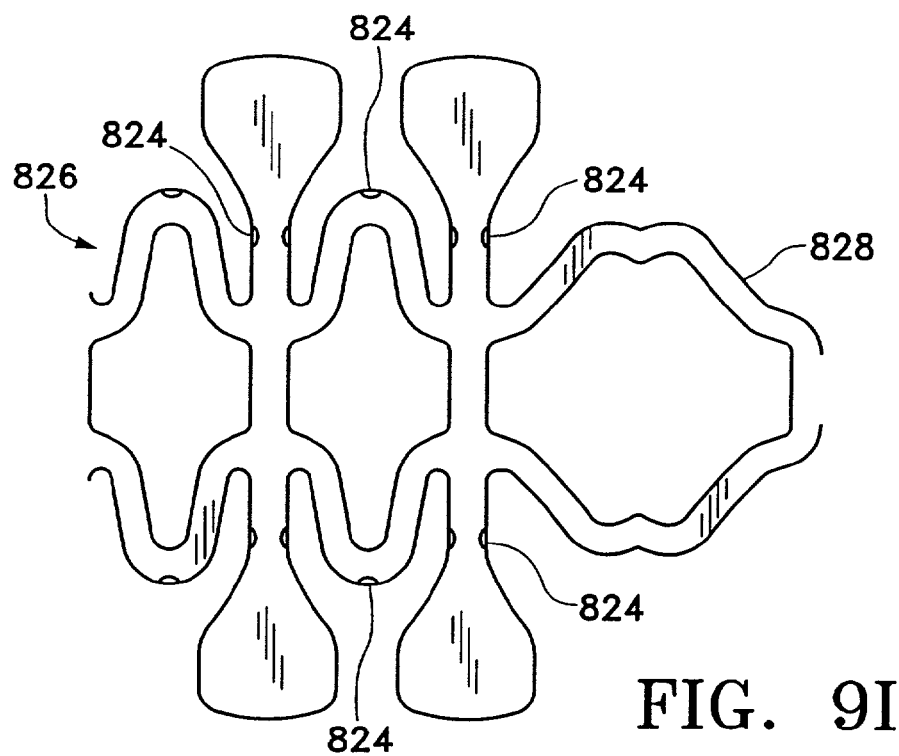

FIGS. 9G–9I illustrates another variation of a conduit 812 for use with the invention. In this variation, the conduit 812 is formed from a rolled sheet of material 810. The rolled sheet 810 may be heat treated to preserve the shape of the conduit 812 or the sheet 810 may simply be rolled to form the conduit 812. In those cases where the sheet of material 810 comprises a shape-memory alloy, it is desirable to process the material 810 so that it exhibits super-elastic properties at or above body temperature.

FIG. 9G illustrates a variation of extension members 820 for use with a conduit (not shown) of the present invention. In this variation, the extension members 820 have an attachment 822 between adjacent extension members 820. FIG. 9H illustrates the extension members 820 as the conduit (not shown) is expanded and the extension members 820 are bent on the conduit. The attachment 822 assists in preventing the extension members 820 from deviating from a preferred position. As illustrated in FIG. 9I, the conduit 826 may have cut or weakened sections 824 to facilitate expansion of the conduit 826 and bending of the extension members in a desired manner (as shown by the section of 828).

Figure 9J:
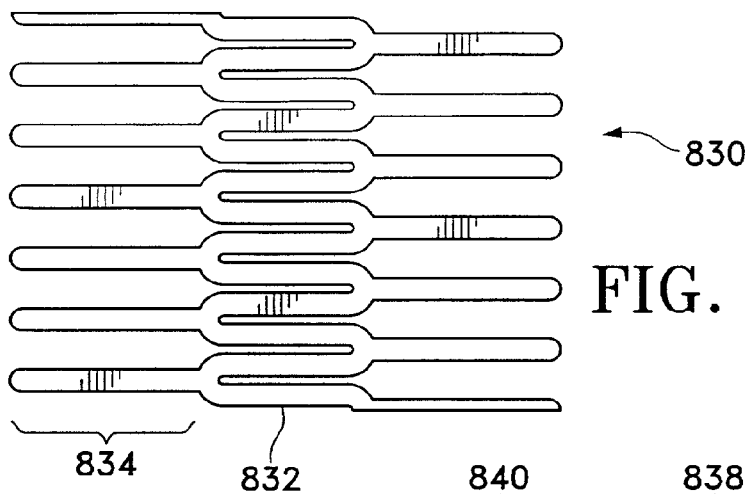
Figure 9K:
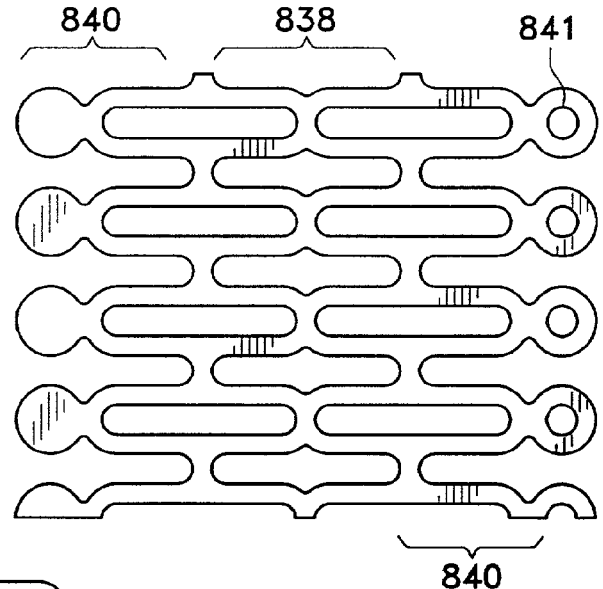
Figure 9L:
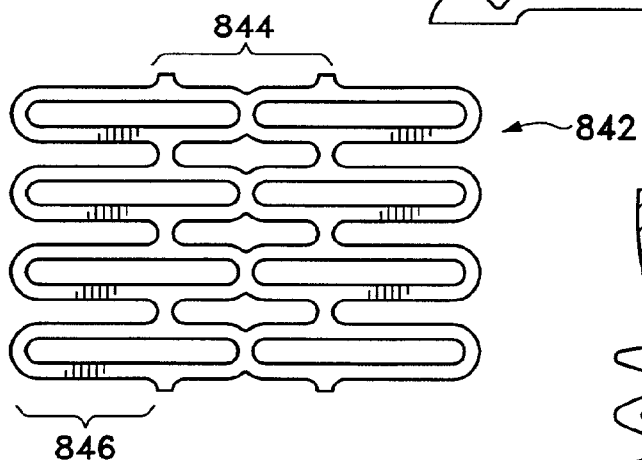
Figure 9M:
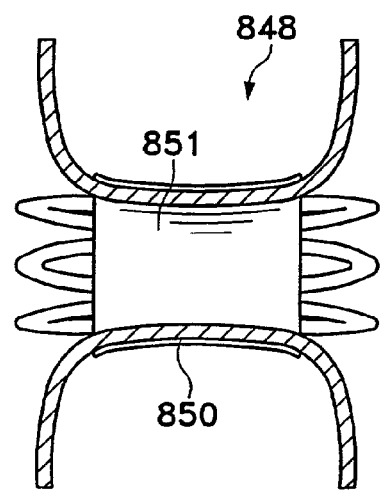

FIGS. 9J–9K illustrate various additional cross sectional designs of conduits. FIG. 9J illustrates a possible conduit design 830 having extension members 834 attached to a center section 832. FIGS. 9K and 9L illustrate additional variations of conduit designs. As illustrated in FIGS. 9K and 9L, the extension members 840, 846 and center sections 838, 844 are designed to form a diamond pattern upon expansion of the conduit. FIG. 9K further illustrates a variation of an extension member 840 having an opening 841 to facilitate tissue in-growth and thereby secures placement of the conduit. FIG. 9M illustrates an expanded conduit 848 having the diamond pattern referred to above. The conduit 848 also contains a fluid-tight barrier 851 on the center section 850 of the conduit 848. Although not illustrated, fluid-tight barrier may be placed throughout a conduit. Another feature of the variation of FIG. 9M is that the extension members have a diamond pattern construction, this construction assists in maintaining alignment of the extension members allowing for a preferred aligned expansion of the extension members.

Figure 9N:
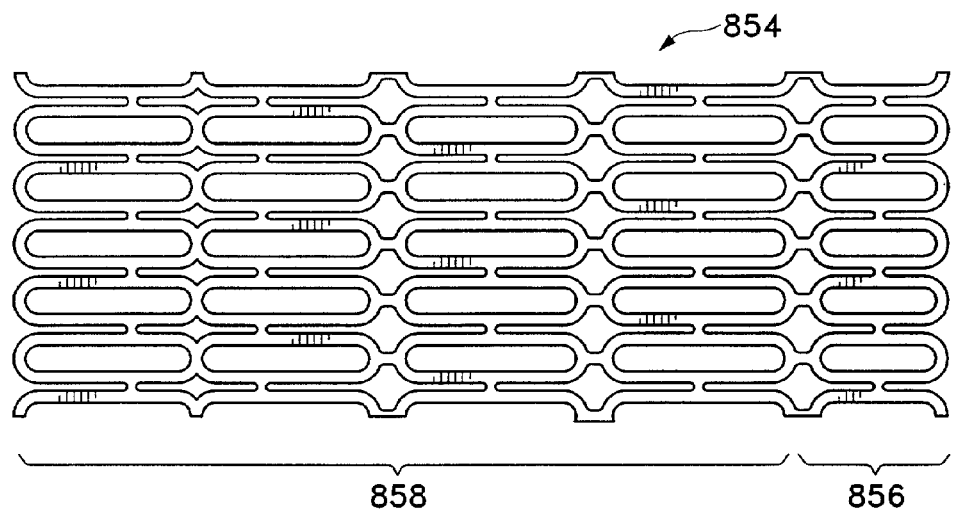
Figure 9O:
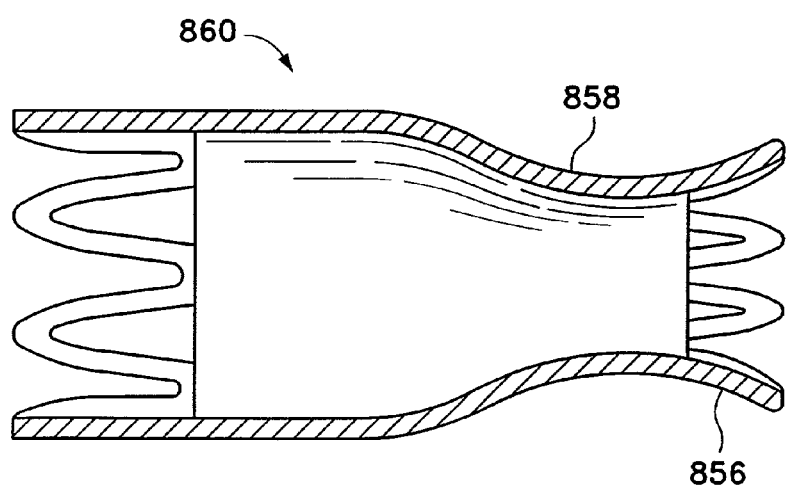

FIGS. 9N–9O illustrate another variation of a conduit 860 of the present invention. In this variation, the conduit design 854 may have extension members 856 at only one end of the conduit 860. In this variation, the center section of the conduit may comprise a body portion 858. The conduit 860 may have a covering about a portion of the conduit 860. The covering may extend throughout the length of the conduit 860 or it may be limited to a portion of the conduit 860. As illustrated in FIG. 9O, when expanded, the conduit 860 may form a reduced area 858 near the extension members 856. As mentioned above, the conduit cross section 854 may be designed such that the a diamond pattern is formed upon expansion of the conduit 860, as illustrated in FIG. 9O.

Figure 9P:
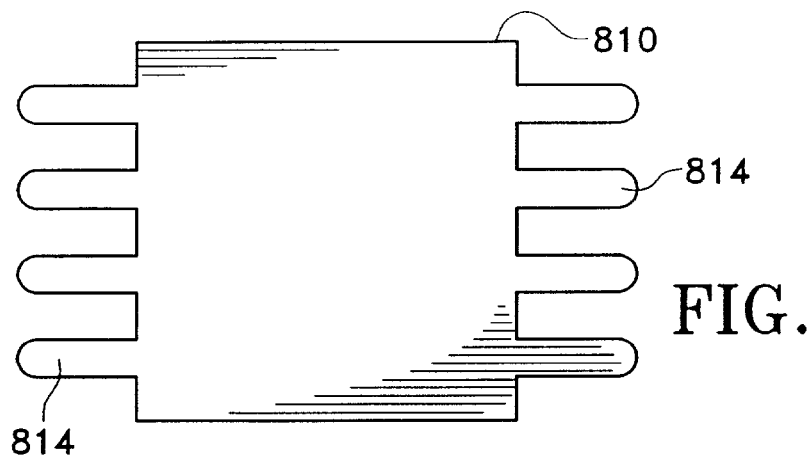
Figure 9Q:
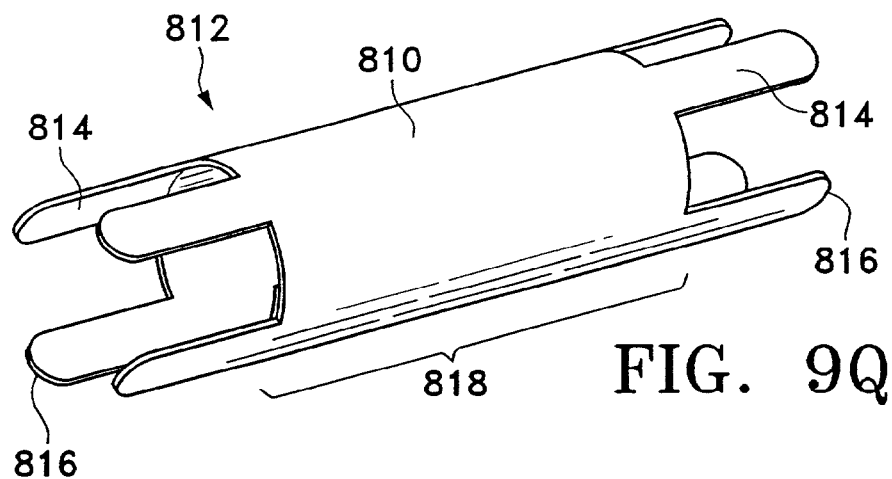
Figure 9R:
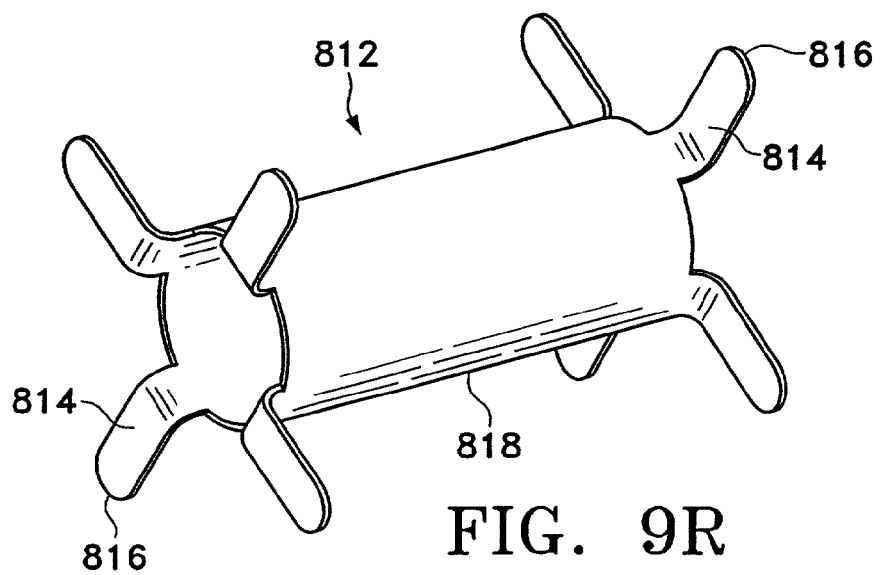

FIG. 9P illustrates a sheet of material 810 having extension members 814 extending from either end of the sheet 810. Although the sheet 810 is illustrated to be solid, a conduit may be formed from a sheet having openings within the center section of the sheet. FIG. 9Q illustrates the conduit 812 where the rolled sheet 810 comprises a center section 818 of the conduit 812 and the extension members 814 from either end of the center section 818. As illustrated in FIG. 9Q, the sheet 810 may be overlapped for a reduced profile and expanded into an expanded profile. FIG. 9R illustrates a free end 816 of each extension member 814 as having been bent away from a central axis of the conduit 812. As with any variation of a conduit of the present invention, the extension members 814 of the conduit 812 may be bent away from a central axis of the conduit 812 up to 180° with respect to the central axis. As mentioned above, the cross section and number of extension members 814 located about either end of the conduit 810 may be selected as necessary to assist in placement and securing of the conduit 810 within a channel.

In those cases where the conduit 812 of FIG. 9Q comprises a non-shape memory alloy the conduit 812 will be actively mechanically expanded. In those cases where the conduit 812 is comprised of a shape memory alloy, such as a super-elastic alloy, the conduit 812 may be pre-formed to assume a deployed shape which includes a grommet formed by extension members 814 and an expanded center section 818, such as the shape illustrated in FIG. 9R. Next, the super-elastic conduit 812 may be restrained or even rolled into the shape illustrated in FIG. 9Q. Because the conduit 812 is formed of a super-elastic material, no plastic deformation occurs. When the super-elastic conduit 812 is then placed within a collateral channel, the conduit 812 may naturally resume its pre-formed, deployed shape.

Figure 9S:
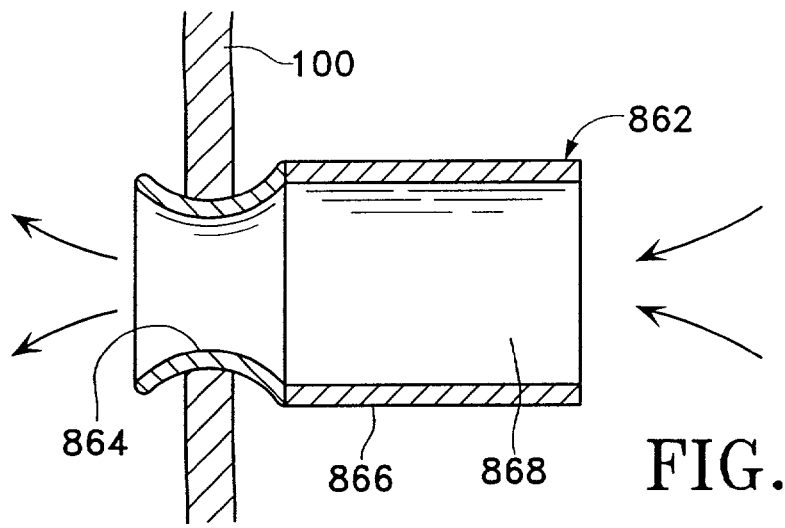

FIG. 9S illustrates another variation of a conduit 862 having a first portion 864 and a second portion 866 and a passageway 868 extending therethrough. The first portion 864 may be a conduit design as described herein. In particular, the first portion 864 is configured to secure the conduit 862 to the airway wall 100. Accordingly, the first portion 864 may or may not have a center that is expandable. The walls of the first portion 864 may be fluid-tight (either through design, or a fluid tight covering) to prevent tissue in-growth through the collateral channel. Alternatively, the first portion 864 may be partially fluid-tight to facilitate tissue in-growth to improve retention of the conduit 862 to the airway wall 100. However, in the latter case, the first portion 864 should be designed to minimize tissue in-growth within the channel to prevent substantial interference with airflow through the conduit 864. As with the first portion 864, the walls of the second portion 866 of the conduit may or may not be fluid-tight. If the second portion 866 is not fluid-tight, the larger area provides for improved airflow from lung tissue through the passageway 868 and into the airway. The second portion 866 may also be designed to be partially fluid-tight to encourage airflow through the conduit 862 but reduce the probability of blockage of the conduit 862.

Figure 9T:
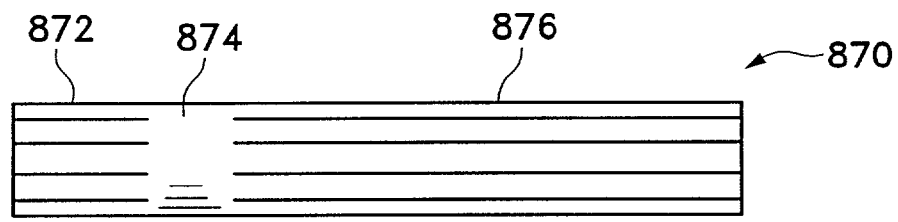
Figure 9U:
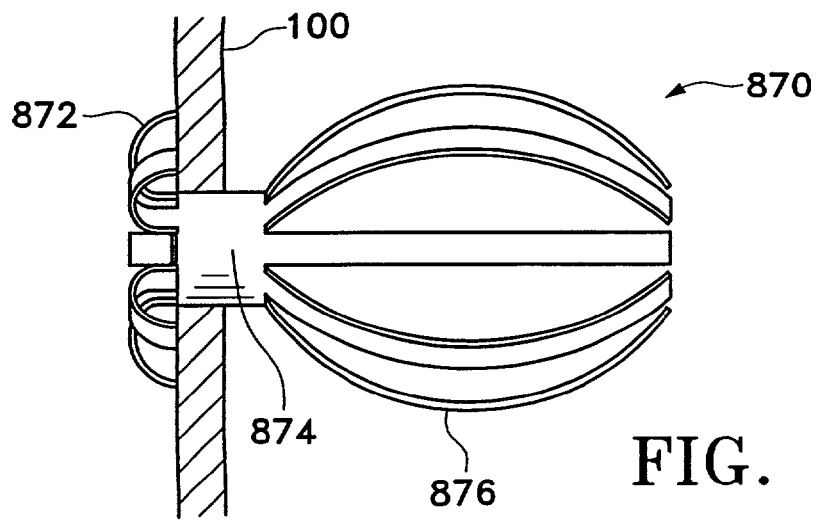

FIGS. 9T–9U illustrate another variation of a conduit 870. For example, the conduit 870 may be formed from a tube that is slit to form extension members at a first portion 872 and second portion 876 with a center section 874 between the portions. The conduit 870 may be expanded as shown in FIG. 9U such that the first 872 and second 876 portions maintain the center portion 874 in a collateral channel in an airway wall. The center section 874 may or may not be expandable.

FIG. 9U illustrates the second portion 876 of the conduit 870 to expand in its center, however, the conduit 870 may be designed in other configuration as well (e.g., expanded to have a larger diameter at an end opposite to the center section 874.) However, a central aspect of this design is that the second portion 870 provides a large area in the lung tissue to permit a larger volume of air to pass from the lung tissue into the conduit 870. This design has an added benefit as the second portion 876 cannot be easily blocked by flaps of parenchyma tissue. A simple variation of the conduit 870 may be constructed from a metal tube, such as 316 stainless steel, titanium, titanium alloy, nitinol, etc. Alternatively, the conduit may be formed from a rigid or elastomeric material.

The conduits described herein may be comprised of a metallic material (e.g., stainless steel), a shape memory alloy, a super-elastic alloy (e.g., a NiTi alloy), a shape memory polymer, a polymeric material or a combination thereof. The conduit may be designed such that its natural state is an expanded state and it is restrained into a reduced profile, or, the conduit may be expanded into its expanded state by a variety of devices (e.g., a balloon catheter.) The conduit described herein may be manufactured by a variety of manufacturing processes including but not limited to laser cutting, chemical etching, punching, stamping, etc.

The conduits described herein may be coated with an elastomer, e.g., silicone, polyurethane, etc. The coatings may be applied, for example, by either dip coating, molding, or liquid injection molding (for silicone). Or, the coating may be a tube of a material and the tube is placed either over and/or within the conduit. The coating(s) may then be bonded, crimp, heated, melted, or shrink fit. The coatings may also be placed on the conduit by either solvent swelling applications or by an extrusion process. Also, a coating of may be applied by either wrapping a sheet of PTFE about and/or within the conduit, or by placing a tube about and/or within the conduit and securing the tubes.

Figure 10A:
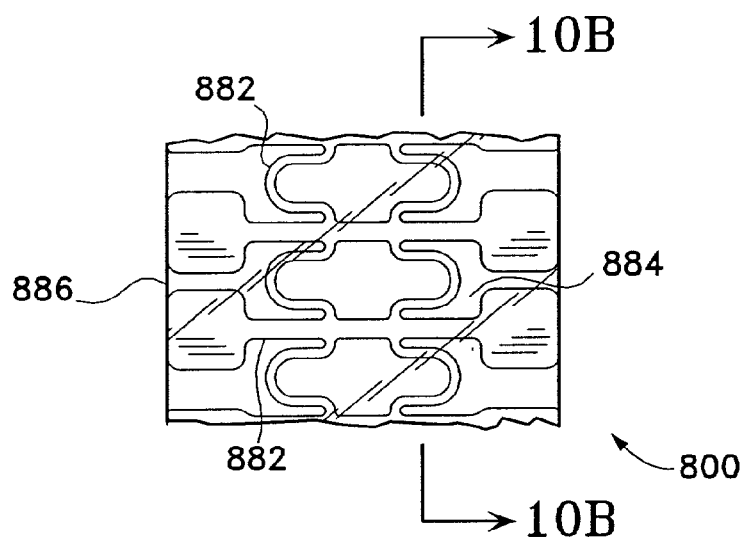
Figure 10B:
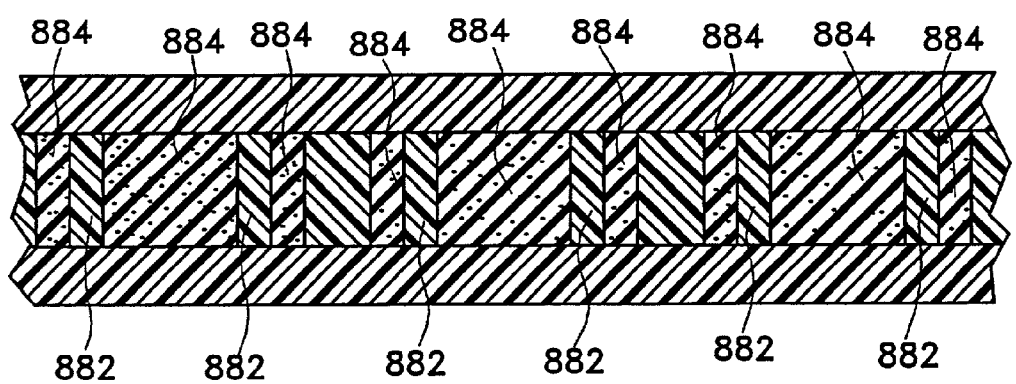
Figure 11A:
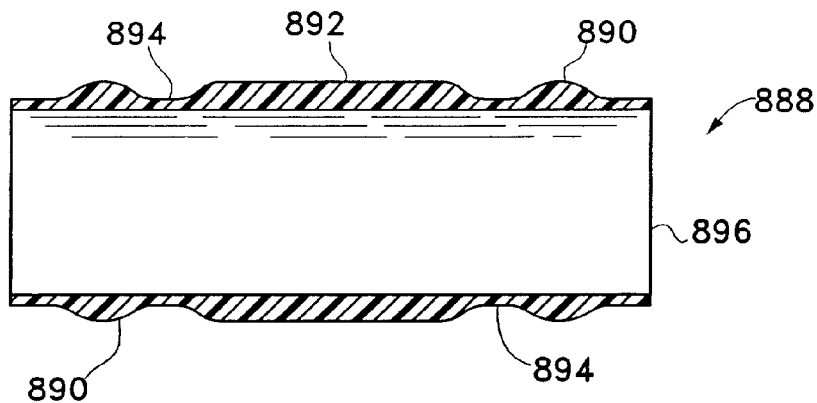
Figure 11B:
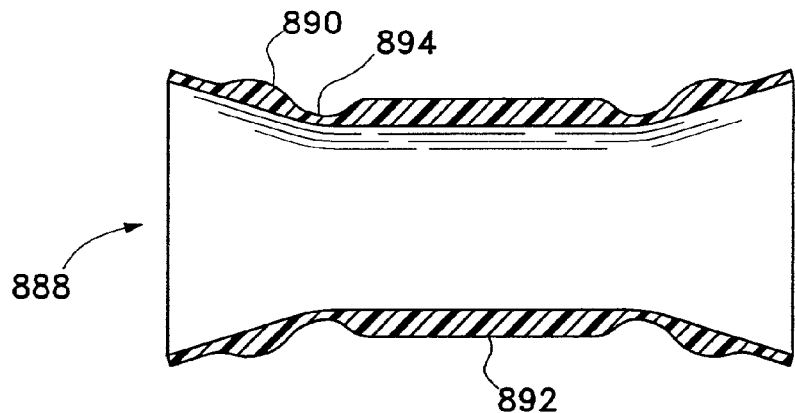
Figure 11C:
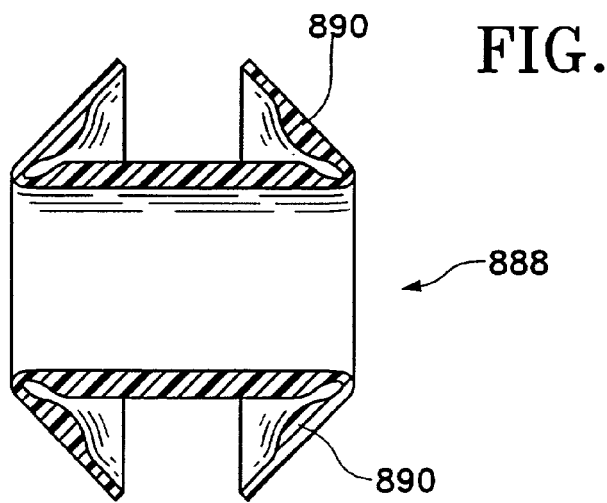

Another variation of the invention is illustrated in FIGS. 10A–10B. In this variation, a conduit of the present invention contains a filler material between the openings of the ribs or mesh. For example, FIG. 10A illustrates a partial plane view of a conduit 880 having a plurality of ribs or a mesh structure 882 as previously described. The conduit 880 includes placing a filler material 884 between each of the ribs/opening of the mesh. A covering 886 is then placed over the ribs/mesh 882 and filler material 884. The covering 880 encapsulates the structure of the conduit 880 and covers the outer surface of the conduit 880 and the interior wall of the lumen or passageway of the conduit 880. FIG. 10B illustrates a partial sectional view of the conduit 880 of FIG. 10A. FIG. 10B illustrates the mesh 882 with filler material 884 adjacent to the mesh 882 and an outer covering 886 encapsulating the mesh 882 and filler material 884. It is noted that the filler material 884 and covering 886 may be placed entirely throughout a conduit. Alternatively, the filler material 884 and covering 886 may be placed partially over a conduit as needed. It is believed that the addition of filler material to a conduit of the present invention provides a uniform thickness of the covering which results in uniform and consistent stretching of the covering. Some various examples of filler material are, for example, wax, silicone, and urethane. The covering may consist of, for example, silicone, urethane, or similar materials. FIGS. 11A–11C illustrate another variation of a conduit 888 of the present invention. In this variation, the conduit comprises a continuous phase material 896 that is weak enough to expand but strong enough to keep a particular size and shape upon expansion of the conduit 888. Some examples of a continuous phase material are polytetrafluoroethylene and polypropylene. These materials exhibit plastic deformation without exhibiting tears or breaches in their surfaces when expanded. These materials may be selected to have a properties (e.g., modulus, yield stress, etc.) which permit expansion of the conduit into a desired shape and retention of that shape. To further assist in controlling the expansion and shape of the installed conduit 888, the conduit may have weakened sections that permit the ends of the conduit to bend as desired. For example, the wall thickness of the conduit 888 may vary as illustrated. As shown in FIG. 11A, the wall thickness of the material 896 between the extension members 890 and the center section 892 may be less than a thickness of the wall section of the material 896 at the center section 892. As illustrated, if an outwardly radial force is applied to the extension members 890, such a configuration results in a higher bending stress at the area of reduced wall thickness 894. As a result, and as illustrated in FIGS. 11B–11C, the extension members 890 expand in a predetermined manner.

As mentioned above, the number of and cross sectional area of the extension members on a conduit may be selected as needed for the particular application. Also, the extension members may be bent such that they anchor into the tissue thereby securing placement of the conduit. Or, the extension members or the center section may contain barbs or other similar configurations to better adhere to the tissue. Moreover, the orientation of the extension members may vary as well. For example, the extension members may be configured to be radially expanding from the center section, or they may be angled with respect to a central axis of the conduit. Another variation of the invention includes a radioactive conduit which inhibits or prevents the growth of tissue within the conduit.

Although the conduits of the current invention have been described to contain expandable center sections, the invention is not necessarily limited as such. Instead, the design of the conduit may require extension members on the ends of a conduit with a non-expandable center section.

FIGS. 12A–12D illustrate a conduit 900 of the present invention. The deployment of the conduit 900 is intended to show an example of a possible means of deployment only. Accordingly, the inventive conduit may be delivered at an angle via an articulating or jointed device, the conduit may be delivered on a device that is adapted to locate and create the collateral channel, or the conduit may be delivered on a device having other features as needed for the particular application.

Figure 12A:
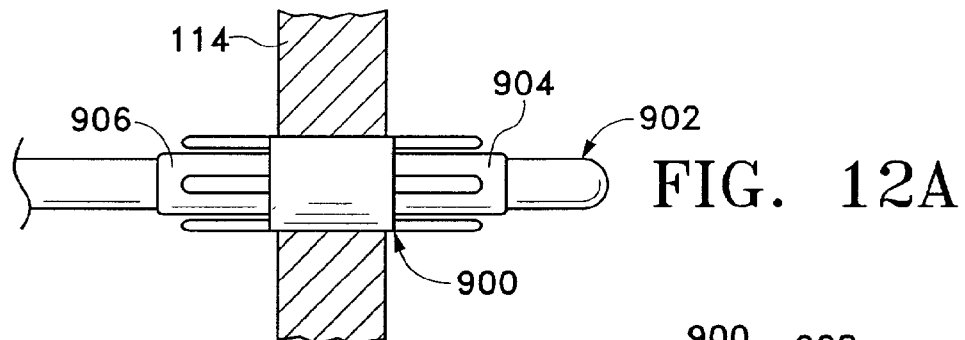
FIGS. 12A–12I illustrate variations of methods and devices for deployment of conduits of the present invention.
Figure 12B:
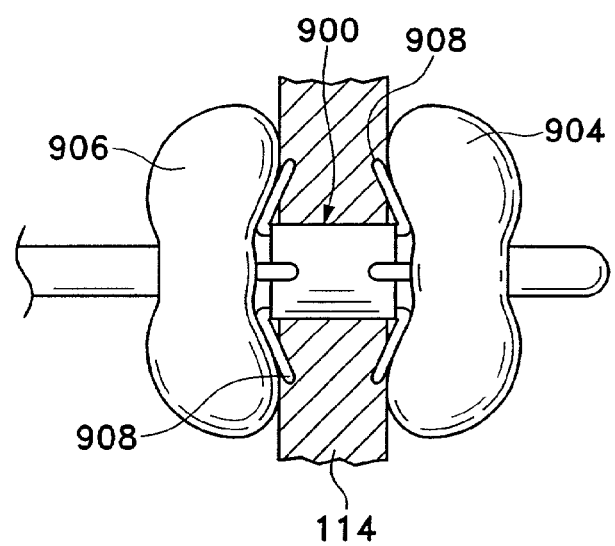

FIG. 12A illustrates the conduit 900 being delivered to a collateral channel in an airway wall 114 via a delivery device (e.g., a balloon catheter 902.) The conduit 900 may be attached to the delivery device 902 using the natural resiliency of the conduit 900. Or, in those cases where the conduit is spring loaded, the conduit 900 restrained in a reduced profile and may be removably affixed to the delivery device 902 using an adhesive, or a removable sleeve such as a heat shrink tube. In this example, the balloon catheter 902 has several balloons including a distal balloon 904, a proximal balloon 906, and a center balloon (not illustrated in FIG. 12A). FIG. 12B illustrates the inflation of the distal 904 and proximal 906 balloons to situate the extension members 908. Accordingly, the extension members 908 for a flange or collet about the airway wall 114. The balloons 904, 906 may be inflated simultaneously, or in a desired sequence. In any case, deployment of the balloons 904, 906 may serve to center the conduit 900 in the collateral channel.

Figure 12C:
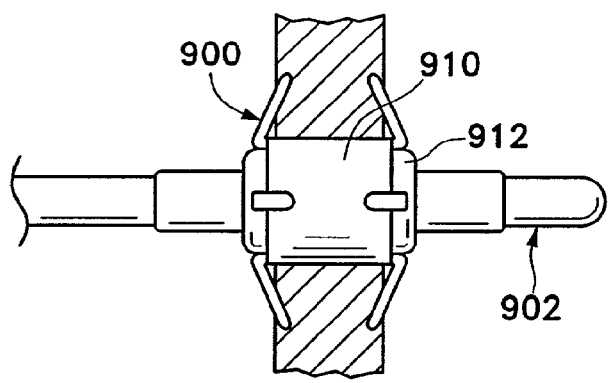
Figure 12D:
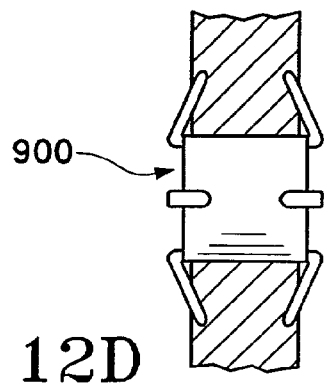
Figure 12E:
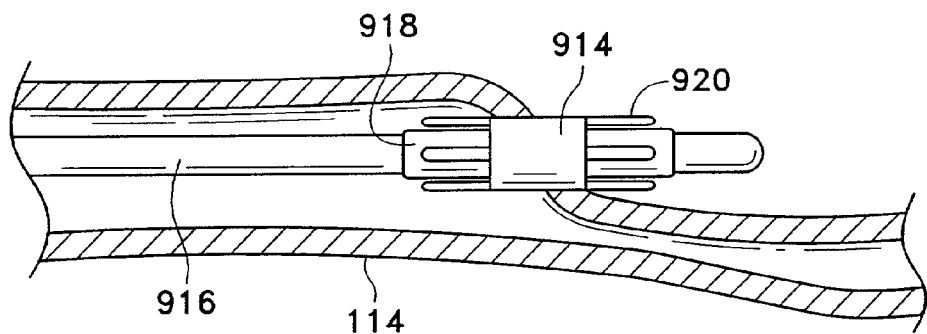
Figure 12F:
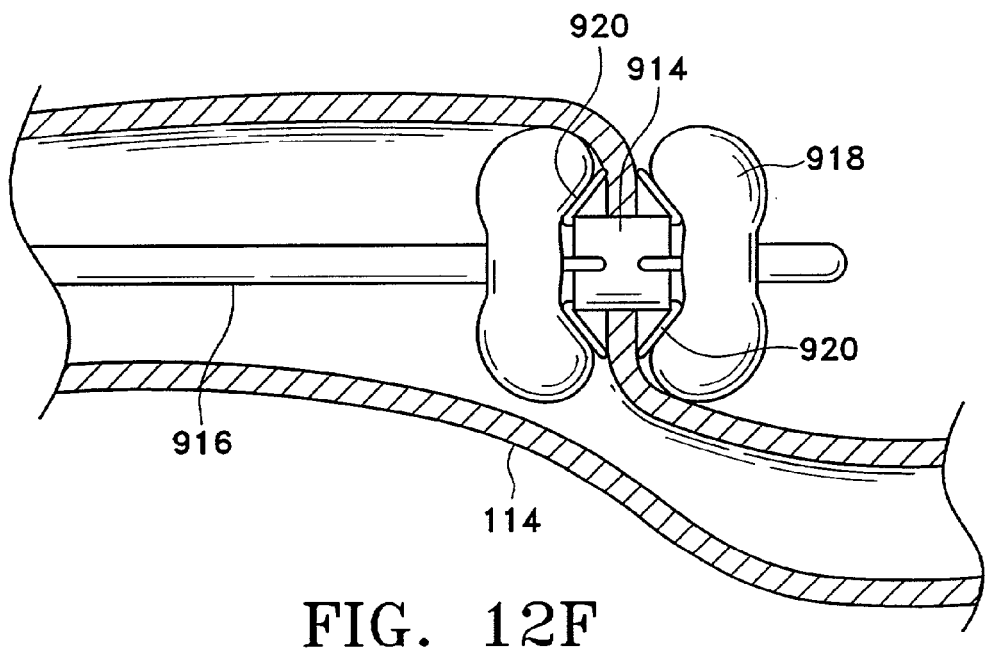

FIG. 12C illustrates inflation of the center balloon 912 which causes expansion of the center section 910 of the conduit 900. If the conduit 900 is affixed to the delivery device 902, expansion of the center balloon 912 causes release of the conduit 900 by release of the adhesive or breaking of the heat shrink tubing (not shown). In any case, the means of attachment may be bioabsorbable and remain in the body, or may remain affixed to the delivery device 902 and is removed with removal of the delivery device 902. FIG. 12D illustrates the conduit 900 affixed to the airway wall 114 after the delivery device 902 is removed from the site. Another method of deploying a conduit includes restraining the conduit about a delivery device using a wire or string tied in a slip-knot or a series of slip-knots. When the conduit is delivered to a desired location, the proximal end of the wire or string may be pulled which releases the wire/string and deploys the conduit. FIGS. 12E and 12F illustrate possible ways to manipulate a conduit 914 for placement in an airway wall 114 using a delivery device 916. FIG. 12E illustrates deployment of a delivery device 916 to place a conduit 914 within an opening in an airway wall 114. The conduit 914 may be placed over a balloon 918 (or other expandable section) of the delivery device 916. FIG. 12F illustrates deployment of the balloon 918 to place and expand the conduit 914. In the variation illustrated in FIGS. 12E and 12F, a balloon 918 serves several functions. The balloon 918 first expands and starts bending the extension members 920. The balloon 918 continues to center the conduit 914 on the tissue and simultaneously begins to expand the conduit 914 and secures the conduit to the tissue.

Figure 12G:
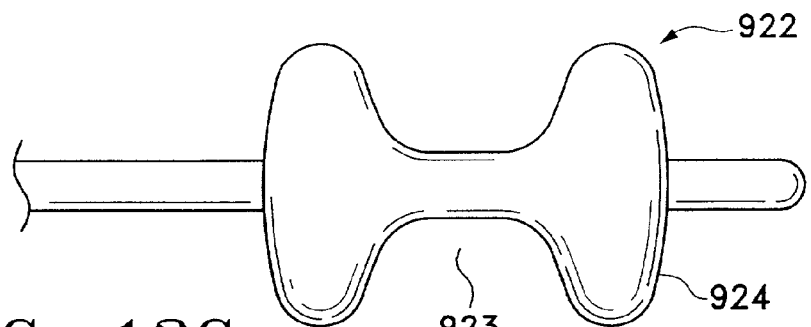
Figure 12H:
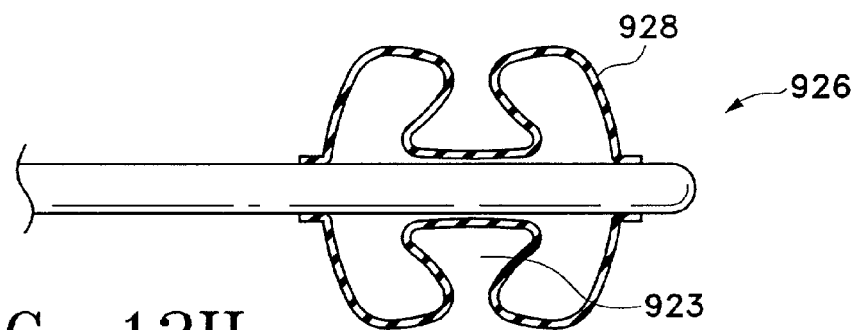

FIGS. 12G and 12H illustrate additional variations of deployment devices. In these variations, the deployment devices 922, 926 contain hourglass-shaped balloons 924, 928. The hour glass-shaped balloons 924, 928 contain an interior profile 923. For deployment of a conduit (not shown) of the present invention, the conduit is placed on the balloon 924, 928. As the balloon 924, 928 expands, the conduit expansion matches the interior profile 923 of the balloon 924, 928. Accordingly, the hour glass-shaped balloon 924, 928 may be used to set the angle and orientation of the expandable members of a conduit as well as the expansion of a center section of the conduit.

Figure 12I:
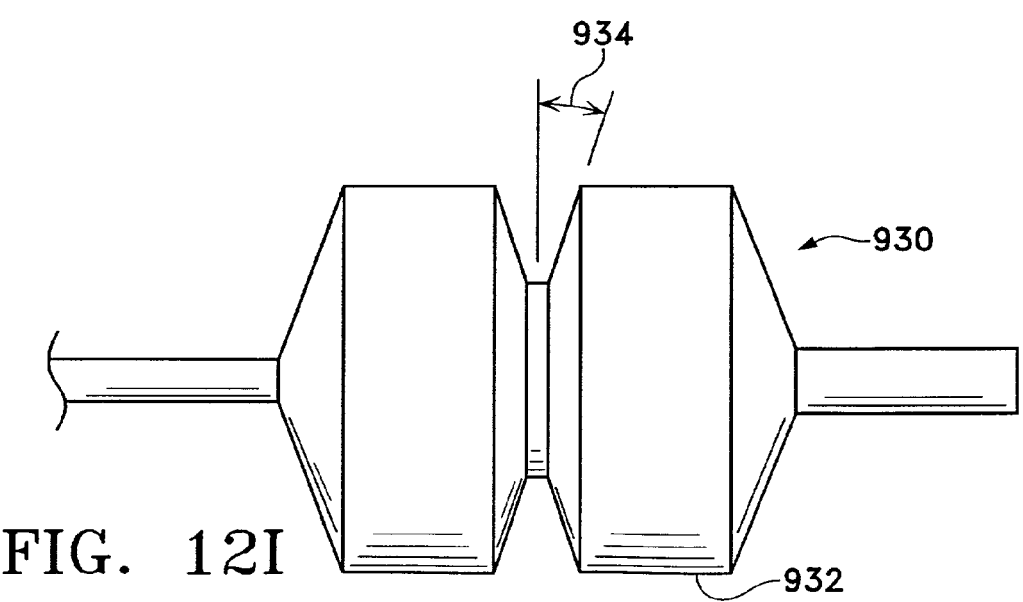

FIG. 12I illustrates another variation of an hour glass shaped balloon delivery device 930. This variation of the hour glass shaped balloon 932 is designed to expand extension members (not shown) of a conduit (not shown) at a particular angle 934. The orientation of the balloon 932 may be designed as needed to impart the desired angle to the extension members of the conduit. The balloons described herein may be constructed of polyethylene terephthalate (PET) or any other material which is used in the construction of balloon catheters.

Figure 13A:
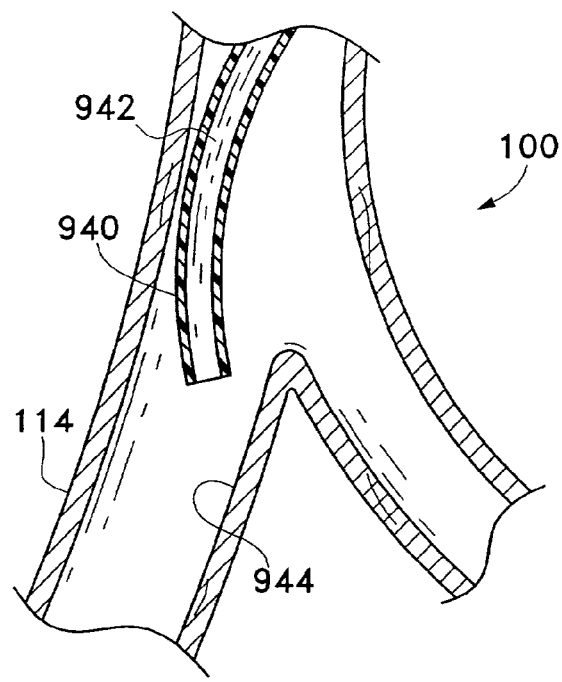
FIGS. 13A–13F illustrate methods of placing a conduit within tissue.

FIG. 13A illustrates a method of placing a conduit within lung tissue. FIG. 13A illustrates the advancement of an access device 940 into the airways 100 of a lung. The access device 940 will have at least one lumen or working channel 942. The access device 940 will locate an approximate site 944 for creation of a collateral channel. A bronchoscope or other similar type of endoscope may be used as the access device 940. In cases where the access device 940 is a bronchoscope or similar device, the access device 940 is equipped so that the surgeon may observe the site for creation of the collateral channel. However, it is contemplated that the method of placing a conduit within lung tissue may be performed using non-invasive imaging techniques as well. In such a case, the access device 940 as well as the other devices discussed herein, may be configured for detection by the particular non-invasive imaging technique such as fluoroscopy, "real-time" computed tomography scanning, or other technique being used.

Figure 13B:
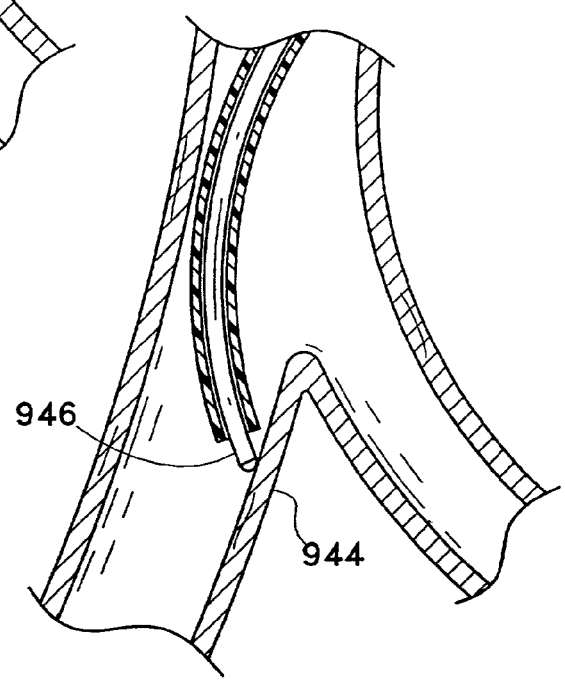

FIG. 13B illustrates a blood vessel detection device 946 advanced through the channel 942 of the access device 940 towards the site 944. The site 944 is then inspected to determine whether a blood vessel is adjacent to the site. As discussed herein, it may be desirable to avoid blood vessels when creating a collateral channel. Some possible examples of the detection device 946 are disclosed throughout this disclosure.

Figure 13C:
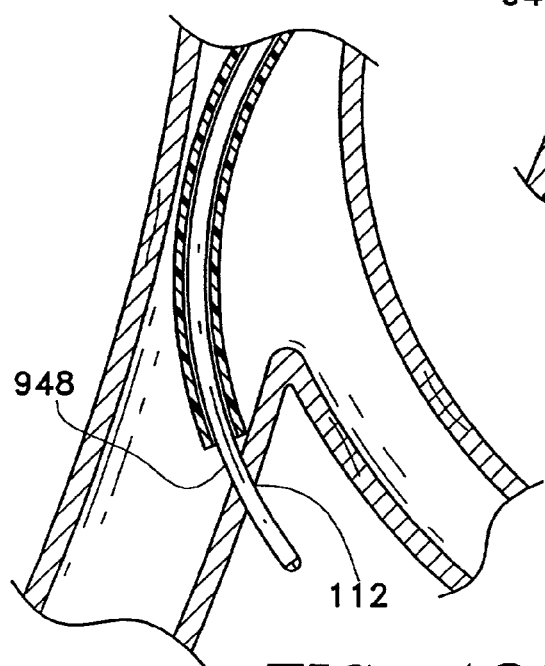

FIG. 13C illustrates the creation of a collateral channel 112 by a hole-making device 948. Examples of hole-making devices 948 are disclosed throughout this specification. Furthermore, variations of this invention include the use of devices which are equipped for detection and hole-making. Such devices are also disclosed throughout this specification. As shown in FIG. 13C, the device 948 may be manipulated to a position that is optimal for creation of the collateral channel 112. It is noted that the access device or the hole-making device may be steerable. Such a feature may assist in the positioning of any of the devices used in the inventive method. Although it is not illustrated, as discussed herein, it is desirable to create the collateral channel such that it is in fluid communication with an air-sac. The fluid communication allows for the release of trapped gasses from the hyper-inflated lung.

Figure 13D:
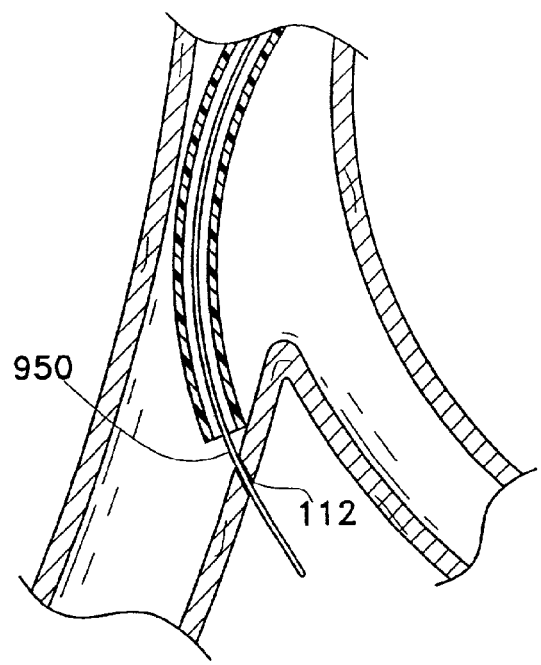

FIG. 13D illustrates another variation of the inventive method in which a guide-member, such as a guide-wire 950, or other similar device, is inserted into the collateral channel 112. It is noted that the use of a guide-member 950 is optional.

Figure 13E:
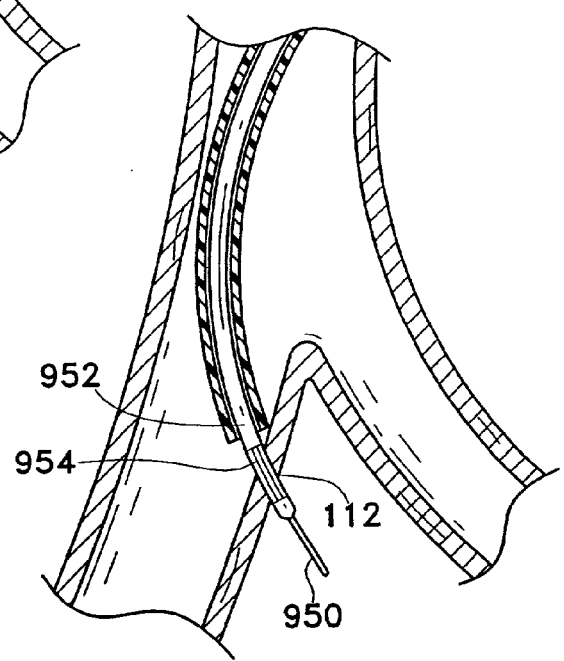

FIG. 13E illustrates the advancement of a catheter device 952 into the collateral channel. In the variations using a guide-member 950, the catheter 952 is advanced over the guide-member 950 and into the collateral channel 112. One variation of the inventive method includes the use of a catheter 952 which has a conduit 954 attached thereto. Some examples of the conduit 954 as well as catheter type delivery devices 952 are disclosed throughout this disclosure. If the conduit 954 is of the type that is not self-expanding, the catheter 952 may also be configured to expand the conduit 954 within the collateral channel 112.

Figure 13F:
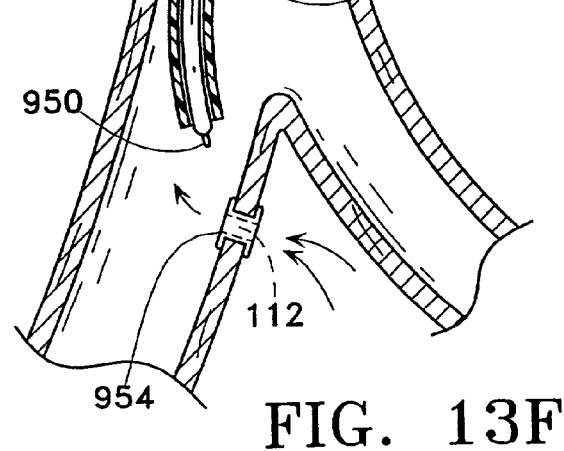

FIG. 13F illustrates the conduit 954 placed within the collateral channel 112 and the withdrawal of the guide-member 950, catheter 952, and the access device 940. As shown by the arrows of FIG. 13F, the conduit 954 maintains the collateral channel 112 open so that trapped non-functional air is evacuated from the hyper-inflated lung.

It is noted that a variation of the inventive method includes using a guide-wire to create the collateral channel and leaving the guide-wire to extend through the collateral channel. Accordingly, a conduit may be advanced over the guide-wire into the collateral channel.

The invention further includes methods of evaluating individuals having a diseased lung to assess inclusion of the individual for the procedure.

The method comprises the steps of performing pulmonary function tests on the individual. The pulmonary function tests may obtain such values as FEV (forced expiratory volume), FVC (forced vital capacity), $FEF_{25\%-75\%}$ (forced expiratory flow rate), PEFR (peak expiratory flow rate), FRC (functional residual capacity), RV (residual volume), TLC (total lung capacity), and/or flow/volume loops.

FEV measures the volume of air exhaled over a pre-determined period of time by a forced expiration immediately after a full inspiration. FVC measures the total volume of air exhaled immediately after a full inspiration. $FEF_{25\%-75\%}$ measures the rate of air flow during a forced expiration divided by the time in seconds for the middle half of expired volume. PEFR measures the maximum flow rate during a forced exhale starting from full inspiration. FRC is the volume of air remaining in the lungs after a full expiration. RV is the FRC minus the expiratory reserve volume. TLC is the total volume in the lungs at the end of a full inspiration. Flow/volume loops are graphical presentations of the percent of total volume expired (on the independent axis) versus the flow rate during a forced expiratory maneuver.

The invention further comprises methods to determine the completion of the procedure. This variation of the invention comprises the step of performing pulmonary function tests as described above, creating collateral channels in the lungs, performing a post-procedure pulmonary function test, obtaining clinical information, comparing the results of the tests, evaluating the clinical information with the results of the test to determine the effectiveness of the procedure.

Another method to determine the completion of the procedure includes checking the resistance of airflow upstream from a location of a collateral channel. The method includes making a collateral channel, checking airflow, measuring resistance to airflow, and repeating the procedure until acceptable resistance is obtained. Because the collateral channel allows for the release of trapped air, the resistance to airflow should decrease. A body plethysmograph or other suitable equipment used to measure in pulmonary medicine may be used to determine the resistance to airflow.

A measurement of total lung volume may be used to determine when the lung is suitably deflated and therefore when enough collateral channels are created. Or, non-invasive imaging may be used to determine pre and post procedure lung volume or diaphragm position.

An evaluation of the effectiveness of the procedure may also include creating a collateral channel then sealing the channel with a balloon catheter. The distal end of catheter is then opened for a measurement of the flow of trapped air through the catheter.

This variation of the invention includes obtaining clinical information regarding the quality of life of the individual before and after any procedures, physical testing of the pulmonary system of the individual, and a general screening for pulmonary condition.

The invention further includes a medical kit for improving gaseous flow within a diseased lung. The components of the kit may include a conduit, a hole-making device, and/or a detection device all of which are of the present invention and as described herein. The kit may further contain a power supply, such as an RF generator, or a Doppler controller which generates and analyzes the signals used in the detection devices. The kit may include these components either singly or in combination. The kit of the present invention may also contain instructions teaching the use of any device of the present invention, or teaching any of the methods of the present invention described herein. The instructions may actually be physically provided in the kit, or it may be on the covering, e.g., lidstock, of the kit. Furthermore, the kit may also comprise a bronchoscope, or guide-member (such as a guide-wire), or other such device facilitating performance of any of the inventive procedures described herein.

The invention herein is described by examples and a desired way of practicing the invention is described. However, the invention as claimed herein is not limited to that specific description in any manner. Equivalence to the description as hereinafter claimed is considered to be within the scope of protection of this patent.

The invention claimed is:

1. A implantable conduit for maintaining the patency of an opening in tissue, the conduit being detachable from a balloon catheter for remote implantation within the opening, the conduit comprising:
   a center section having a first end and a second end and a central axis extending between said ends, a passageway within said center section extending between said ends, said center section having a wall; and
   a plurality of independent extension members extending from both of the first and second ends of the center section where each extension member is unconnected to an adjacent extension member such that the extension member is independently moveable relative to the adjacent extension member, said extension members having a wall;
   wherein at least a portion of said wall of each said extension members has a weakened section comprising a reduced cross-sectional wall thickness such that said extension members may bend at said respective weakened section when an outward radial force is applied thereto such that each extension member flares independently to form a cuff or grommet shape to keep the conduit within the tissue opening.

2. The conduit of claim 1, wherein said reduced cross-sectional wall thickness of said weakened section is less than a thickness of said wall of said center section.

3. The conduit of claim 1, wherein said conduit comprises a material selected from the group consisting of polytetrafluoroethylene, polypropylene, and a combination thereof.

4. The conduit of claim 1, wherein said center section is radially expandable away from said central axis to allow said center section to assume an expanded profile from a reduced profile.

5. The conduit of claim 4, wherein a length of said center section is less than twice the square root of a cross sectional area of said center section when said center section is in said expanded profile.

6. The conduit of claim 4, wherein a length of said center section measured along said central axis decreases as said center section expands from said reduced profile to said expanded profile.

7. The conduit of claim 4, wherein said center section comprises a shape memory alloy.

8. The conduit of claim 1, where said extension members extending from said first end of said conduit are longer than said extension members extending from a second end of said conduit.

9. The conduit of claim 1, wherein said passageway has a cross sectional area between 0.196 mm$^2$ to 254 mm$^2$.

10. The conduit of claim 1, wherein said passageway has a cross sectional area between 3 mm$^2$ to 20 mm$^2$.

11. The conduit of claim 1, wherein said conduit has an asymmetrical profile.

12. The conduit of claim 1, wherein said conduit has a ratio of a length to a diameter of approximately 1:1.

13. The conduit of claim 1, further comprising a self-cleaning mechanism within said passageway.

14. The conduit of claim 13, wherein said self-cleaning mechanism is a ball bearing shaker valve.

15. The conduit of claim 1, further comprising a one-way valve located within said passageway.

16. The conduit of claim 1, further comprising a gas-permeable bacterial-resistant barrier located within said passageway.

17. The conduit of claim 1, further comprising a barrier layer extending over at least a portion of the conduit.

18. The conduit of claim 17, where the barrier layer extends over the center section.

19. The conduit of claim 17, where the barrier layer extends over the entire conduit.

20. An implant for placement in an opening within an airway wall, the implant being remotely deployable from a catheter to remain within the opening and comprising:
   a center section having a first end and a second end and a central axis extending between said ends, a passageway within said center section extending between said ends, said center section having a wall;
   a plurality of indenendent extension members extending from both of the first and second ends of the center section, where each extension member is unconnected to an adjacent extension member such that the extension member is independently moveable relative to the adjacent extension member said extension members having a wall;
   wherein at least a portion of said wall of said extension members has a weakened section such that each of said extension members may bend at said respective weakened section when an outward radial force is applied to said extension member causing each extension member to flare independently and form a cuff or grommet shape to keep the conduit within the tissue opening.

21. The implant of claim 20, wherein said center section is radially expandable away from said central axis to allow said center section to assume an expanded profile from a reduced profile.

22. The implant of claim 20, wherein said center section comprises a shape memory alloy.

23. The implant of claim 20, further comprising a barrier layer extending over at least a portion of the implant.

24. The implant of claim 23, where the barrier layer extends over the center section.

25. The implant of claim 23, where the barrier layer extends over the entire implant.

* * * * *

UNITED STATES PATENT AND TRADEMARK OFFICE
CERTIFICATE OF CORRECTION

PATENT NO. : 7,175,644 B2 Page 1 of 1
APPLICATION NO. : 09/947144
DATED : February 13, 2007
INVENTOR(S) : Joel D. Cooper et al.

It is certified that error appears in the above-identified patent and that said Letters Patent is hereby corrected as shown below:

In column 11, line 19, please replace "maybe" with --may be--, and
In column 14, line 40, please replace "FIG. 30" with --FIG. 3O--.

Signed and Sealed this

First Day of April, 2008

JON W. DUDAS
*Director of the United States Patent and Trademark Office*